US011345728B2

(12) United States Patent
Hinner et al.

(10) Patent No.: US 11,345,728 B2
(45) Date of Patent: *May 31, 2022

(54) SPECIFIC-BINDING POLYPEPTIDES AND USES THEREOF

(71) Applicant: Pieris Pharmaceuticals GmbH, Hallbergmoos (DE)

(72) Inventors: Marlon Hinner, Munich (DE); Alexander Wiedenmann, Ulm (DE); Andrea Allersdorfer, Geisenhausen (DE)

(73) Assignee: Pieris Pharmaceuticals GmbH, Hallbergmoos (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/987,218

(22) Filed: Aug. 6, 2020

(65) Prior Publication Data

US 2020/0377563 A1    Dec. 3, 2020

Related U.S. Application Data

(62) Division of application No. 15/312,094, filed as application No. PCT/EP2015/061034 on May 20, 2015, now Pat. No. 10,774,119.

(30) Foreign Application Priority Data

May 22, 2014    (EP) .................................... 14169488

(51) Int. Cl.
*C07K 14/47* (2006.01)
*G01N 33/68* (2006.01)
*A61K 38/00* (2006.01)

(52) U.S. Cl.
CPC ......... *C07K 14/47* (2013.01); *G01N 33/6869* (2013.01); *A61K 38/00* (2013.01)

(58) Field of Classification Search
CPC .... C07K 14/47; C07K 14/54; G01N 33/6869; A61K 38/00; A61K 38/16
See application file for complete search history.

(56) References Cited

U.S. PATENT DOCUMENTS

| | | |
|---|---|---|
| 5,728,553 A | 3/1998 | Goodey et al. |
| 5,849,576 A | 12/1998 | Skerra et al. |
| 6,099,517 A | 8/2000 | Daugherty |
| 6,103,493 A | 8/2000 | Skerra et al. |
| 6,123,936 A | 9/2000 | Platz et al. |
| 6,177,074 B1 | 1/2001 | Glue et al. |
| 6,403,564 B1 | 6/2002 | Ganguly et al. |
| 6,500,930 B2 | 12/2002 | Adamson |
| 6,620,413 B1 | 9/2003 | De Sauvage et al. |
| 6,696,245 B2 | 2/2004 | Winter et al. |
| 7,118,915 B2 | 10/2006 | Vogt et al. |
| 7,250,297 B1 | 7/2007 | Beste et al. |
| 7,252,998 B2 | 8/2007 | Skerra et al. |
| 7,893,208 B2 | 2/2011 | Skerra et al. |
| 8,313,924 B2 | 11/2012 | Jensen et al. |
| 8,986,951 B2 | 3/2015 | Hohlbaum et al. |
| 9,051,382 B2 | 6/2015 | Trentmann et al. |
| 9,260,492 B2 | 2/2016 | Matschiner et al. |
| 9,549,968 B2 | 1/2017 | Skerra et al. |
| 9,884,898 B2 | 2/2018 | Corvey et al. |
| 10,273,275 B2 | 4/2019 | Hinner et al. |
| 10,526,384 B2 | 1/2020 | Hinner et al. |
| 10,618,941 B2 | 4/2020 | Skerra et al. |
| 10,774,119 B2 | 9/2020 | Hinner et al. |
| 2003/0069395 A1 | 4/2003 | Sato et al. |
| 2006/0058510 A1 | 3/2006 | Skerra et al. |
| 2006/0088908 A1 | 4/2006 | Skerra et al. |
| 2008/0044423 A1 | 2/2008 | Cochrane et al. |
| 2009/0042785 A1 | 2/2009 | Matschiner et al. |
| 2013/0079286 A1 | 3/2013 | Skerra et al. |
| 2015/0344538 A1 | 12/2015 | Hinner et al. |
| 2017/0107266 A1 | 4/2017 | Hinner et al. |
| 2017/0114109 A1 | 4/2017 | Skerra et al. |
| 2017/0166615 A1 | 6/2017 | Matschiner et al. |
| 2017/0369542 A1 | 12/2017 | Trentmann et al. |
| 2018/0016312 A1 | 1/2018 | Bel Aiba et al. |
| 2018/0141988 A1 | 5/2018 | Hinner et al. |
| 2018/0148484 A1 | 5/2018 | Hinner et al. |
| 2020/0148733 A1 | 5/2020 | Hinner et al. |
| 2020/0308237 A1 | 10/2020 | Skerra et al. |

FOREIGN PATENT DOCUMENTS

| | | |
|---|---|---|
| CN | 101611057 A | 12/2009 |
| DE | 4417598 A1 | 12/1995 |
| DE | 19641876 A1 | 4/1998 |
| DE | 19742706 A1 | 4/1999 |
| DE | 19926068 C1 | 1/2001 |

(Continued)

OTHER PUBLICATIONS

Bowie et al (Science, 1990, 247:1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*
"Chain A Crystal Structure of Siderocalin (Ngal, Lipocalin 2) Complexed With Trencam-3,2-Hopo, A Cepabactin Analogue," GenBank Accession No. 1X71_A, Sep. 24, 2008.

(Continued)

*Primary Examiner* — Sudhakar Katakam
(74) *Attorney, Agent, or Firm* — Honigman LLP; Douglas H. Siegel; Jonathan P. O'Brien

(57) ABSTRACT

The present invention relates to novel, specific-binding therapeutic and/or diagnostic polypeptides directed against the target of Swiss Prot Q16552 and novel, specific-binding therapeutic and/or diagnostic polypeptides directed against the target of Swiss Prot Q9NPF7. In addition, the present invention relates to novel, specific-binding therapeutic and/or diagnostic polypeptides directed against one or both of Swiss Prot Q16552 and Swiss Prot Q9NPF7. The invention also relates to nucleic acid molecules encoding such polypeptides and to methods for generation of such polypeptides and nucleic acid molecules. In addition, the invention is directed to compositions comprising the polypeptides, and therapeutic and/or diagnostic uses of these polypeptides.

14 Claims, 10 Drawing Sheets

Figure 1:
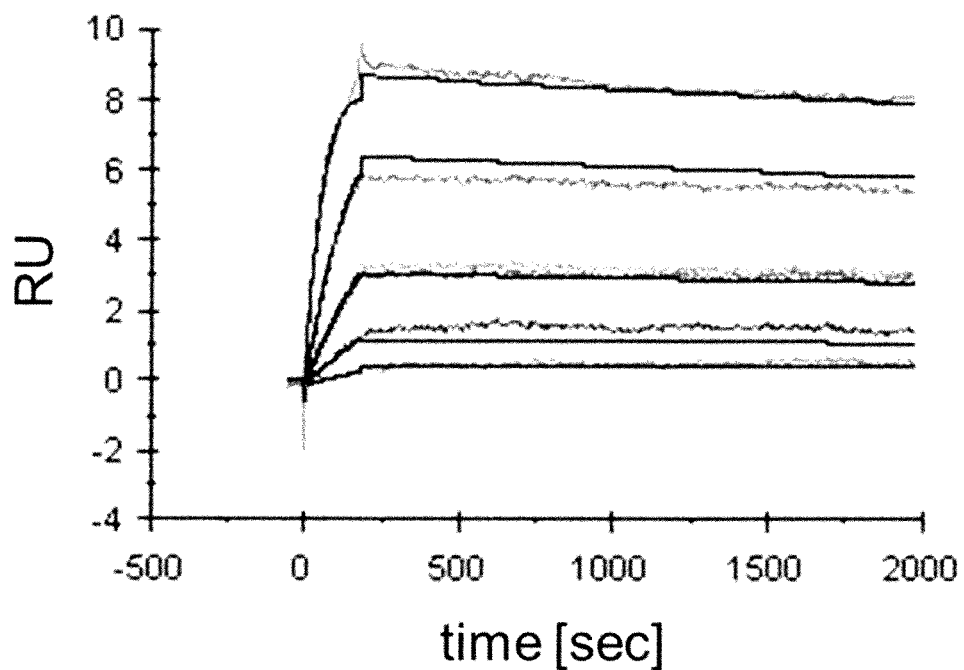

Specification includes a Sequence Listing.

(56) References Cited

FOREIGN PATENT DOCUMENTS

| | | |
|---|---|---|
| EP | 0 330 451 A2 | 8/1989 |
| EP | 0 361 991 A2 | 4/1990 |
| JP | 2005503829 A | 2/2005 |
| JP | 2007-531503 A | 11/2007 |
| JP | 2007284351 A | 11/2007 |
| JP | 2009-540824 A | 11/2009 |
| JP | 2009-545301 A | 12/2009 |
| WO | WO-96/23879 A1 | 8/1996 |
| WO | WO-98/16873 A1 | 4/1998 |
| WO | WO-99/16873 A1 | 4/1999 |
| WO | WO-99/064016 A1 | 12/1999 |
| WO | WO-00/075308 A1 | 12/2000 |
| WO | WO-03/029462 A1 | 4/2003 |
| WO | WO-03/029463 A2 | 4/2003 |
| WO | WO-03/029471 A1 | 4/2003 |
| WO | WO-2005/019254 A1 | 3/2005 |
| WO | WO-2005/019255 A1 | 3/2005 |
| WO | WO-2005/019256 A2 | 3/2005 |
| WO | WO-2006/056464 A2 | 6/2006 |
| WO | WO-2007/038619 A2 | 4/2007 |
| WO | WO-2007/147019 A2 | 12/2007 |
| WO | WO-2007/149032 A1 | 12/2007 |
| WO | WO-2008/015239 A2 | 2/2008 |
| WO | WO-2008/103432 A1 | 8/2008 |
| WO | WO-2009/043933 A1 | 4/2009 |
| WO | WO-2009/052390 A1 | 4/2009 |
| WO | WO-2009/156456 A1 | 12/2009 |
| WO | WO-2012/022742 A1 | 2/2012 |
| WO | WO-2012/065978 A1 | 5/2012 |
| WO | WO-2012/156219 A1 | 11/2012 |
| WO | WO-2013/087660 A1 | 6/2013 |
| WO | WO-2014/076321 A1 | 5/2014 |

OTHER PUBLICATIONS

Altschul et al., Gapped BLAST and PSI-BLAST: a new generation of protein database search programs, Nucleic Acids Res., 25(17):3389-3402 (1997).

Altschul, S. et al., Basic Local Alignment Search Tool; J. Mol. Biol., 215:403-410 (1990).

Amstutz, P. et al.. In vitro display technologies: novel developments and applications, Curr. Opin. Biotechnol., 2001, 12:400-405.

Bachmann, Barbara J., Linkage Map of *Escherichia coli* K-12. Edition 8, Microbial. Rev., Jun. 1990, 54(2):130-197.

Beck, et al.. Nucleotide Sequence and Genome Organisation of Filamentous Bacteriophages f1 and fd, Gene, vol. 16, pp. 35-58, 1981.

Beste, G. et al., Small antibody-like proteins with prescribed ligand specificities derived from the lipocalin fold, Proc. Natl. Acad. Sci. USA, Mar. 1999, 96:1898-1903.

Bittker, J. et al.. Nucleic acid evolution and minimization by nonhomologous random recombination, Nat. Biotechnol., Oct. 2002, 20:1024-1029.

Bos et al., OctoDEX.TM.—Controlled Release of Pharmaceutical Proteins from Hydrogels, Business Briefing: Pharmatech, 2003:1-6.

Breustedt, D. et al., A new crystal form of human tear lipocalin reveals high flexibilty in the loop region and induced fit in the ligand cavity, Acta Crystallographica Section D, Biological Crystallography, D65:1118-1125 (2009).

Breustedt, D. et al.. Comparative ligand-binding analysis often human lipocalins, Biochim. Biophys. Acta, 2006, 1764:161-173.

Breustedt, D. et al., The 1,8-A Crystal Structure of Human Tear Lipocalin Reveals an Extended Branched Cavity with Capacity for Multiple Ligands, The Journal of Biologica Chemistry, 280(1):484-493 (2005).

Broders, O et al., Hyperphage. Improving antibody presentation in phage display, Methods Mol. Biol., 2003, 205:295-302.

Brody et al., Active and Passive Immunotherapy for Neurodegenerative Disorders, Annu. Rev. Neurosci., 2008, 31:175-193.

Bruckdorfer, T., et al., From Production of Peptides in Milligram Amounts for Research to Multi-Tons Quantities for Drugs of the Future, Curr. Pharm. Biotechnol., 2004, 5:29-43.

Bullock, W. et al., XL1-Blue: A High Efficiency Plasmid Transforming recA *Escherichia coli* Strain with Beta-Galactosidase Selection, Biotechniques, 1987, 5(4):376-378.

Bundgaard, J.R. et al., Molecular Cloning and Expression of A cDNA Encode NGAL: A Lipocalin Expressed in Human Neutrophils, Biochemical and Biophysical Research Communications, Aug. 15, 1994, pp. 1468-1475, vol. 202, No. 3, XP002036694.

Carnemolla et al., Phage Antibodies with PAN-Species Recognition of the Oncofoetal Angiogenesis Marker Fibronectin ED-B Domain, Int. J. Cancer, 1996, 68:397-405.

Chan et al., The primary structure of rat $\alpha$ 2$\mu$ globulin-related protein, Nucleic Acids Research, vol. 16, No. 23, pp. 11368, 1988.

Coles, et al., The Solution Structure and Dynamics of Human Neutrophil Gelatinase-associated Lipocalin, J. Mol. Biol., vol. 289, pp. 139-157, 1999.

Dennis, M. et al., Albumin Binding as a General Strategy for Improving the Pharmacokinetics of Proteins, J. Biol. Chem., Sep. 20, 2002, 277(38):35035-35043.

Dodel et al., Immunotherapy for Alzheimer's disease, Lancet Neurology, Apr. 2003, 2:215-220.

Durkin et al., Accession No. EGR88151.1, immunoglobulin G-binding protein G [*Streptococcus dysgalactiae* subsp. Equisimilis SK 1250], Genbank Database, 1 page (Jul. 21, 2011).

Ebbinghaus et al., Diagnostic and Therapeutic Applications of Recombinant Antibodies: Targeting the Extra-Domain B of Fibronectin, A Marker of Tumor Angiogenesis, Curr. Pharm. Des., 2004, 10:1537-1549.

Fitzgerald, Kevin, In Vitro Display Technologies—New Tools for Drug Discovery, Reviews, vol. 5, No. 6, pp. 253-258, Jun. 2000.

Fling, S. and Gregerson, D., Peptide and Protein Molecular Weight Determination by Electrophoresis Using a High-Molarity Tris Buffer System without Urea, Anal. Biochem., 1986, 155:83-88.

Flower, Darren R., The lipocalin protein family: structure and function, Biochem. J., 1996, 318:1-14.

Frank, Ronald, The SPOT-synthesis technique Synthetic Peptide arrays on membrane supports-principles and applications, J. Immunol. Methods, 2002, 267:13-26.

Fuerteges, F. and Abuchowski, A., The Clinical Efficacy of Poly(Ethylene Glycol)-Modified Proteins,: J. Control. Release, 1990, 11:139-148.

Fujii, Ikuo, Beyond Antibodies: Directed evolution of molecular-Targeting peptides in phage-displayed libraries of conformationally constrained Peptides, Drug Delivery System, 26-6: 593-603 (2011).

Fujii, Phage display and beyond antibody—molecular target by antibody molecule, Seikagaku, 2010, vol. 82, No. 8, pp. 710-726, Abstract.

Gaillard, P. et al., Diphtheria toxin receptor-targeted brain drug delivery, International Congress Series., 2005, 1277:185-198.

Gaillard, P. et al., Targeted delivery across the blood-brain barrier, Expert Opin Drug Deliv., 2005, 2(2):299-309.

Gasteiger et al., ExPASy: the proteomics server for in-depth protein knowledge and analysis, Nucleic Acids Res., 2003, 31(13):3784-3788.

Gasymov, O. et al., Ligand Binding Site of Tear Lipocalin: Contribution of a Trigonal Cluster of Charged Residues Probed by 8-Anilino-1-napthalenesulfonic Acid, Biochemistry, 47(5):1414-1424 (2008).

Gasymov, O. et al., The conserved disulfide bond of human tear lipocalin modulates conformation and lipid binding in a ligand selective manner, Biochim Biophys Acta, 1814(5):671-683 (2011).

Goetz, D. et al., Ligand Preference Inferred from the Structure of Neutrophil Gelatinase Associated Lipocalin, Biochemistry, 2000, 39:1935-1941.

Gronwall et al., Selection and characterization of Affibody ligands binding to Alzheimer amyloid $\beta$ peptides, J. Biotechnol., 2007, 128:162-183.

Haass et al., Soluble protein oligomers in neurodegeneration: lessons from the Alzheimer's amyloid $\beta$-peptide, Nat. Rev. Mol. Cell. Biol., Feb. 2007, 8:101-112.

(56) References Cited

OTHER PUBLICATIONS

Hengen, Paul N., Methods and Reagents, Trends Biochem. Sci., vol. 21, pp. 75-76, 1996.

Hoess, Ronald H., Phage Display of Peptides and Protein Domains, Structural Biology, vol. 3, pp. 572-279, 1993.

Hohlbaum et al., Anticalins(R): The lipocalin family as a novel protein scaffold for the development of next-generation immunotherapies; Expert Review of Clinical Immunology, 3(4): 491-501 (Jan. 2007).

Holzfeind, P. et al., Structural Organization of the Gene Encoding the Human Lipocalin Tear Prealbumin and Synthesis of the Recombinant Protein in *Escherichia coli*, Gene, vol. 139, pp. 177-183, 1994.

Hortschansky et al., The aggregation Kinetics of Alzheimer's β-amyloid peptide is controlled by stochastic nucleation, Protein Sci., 2005, 14:1753-1759.

Hoyer, W. et al., Stabilization of a β-hairpin in monomeric Alzheimer's amyloid-β peptide inhibits amyloid formation, Proc. Natl. Acad. Sci. USA, Apr. 1, 2008, 105(13):5099-5104.

International Search Report for PCT/EP2013/074224, dated Apr. 30, 2014.

International Search report issued in Application No. PCT/EP2015/061034 dated Dec. 21, 2015.

Karlsson et al., Kinetic analysis of monoclonal antibody-antigen interactions with a new biosensor based analytical system, J. Immunol. Methods, 1991, 145:229-240.

Kaspar et al., Fibronectin as target for tumor therapy, Int. J. Cancer, 2006, 118:1331-1339.

Khurana et al., Mechanism of thioflavin T binding to amyloid fibrils, J. Struct. Biol., 2005, 151:229-238.

Kim, H. et al., High-Affinity Recognition of Lanthanide(III) Chelate Complexes by a Reprogrammed Human Lipocalin 2, J. Am. Chem. Soc., 2009, 131:3565-3576.

Kjelsden, L. et al., Human Neutrophil Gelatinase-Associated Lipocalin and Homologous Proteins in Rat and Mouse, Biochimica et Biophysica Acta, vol. 1482, pp. 272-283, 2000.

Konig, T. and Skerra, A., Use of an albumin-binding domain for the selective immobilization of recombinant capture antibody fragments on ELISA plates, J. Immunol. Methods, 1998, 218:73-83.

Korean Office Action issued in corresponding application No. 10-2012-7017730 dated Jul. 28, 2018 with English translation.

Kraulis, et al., The Serum Albumin-Binding Domain of Streptococcal Protein G is a Three-Helical Bundle: A Heteronuclear NMR Study, FEBS Letters, vol. 378, pp. 190-194, 1996.

Leahy et al., Crystallization of a Fragment of Human Fibronectin: Introduction of Methionine by Site-Directed Mutagenesis to Allow Phasing via Selenomethionine, Proteins, 1994, 19:48-54.

Lichtlen et al., Antibody-based approaches in Alzheimer's research: safety, pharmacokinetics, metabolism, and analytical tools, J. Neurochem., 2007, 104:859-874.

Lohrengel, B. et al., Expression and Purification of Woodchuck Tumour Necrosis Factor Alpha, Cytokine, vol. 12, No. 6, pp. 573-577, Jun. 2000.

Low, N. et al., Mimicking Somatic Hypermutation: Affinity Maturation of Antibodies Displayed on Bacteriophage Using a Bacterial Mutator Strain, J. Mol. Biol., vol. 260, pp. 359-368, 1996.

Lowman, H.B. Bacteriophage display and discovery of peptides leads for drug development, Annu. Rev. Biophys. Biomol. Struct., 1997, 26:401-424.

Mateo, C. et al., Removal of Amphipathic Epitopes from Genetically Engineered Antibodies: Production of Modified Immunoglobulins with Reduced Immunogenicity, Hybridoma, 2000, 19(6):463-471.

Meidan et al., Emerging Technologies in Transdermal Therapeutics, Am. J. Ther., 2004, 11(4):312-316.

Moretto et al., Conformation-sensitive Antibodies against Alzheimer Amyloid-β by Immunization with a Thioredoxin-constrained B-cell Epitope Peptide, J. Biol. Chem., 2007, 282(15):11436-11445.

Murakami, H. et al., Random insertion and deletion of arbitrary No. of bases for codon-based random mutation of DNAs, Nat. Biotechnol., Jan. 2002, 20:76-81.

National Institutes of Health, European Molecular Biology Laboratory, UniProtKB—Lipocalin-1, downloaded from <https://www.uniprot.org/uniprot/P31025>, 11 pages (2018).

Notice of Reasons for Rejections dated Jan. 20, 2015 issued in Japanese Application No. 2012-542505, with English translation.

Osborn, B. et al., Pharmacokinetic and Pharmacodynamic Studies of a Human Serum Albumin-Interferon-α Fusion Protein in Cynomolgus Monkeys, J. Pharmacol. Exp. Ther., 2002, 303(2):540-548.

Paine et al., The Lipocalin website, Elsevier Science B.V., Biochimica et Biophysica Acta 1482, pp. 351-352, 2000.

Papiz, et al., The Structure of Beta-Lactoglobulin and Its Similarity to Plasma Retinol-Binding Protein, Nature, vol. 324, pp. 383-385, 1986.

Pervaiz, et al., Homology and Structure-Function Correlations Between α1-Acid Glycoprotein and Serum Retinol-Binding Protein and Its Relatives, 1987, The FASEB journal 1.3 (1987): 209-214.

Pieris Presents Data and Reveals Targets for Anticalin® Bispecific PRS-190 at European Antibody Congress, retrieved from https://www.pieris.com/news-and-events/press-releases/detail/304/pieris-presents-data-and-reveals-targets-for-anticalin, in Freising, Germany on Nov. 29, 2012, 4 pages.

Pini et al., Design and Use of a Phage Display Library, J. Biol. Chem., Aug. 21, 1998, 273(34):21769-21776.

Pini, A. et al., Phage Display and Colony Filter Screening for High-Throughput Selection of Antibody Libraries, Comb. Chem. High Throughput Screen., 2002, 5:503-510.

Pujuguet et al., Expression of Fibronectin ED-A+ and ED-B+ Isoforms by Human and Experimental Colorectal Cancer, Am. J. Pathol., Feb. 1996, 148(2):579-592.

Redl, Bernhard, Human tear lipocalin, Biochim. Biophys. Acta, 2000, 1482:241-248.

Roberts, Richard W., Totally In Vitro Protein Selection Using mRNA-Protein Fusions and Ribosome Display, Current Opinion in Chemical Biology, vol. 3, pp. 268-273, 1999.

Rodi, D. and Makowski, L., Phage-display technology—finding a needle in a vast molecular haystack, Curr. Opin. Biotechnol., 1999, 10:87-93.

Schlehuber et al., Anticalins as an alternative to antibody technology; Experl Opinion on Biological Therapy, 5(11): 1453-1462 (Jan. 2005).

Schlehuber, S. and Skerra, A. et al., Duocalins, engineered ligand-binding proteins with dual specificity derived from the lipocalin fold, Biol. Chem., Sep. 2001, 382:1335-1342.

Schlehuber, S. and Skerra, A., Lipocalins in drug discovery: from natural ligand-binding proteins to 'anticalins', DDT, 10(1): 23-33 (2005).

Schlehuber, S. et al., A Novel Type of Receptor Protein, Based on the Lipocalin Scaffold, with Specificity for Digoxigenin, J. Mol. Biol., 2000, 297:1105-1120.

Schliemann et al., Antibody-based targeting of the tumor vasculature, Biochim. Biophys. Acta, 2007, 1776:175-192.

Schmidt et al., The Strep-tag system for one-step purification and high-affinity detection of capturing of proteins, Nat. Protoc., 2007, 2(6):1528-1535.

Schmidt, T. et al., Molecular Interaction Between the Strep-tag Affinity Peptide and its Cognate Target, Streptavidin, J. Mol. Biol., 1996, 255:753-766.

Schoepfer, Ralf, The pRSET Family of T7 Promoter Expression Vectors for *Escherichia coli*, Gene, vol. 124, pp. 83-85, 1993.

Schonfeld, D et al. An engineered lipocalin specific for CTLA-4 reveals a combining site with structural and conformational features similar to antibodies, PNAS, 106(20): 8198-8203 (2009).

Skerra et al., 'Anticalins': a new class of engineered ligand-binding proteins with antibody-like properties, Reviews in Molecular Biotechnology, 2001,74:257-275.

Skerra, A. et al., Accession No. AFR78283.2, immunoglobulin heavy chain, partial [*Homo sapiens*], GenBank Database, 1 page (Feb. 3, 2014).

Skerra, A., Engineered protein scaffolds for molecular recognition, J. Mol. Recognit., 2000; 13:167-187.

(56) References Cited

OTHER PUBLICATIONS

Skerra, A., et al., Lipocalins as a scaffold, Elsevier Science B.V., Biochimica et Biophysica Acta 1482, pp. 337-350, 2000.
Skerra, Alternative binding proteins: Anticalins—harnessing the structural plasticity of the lipocalin ligand pocket to engineer novel binding activities; FEBS Journal, 275(11): 2677-2683 (Jun. 2008).
Skerra, Anticalins as alternative binding proteins for therapeutic use; Current Opinion in Molecular Therapeutics, 9(4): 336-344 (Aug. 2007).
Skerra, Arne, Use of the tetracycline promoter for the tightly regulated production of a murine antibody fragment in *Escherichia coli*, Gene, 1994, 151:131-135.
Skerra, et al., Filter Screening of Antibody Fab Fragments Secreted From Individual Bacterial Colonies: Specific Detection of Antigen Binding with a Two-Membrane System, Anal. Biochem., vol. 196, pp. 151-155, 1991.
Stoesz, S. et al., Overexpression of neu-related lipocalin (NRL) in neu-initiated but not ras or chemically initiated rat mammary carcinomas, Oncogene (1995), 11, pp. 2233-2241.
Studier, F.W., and Moffatt, B.A., Use of Bacteriophage T7 RNA Polymerase to Direct Selective High-level Expression of Cloned Genes, J. Mol. Biol., 1986, 189:113-130.
Tartof et al., Improved Media for Growing Plasmid and Cosmid Clones, Focus, Bethesda Research Laboratory, 1987, 9(2):12.
Tulasne, D. et al., C-Terminal Peptide of Thrombospondin-1 Includes Platelet Aggregation Through the Fc Receptor γ-Chain-Associated Signaling Pathway and by Agglutination, Blood, vol. 98, No. 12, pp. 3346-3352, Dec. 1, 2001.
UNIPROT Database—Signal peptide, retrieved from <https://www.uniprot.org/help/signal>, 2 pages (retrieved on Aug. 27, 2019).
Vajo, Z. and Duckworth, W., Genetically Engineered Insulin Analogs: Diabetes in the New Millennium, Pharmacol. Rev., 2000, 52(1):1-9.
Venturi, M. et al., High Level Production of Functional Antibody Fab Fragments in an Oxidizing Bacterial Cytoplasm, J. Mol. Biol., 2002, 315:1-8.
Virnekas et al., Trinucleotide phosphoramidites: ideal reagents for the synthesis of mixed oligonucleotides for random mutagenesis, Nucleic Acids Res, 1994, 22(25):5600-5607.
Vogt, M. and Skerra, A., Construction of an Artificial Receptor Protein ("Anticalin") Based on the Human Apolipoprotein D, ChemBioChem, 5:191-199 (2004).
Voss, et al., Mutagenesis of a Flexible Loop in Streptavidin Leads to Higher Affinity for the Strep-Tag II Peptide and Improved Performance in Recombinant Protein Purification, Protein Engineering, vol. 10, No. 8, pp. 975-982, 1997.
Wang et al., Expanding the Genetic Code of *Escherichia coli*, Science, Apr. 20, 2001, 292:498-500.
Wang et al., Expanding the genetic code, Chem. Comm., 2002, 1:1-11.
Wang, A. M. et al., Molecular Cloning of the Complementary DNA for Human Tumor Necrosis Factor, Science, vol. 228, pp. 149-154, 1985 (Abstract).
Weiss et al., Anticalins versus antibodies: made-to-order binding proteins for small molecules; Chemistry and Biology, 7(8): R177-R184 (Aug. 2000).
Wells, J. et al., Rapid Evolution of Peptide and Protein Binding Properties In Vitro, Current Opinion in Structural Biology, vol. 2, pp. 597-604, 1992.
Wilson, D. et al., The use of mRNA display to select high-affinity protein-binding peptides, Proc. Natl. Acad. Sci. USA, Mar. 27, 2001, 98(7):3750-3755.
Yanisch-Perron, C. et al., Improved M13 phage cloning vectors and host strains: nucleotide sequences of the M13mp18 and pUC19 vectors, Gene, 1985, 33:103-119.
Zaccolo, M. et al., An Approach to Random Mutagenesis of DNA Using Mixtures of Triphosphate Derivatives of Nucleoside Analogues, J. Mal. Biol., 1996, 255:589-603.
Zardi, L. et al., Transformed human cells produce a new fibronectin isoform by preferential alternative splicing of a previously unobserved exon, EMBO J, 6(8):2337-42 (1987).
Gebauer, M. et al., Combinatorial Design of an Anticalin Directed against the Extra-Domain B for the Specific Targeting of Oncofetal Fibronectin, J. Mol. Biol., 425: 780-802 (2013).
Wells, James A., Additivity of Mutual Effects in Proteins, Biochemistry, Sep. 18, 1990, vol. 29, No. 37, pp. 8509-8517.

\* cited by examiner

SPECIFIC-BINDING POLYPEPTIDES AND USES THEREOF

CROSS-REFERENCE TO RELATED APPLICATIONS

This application is a divisional of U.S. application Ser. No. 15/312,094, filed Nov. 17, 2016, which is a National Stage application of PCT/EP2015/061034, filed May 20, 2015, which claims priority from European Application No. 14169488.5, filed May 22, 2014, each of which are hereby incorporated by reference in their entireties.

SEQUENCE LISTING

The instant application contains a Sequence Listing, which has been submitted in ASCII format via EFS-WEB and is hereby incorporated by reference in its entirety. Said ASCII copy, created on Aug. 4, 2020, is named "2013101-0117_SL.txt" and is 5.67 MB in size.

I. BACKGROUND

Muteins of various lipocalins are a rapidly expanding class of therapeutics. Indeed, lipocalin muteins can be constructed to exhibit a high affinity and specificity against a target that is different than a natural ligand of wild type lipocalins (e.g., WO 99/16873, WO 00/75308, WO 03/029463, WO 03/029471 and WO 05/19256), such as Interleukin-17A or Interleukin-23.

A. Interleukin-17A

Interleukin-17A (IL-17A, synonymous with IL-17) is a cytokine produced from the Th17 lineage of T cells. IL-17 was originally designated "CTL-associated antigen 8" (CTLA-8) (Rouvier et al., J. Immunol, 150 5445-5556 (1993); Yao et al., Immunity, 3: 811-821 (1995)). The human equivalent of CTLA-8 was later cloned and designated "IL-17" (Yao et al., J. Immunol, 155(12): 5483-5486 (1995); Fossiez et al., J. Exp. Med., 183(6): 2593-2603 (1996)).

Human IL-17A (CTLA-8, further named as IL-17, Swiss Prot Q16552) is a glycoprotein with a Mr of 17,000 daltons (Spriggs et al., J. Clin. Immunol, 17: 366-369 (1997)). IL-17A may exist as either a homodimer IL-17 A/A or as a heterodimer complexed with the homolog IL-17F to form heterodimeric IL-17 A/F. IL-17F (IL-24, ML-1) shares a 55% amino acid identity with IL-17A. IL-17A and IL-17F also share the same receptor (IL-17RA), which is expressed on a wide variety of cells including vascular endothelial cells, peripheral T cells, B cells, fibroblast, lung cells, myelomonocytic cells, and marrow stromal cells (Kolls et al., Immunity, 21: 467-476 (2004); Kawaguchi et al., J. Allergy Clin. Immunol, 114(6): 1267-1273 (2004); Moseley et al., Cytokine Growth Factor Rev., 14(2): 155-174 (2003)). Additional IL-17 homologs have been identified (IL-17B, IL-17C, IL-17D, and IL-17E). These other family members share less than 30% amino acid identity with IL-17A (Kolls et al., 2004).

IL-17A is mainly expressed by Th17 cells and is present at elevated levels in synovial fluid of patients with rheumatoid arthritis (RA) and has been shown to be involved in early RA development. IL-17A is also over-expressed in the cerebrospinal fluid of multiple sclerosis (MS) patients. In addition, IL-17 is an inducer of TNF-α and IL-1, the latter being mainly responsible for bone erosion and the very painful consequences for affected patients (Lubberts E. (2008) Cytokine, 41, p. 84-91). Furthermore, inappropriate or excessive production of IL-17A is associated with the pathology of various other diseases and disorders, such as osteoarthritis, loosening of bone implants, acute transplant rejection (Antonysamy et al., (1999) J. Immunol, 162, p. 577-584; van Kooten et al. (1998) J. Am. Soc. Nephrol., 9, p. 1526-1534), septicemia, septic or endotoxic shock, allergies, asthma (Molet et al., (2001) J. Allergy Clin. Immunol., 108, p. 430-438), bone loss, psoriasis (Teunissen et al. (1998) J. Invest. Dermatol, 111, p. 645-649), ischemia, systemic sclerosis (Kurasawa et al., (2000) Arthritis Rheum., 43, p. 2455-2463), stroke, and other inflammatory disorders.

Although a variety of inhibitors of IL-17A have been described, since the discovery of this critical proinflammatory cytokine, current approaches are not optimal, such as the necessity of complex mammalian cell production systems, a dependency on disulfide bond stability, the tendency of some antibody fragments to aggregate, limited solubility and last but not least, they may elicit undesired immune responses even when humanized. There remains a need, therefore, to develop proteins such as lipocalin muteins with binding-affinity for IL-17A.

B. Interleukin-23

Interleukin-23 (also known as IL-23) is a heterodimeric cytokine comprised of two subunits, i.e., p19 and p40 (B. Oppmann et al, Immunity 13, 715 (2000)). The p19 (Swiss Prot Q9NPF7, herein referred to interchangeably as "IL-23p19") subunit is structurally related to IL-6, granulocyte-colony stimulating factor (G-CSF), and the p35 subunit of IL-12. IL-23 mediates signaling by binding to a heterodimeric receptor, comprised of IL-23R and IL-12beta1. The IL-12beta1 subunit is shared by the IL-12 receptor, which is composed of IL-12beta1 and IL-12beta2. Transgenic p19 mice have been recently described to display profound systemic inflammation and neutrophilia (M. T. Wiekowski et al, J Immunol 166, 7563 (2001)).

Human IL-23 has been reported to promote the proliferation of T cells, in particular memory T cells and can contribute to the differentiation and/or maintenance of Th17 cells (D. M. Frucht, Sci STKE 2002 Jan. 8; 2002 (114):PE1).

Although a variety of selective inhibitors of IL-23 (via binding to the p19 subunit) have been described, since the discovery of this critical heterodimeric cytokine, these current approaches still have a number of serious drawbacks, such as the necessity of complex mammalian cell production systems, a dependency on disulfide bond stability, the tendency of some antibody fragments to aggregate, limited solubility and last but not least, they may elicit undesired immune responses even when humanized. There is an unmet need to, therefore, to develop proteins such as lipocalin muteins with binding-affinity for IL-23.

II. DEFINITIONS

The following list defines terms, phrases, and abbreviations used throughout the instant specification. All terms listed and defined herein are intended to encompass all grammatical forms.

As used herein, "IL-17A" (including IL-17 A/A as well as IL-17A in complex with IL-17F, also termed as IL-17 A/F) means a full-length protein defined by Swiss Prot Q16552, a fragment thereof, or a variant thereof.

As used herein, "IL-23p19" means a full-length protein defined by Swiss Prot Q9NPF7, a fragment thereof, or a variant thereof.

As used herein, "detectable affinity" means the ability to bind to a selected target with an affinity constant of generally at least about $10^{-5}$ M. Lower affinities are generally no longer measurable with common methods such as ELISA and therefore of secondary importance. For example, binding affinities of lipocalin muteins according to the disclosure may in some embodiments be of a $K_D$ below 800 nM, in some embodiments be of a $K_D$ below 30 nM and in some embodiments about 50 picomolar (pM) or below.

As used herein, "binding affinity" of a protein of the disclosure (e.g. a mutein of a lipocalin) or a fusion protein thereof to a selected target (in the present case, IL-17A or IL-23p19), can be measured (and thereby KD values of a mutein-ligand complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art and examples thereof are also detailed below.

It is also noted that the complex formation between the respective binder and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective binder and its target/ligand) may vary within a certain experimental range, depending on the method and experimental setup that is used for determining the affinity of a particular lipocalin mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA."

As used herein, a "mutein," a "mutated" entity (whether protein or nucleic acid), or "mutant" refers to the exchange, deletion, or insertion of one or more nucleotides or amino acids, compared to the naturally occurring (wild-type) nucleic acid or protein "reference" scaffold.

The term "fragment" as used herein in connection with the muteins of the disclosure relates to proteins or peptides derived from full-length mature human tear lipocalin that are N-terminally and/or C-terminally shortened, i.e. lacking at least one of the N-terminal and/or C-terminal amino acids. Such fragments may include at least 10, more such as 20 or 30 or more consecutive amino acids of the primary sequence of the mature lipocalin and are usually detectable in an immunoassay of the mature lipocalin. Said term also includes fragments of a mutein and variants as described herein. Lipocalin muteins of the present invention, fragments or variants thereof preferably retain the function of binding to IL-17A and/or IL23p19 as described herein.

In general, the term "fragment", as used herein with respect to the corresponding protein ligand IL-17A (including IL-17 A/A and IL-17 A/F) or IL-23p19 of a lipocalin mutein of the disclosure or of the combination according to the disclosure or of a fusion protein described herein, relates to N-terminally and/or C-terminally shortened protein or peptide ligands, which retain the capability of the full length ligand to be recognized and/or bound by a mutein according to the disclosure.

The term "mutagenesis" as used herein means that the experimental conditions are chosen such that the amino acid naturally occurring at a given sequence position of the mature lipocalin can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in the disclosure. In one exemplary embodiment of the disclosure, an insertion of several mutations may be introduced into the loop AB of the chosen lipocalin scaffold (cf. International Patent Application WO 2005/019256 which is incorporated by reference its entirety herein).

The term "random mutagenesis" means that no predetermined single amino acid (mutation) is present at a certain sequence position but that at least two amino acids can be incorporated with a certain probability at a predefined sequence position during mutagenesis.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Identity is measured by dividing the number of identical residues by the total number of residues and multiplying the product by 100.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any lipocalin mutein of the disclosure).

The percentage of sequence homology or sequence identity can, for example, be determined herein using the program BLASTP, version blastp 2.2.5 (Nov. 16, 2002; cf. Altschul, S. F. et al. (1997) *Nucl. Acids Res.* 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

Specifically, in order to determine whether an amino acid residue of the amino acid sequence of a lipocalin (mutein) different from a wild-type lipocalin corresponds to a certain position in the amino acid sequence of a wild-type lipocalin, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a wild-type lipocalin can serve as "subject sequence" or "reference sequence", while the amino acid sequence of a lipocalin different from the wild-type lipocalin described herein serves as "query sequence".

The terms "reference sequence" and "wild type sequence" are used interchangeably herein.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. The term "variant", as used herein with respect to the corresponding protein ligand IL-17A (including IL-17 A/A and IL-17 A/F) or IL-23p19 of a lipocalin mutein of the disclosure or of the combination according to the disclosure or of a fusion protein described herein, relates to an IL-17 protein or fragment thereof or IL-23 protein or fragment thereof, respectively, that has one or more such as 1, 2, 3, 4, 5, 6, 7, 8, 9, 10, 12, 14, 16, 18, 20, 22, 24, 26, 28, 30, 40, 50, 60, 70, 80 or more amino acid substitutions, deletions and/or insertions in comparison to a wild-type IL-17A or IL-23p19 protein, respectively, such as an IL-17A or IL-23p19 reference protein as deposited with SwissProt as described herein. AN IL-17A or IL-23p19 variant, respectively, has preferably an amino acid identity of at least 50%, 60%, 70%, 80%, 85%, 90% or 95% with a wild-type IL-17A or IL-23p19 protein, respectively, such as an IL-17A or IL-23p19 reference protein as deposited with SwissProt as described herein.

By a "native sequence" lipocalin is meant a lipocalin that has the same amino acid sequence as the corresponding polypeptide derived from nature. Thus, a native sequence lipocalin can have the amino acid sequence of the respective naturally-occurring lipocalin from any organism, in particular a mammal. Such native sequence polypeptide can be isolated from nature or can be produced by recombinant or synthetic means. The term "native sequence" polypeptide specifically encompasses naturally-occurring truncated or secreted forms of the lipocalin, naturally-occurring variant forms such as alternatively spliced forms and naturally-occurring allelic variants of the lipocalin. A polypeptide "variant" means a biologically active polypeptide having at least about 50%, 60%, 70%, 80% or at least about 85% amino acid sequence identity with the native sequence polypeptide. Such variants include, for instance, polypeptides in which one or more amino acid residues are added or deleted at the N- or C-terminus of the polypeptide. Generally a variant has at least about 70%, including at least about 80%, such as at least about 85% amino acid sequence identity, including at least about 90% amino acid sequence identity or at least about 95% amino acid sequence identity with the native sequence polypeptide. As an illustrative example, the first 4 N-terminal amino acid residues (HHLA) and the last 2 C-terminal amino acid residues (Ser, Asp) can be deleted, for example, in a tear lipocalin (Tlc) mutein of the disclosure without affecting the biological function of the protein, e.g. SEQ ID NO: 1.

The term "position" when used in accordance with the disclosure means the position of either an amino acid within an amino acid sequence depicted herein or the position of a nucleotide within a nucleic acid sequence depicted herein. To understand the term "correspond" or "corresponding" as used herein in the context of the amino acid sequence positions of one or more lipocalin muteins, a corresponding position is not only determined by the number of the preceding nucleotides/amino acids. Accordingly, the position of a given amino acid in accordance with the disclosure which may be substituted may vary due to deletion or addition of amino acids elsewhere in a (mutant or wild-type) lipocalin. Similarly, the position of a given nucleotide in accordance with the present disclosure which may be substituted may vary due to deletions or additional nucleotides elsewhere in a mutein or wild type lipocalin 5-untranslated region (UTR) including the promoter and/or any other regulatory sequences or gene (including exons and introns).

Thus, for a corresponding position in accordance with the disclosure, it is preferably to be understood that the positions of nucleotides/amino acids may differ in the indicated number than similar neighbouring nucleotides/amino acids, but said neighbouring nucleotides/amino acids, which may be exchanged, deleted, or added, are also comprised by the one or more corresponding positions.

In addition, for a corresponding position in a lipocalin mutein based on a reference scaffold in accordance with the disclosure, it is preferably to be understood that the positions of nucleotides/amino acids are structurally corresponding to the positions elsewhere in a (mutant or wild-type) lipocalin, even if they may differ in the indicated number, as appreciated by the skilled in light of the highly-conserved overall folding pattern among lipocalins.

The term "albumin" includes all mammal albumins such as human serum albumin or bovine serum albumin or rat serum albumin.

The term "organic molecule" or "small organic molecule" as used herein for the non-natural target denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

The word "detect", "detection", "detectable" or "detecting" as used herein is understood both on a quantitative and a qualitative level, as well as a combination thereof. It thus includes quantitative, semi-quantitative and qualitative measurements of a molecule of interest.

A "subject" is a vertebrate, preferably a mammal, more preferably a human. The term "mammal" is used herein to refer to any animal classified as a mammal, including, without limitation, humans, domestic and farm animals, and zoo, sports, or pet animals, such as sheep, dogs, horses, cats, cows, rats, pigs, apes such as cynomolgous monkeys and etc., to name only a few illustrative examples. Preferably, the mammal herein is human.

An "effective amount" is an amount sufficient to effect beneficial or desired results. An effective amount can be administered in one or more administrations.

A "sample" is defined as a biological sample taken from any subject. Biological samples include, but are not limited to, blood, serum, urine, feces, semen, or tissue.

A "fusion polypeptide" as described herein comprises at least two subunits, wherein one subunit has binding specificity for IL-17A or has binding specificity for IL-23p19. Within the fusion polypeptide, these subunits may be linked by covalent or non-covalent linkage. Preferably, the fusion polypeptide is a translational fusion between the two or more subunits. The translational fusion may be generated by genetically engineering the coding sequence for one subunit in frame with the coding sequence of a further subunit. Both subunits may be interspersed by a nucleotide sequence encoding a linker. However, the subunits of a fusion polypeptide of the present disclosure may also be linked by a chemical linker.

A "linker" that may be comprised by a fusion polypeptide of the present disclosure links two or more subunits of a fusion polypeptide as described herein. The linkage can be covalent or non-covalent. A preferred covalent linkage is via a peptide bond, such as a peptide bond between amino acids. Accordingly, in a preferred embodiment said linker comprises of one or more amino acids, such as 1, 2, 3, 4, 5, 6, 7, 8, 9, 10, 11, 12, 13, 14, 15, 16, 17, 18, 19, 20 or more amino acids. Preferred linkers are described herein. Other preferred linkers are chemical linkers.

III. DESCRIPTIONS OF FIGURES

FIG. 1: provides a typical measurement of on-rate and off-rate by surface plasmon resonance for the interaction of the lipocalin mutein of SEQ ID NO: 1 with human IL-17A. IL-17A was immobilized on a sensor chip using standard amine chemistry, and the lipocalin mutein of SEQ ID NO: 1 was employed as the soluble analyte which was flowed across the chip surface. The resulting dissociation constant ($K_D$) is 0.8 nM.

Figure 2:
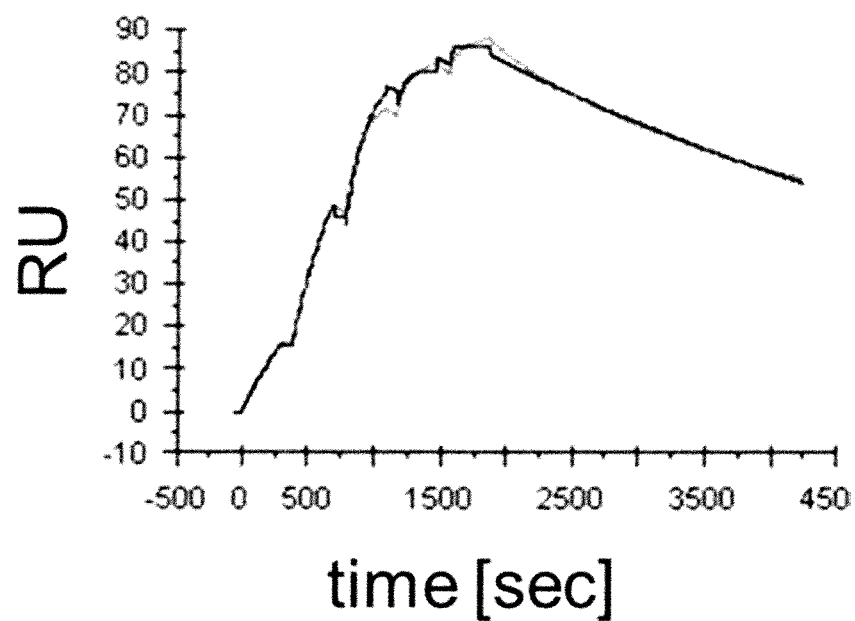

FIG. 2: provides a typical measurement of on-rate and off-rate by surface plasmon resonance for the interaction of the lipocalin mutein of SEQ ID NO: 1 with human IL-17 A/F. Biotinylated SEQ ID NO: 1 was captured on a sensor chip using a dedicated experimental kit, and human IL-17 A/F was employed as the soluble analyte which was flowed across the chip surface. The resulting dissociation constant ($K_D$) is 100 pM.

Figure 3:
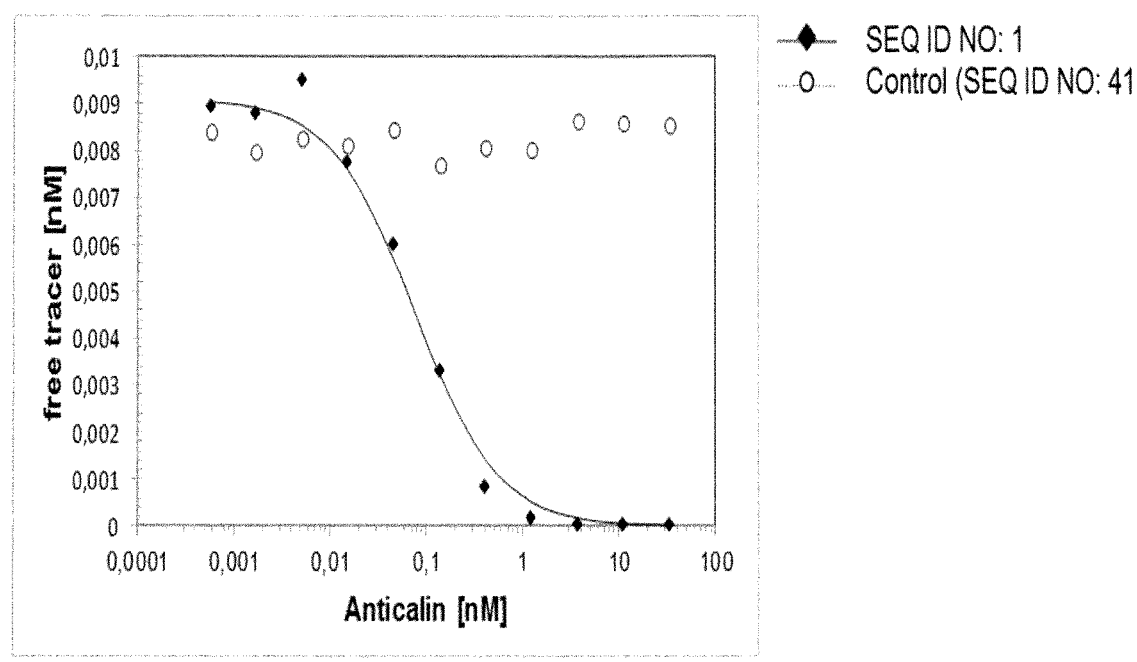

FIG. 3: demonstrates that the lipocalin mutein of SEQ ID NO: 1 is capable of blocking the interaction between hIL-17A and its receptor hIL-17RA with an IC50 of 75 pM. Biotinylated hIL-17A was pre-incubated with variable concentrations of the lipocalin mutein of SEQ ID NO: 1 and non-neutralized hIL-17A was quantified on an ELISA plate with immobilized soluble hIL-17RA. The negative control SEQ ID NO: 41 had no competitive effect. The data were fitted with a single-site binding model.

Figure 4:
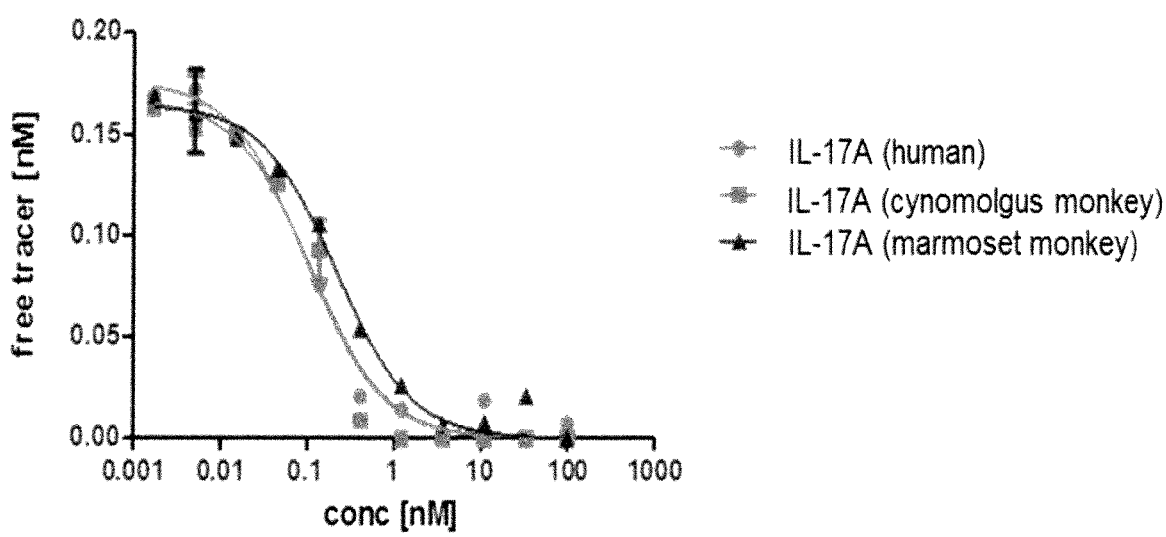

FIG. 4: shows the crossreactivity profile of the lipocalin mutein of SEQ ID NO: 1 as measured in a competition ELISA format. Full crossreactivity with cynomolgus monkey IL-17A and marmoset IL-17A is evident from nearly identical IC50 values compared to hIL-17A. The data were fitted with a single-site binding model.

Figure 5:
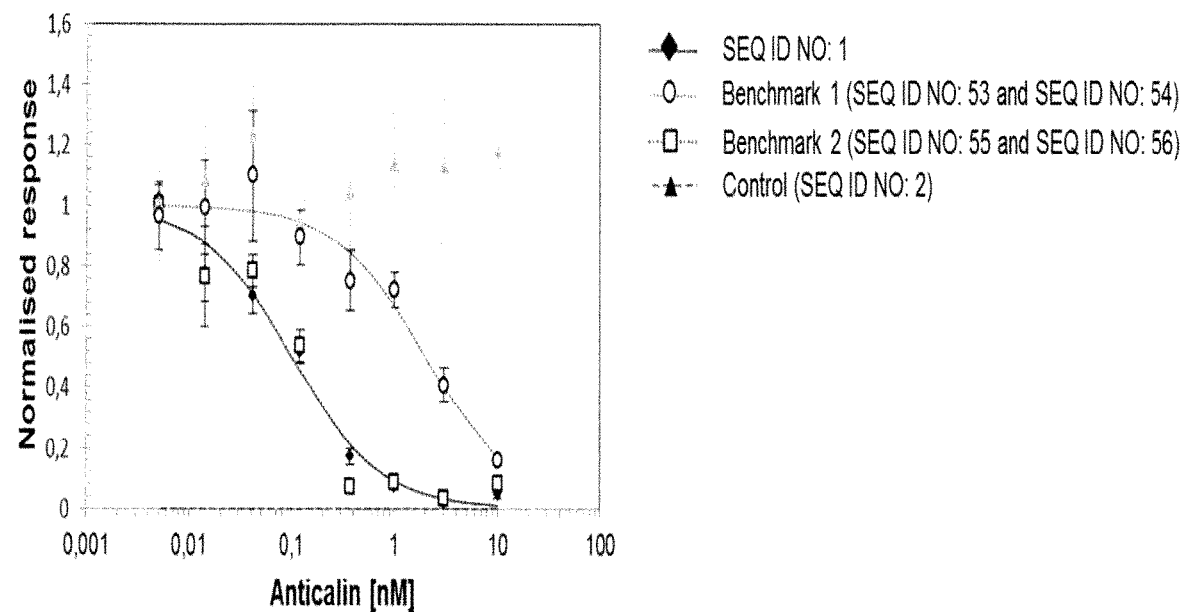

FIG. 5: illustrates that the lipocalin mutein of SEQ ID NO: 1 is highly effective in blocking hIL-17A binding to its receptor hIL-17RA in a cell-based assay. The assay is based on hIL-17A-induced secretion of G-CSF in U87-MG cells. Cells were incubated with a fixed concentration of hIL-17A and titrated with the lipocalin mutein of SEQ ID NO: 1 or, for comparison, benchmark antibody 1 (heavy chain SEQ ID NO: 53, light chain SEQ ID NO: 54), benchmark antibody 2 (heavy chain SEQ ID NO: 55, light chain SEQ ID NO: 56) and SEQ ID NO: 2 as a negative control. Plotted is the concentration of G-CSF in arbitrary units as measured by MSD (Meso Scale Discovery®, hereafter "MSD") against the concentration of lipocalin muteins or antibody molecules. The resulting average IC50 value for the lipocalin mutein of SEQ ID NO: 1 was 0.13 nM (0.17 nM in the first experiment, 0.10 nM in the repeat experiment), which was significantly more potent that benchmark 1, which exhibited an average IC50=2.33 (2.65/2.01) nM, and in a similar range compared to benchmark 2, with an average IC50=0.12 (0.14/0.10) nM. The negative control SEQ ID NO: 2 had no effect on IL-17A-induced G-CSF production of the cells. Binding of SEQ ID NO: 1 or benchmark antibody molecules to IL-17A blocks IL-17A's binding to cell-surface IL-17RA and, thus, prevents induction of G-CSF secretion. The data were fitted with a single-site binding model, assuming equal G-CSF concentration plateaus for all molecules.

Figure 6:
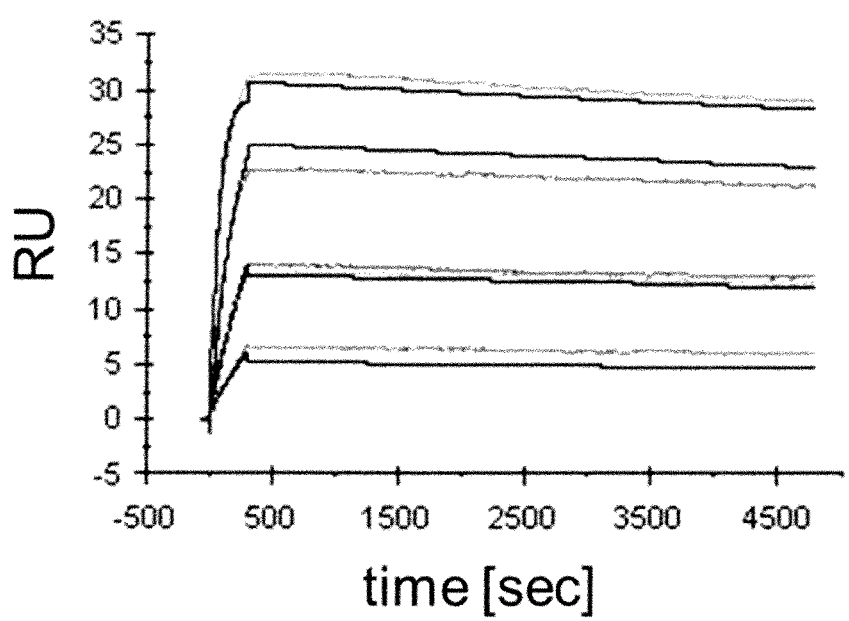

FIG. 6: provides a typical measurement of on-rate and off-rate by surface plasmon resonance for the lipocalin mutein of SEQ ID NO: 2 interacting with human IL-23. The average dissocation constant determined in three replicate experiments amounted to $K_D$=0.35±0.20 nM.

Figure 7:
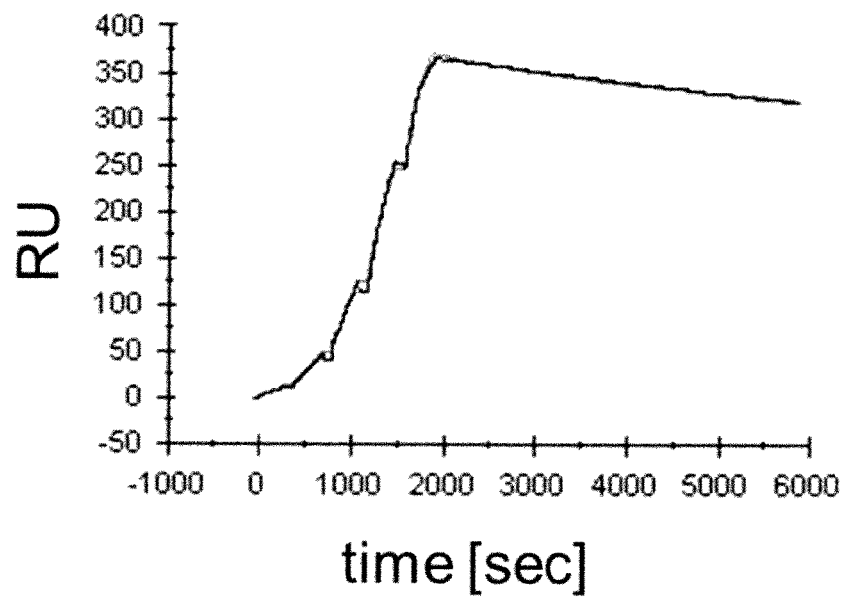

FIG. 7: provides a typical measurement of on-rate and off-rate by surface plasmon resonance for the interaction of the lipocalin mutein of SEQ ID NO: 2 with human IL-23. Biotinylated SEQ ID NO: 2 was captured on a sensor chip using a dedicated experimental kit, and IL-23 was employed as the soluble analyte which was flowed across the chip surface. The resulting dissociation constant ($K_D$) is 2.9 nM. Note that high, nonphysiological concentrations of NaCl had to be employed to facilitate carrying out the assay. The result is therefore not representative of the affinity of SEQ ID NO: 2 to IL-23 under physiological conditions. The utility of the assay lies in its ability to allow comparisons of the affinity of SEQ ID NO: 2 and fusion proteins containing this mutein (see Example 11 and Table 1).

Figure 8:
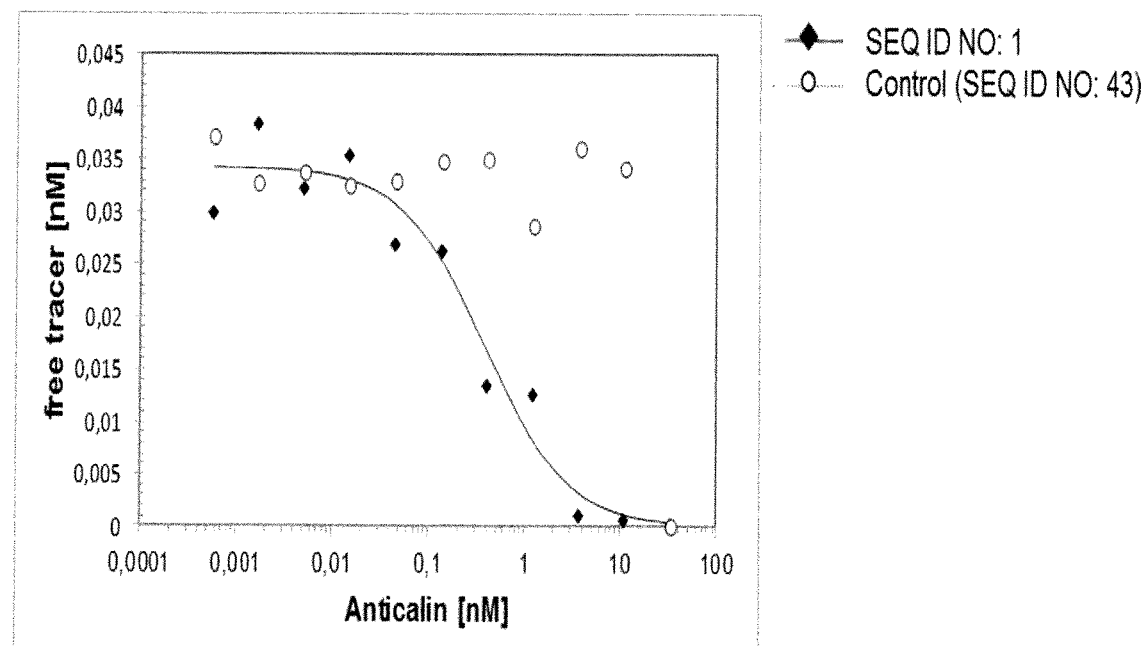

FIG. 8: demonstrates that the lipocalin mutein of SEQ ID NO: 2 is capable of blocking the interaction between hIL-23 and its receptor hIL-23R with an IC50 of 0.54 nM. Biotinylated hIL-23 was pre-incubated with variable concentrations of the lipocalin mutein of SEQ ID NO: 2 and non-neutralized hIL-23 was quantified on an ELISA plate with immobilized soluble hIL-23R. The negative control SEQ ID: 43 has no competitive effect. The data were fitted with a single-site binding model.

Figure 9:
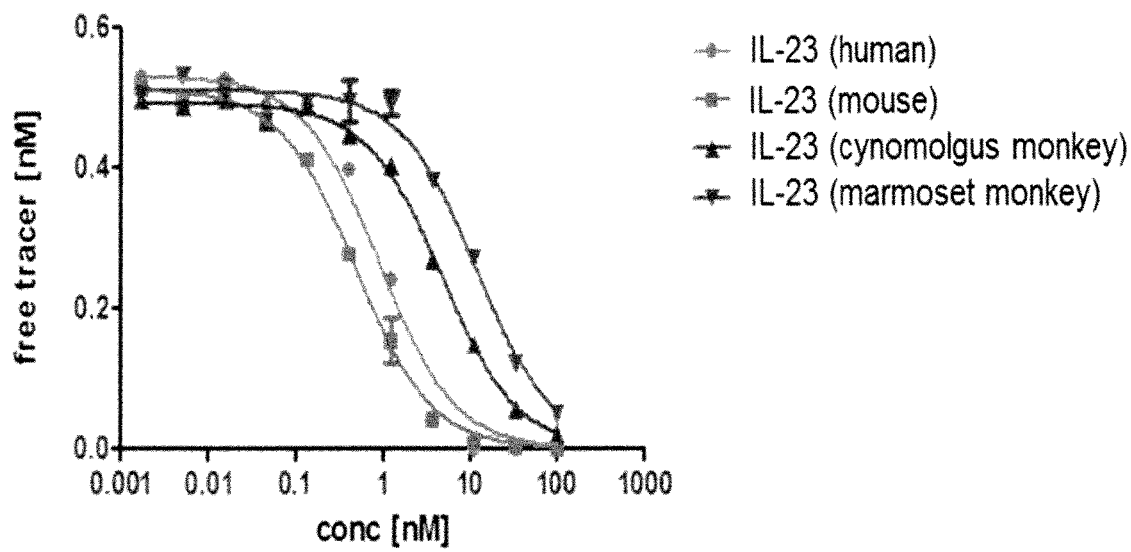

FIG. 9: shows the crossreactivity profile and specificity of the lipocalin mutein of SEQ ID NO: 2 as measured in a competition ELISA format. The lipocalin mutein of SEQ ID NO: 2 is fully crossreactive with human and mouse IL-23, and displays a somewhat reduced affinity towards cynomolgus monkey and marmoset IL-23. The data were fitted with a single-site binding model.

Figure 10:
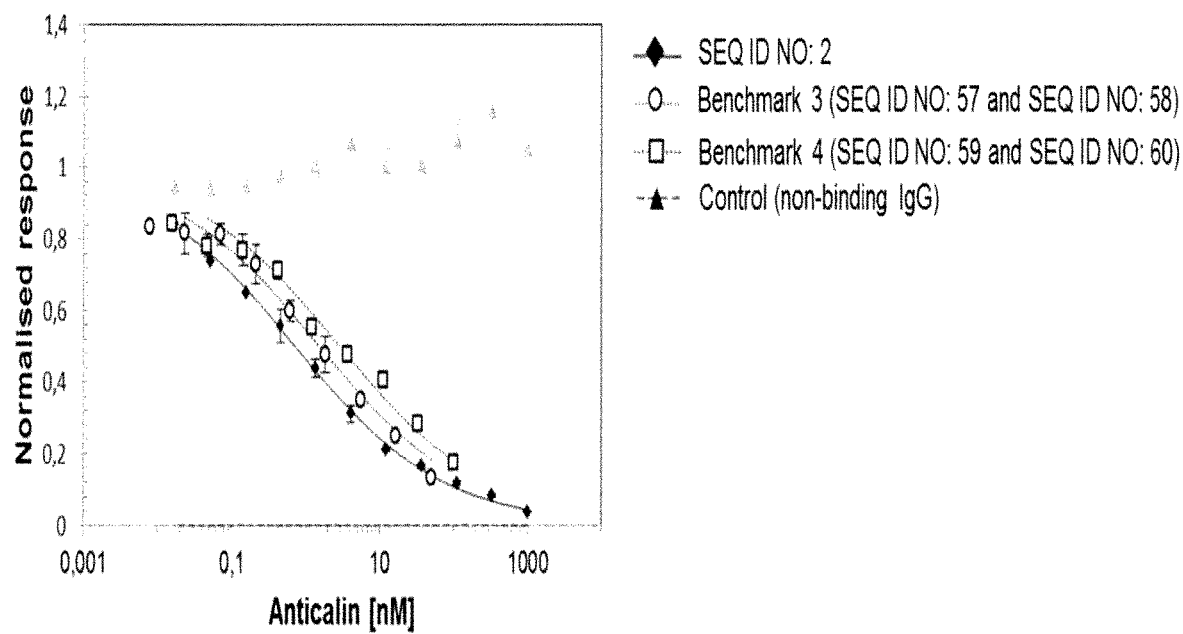

FIG. 10: demonstrates that the lipocalin mutein of SEQ ID NO: 2 is capable of blocking the biological activity of hIL-23 in a cell-based proliferation assay. In the assay, SEQ ID NO: 2, an IgG isotype negative control and two benchmark antibodies (benchmark 3: heavy chain, SEQ ID NO: 57 and, light chain, SEQ ID NO: 58; benchmark 4: heavy chain, SEQ ID NO: 59 and light chain, SEQ ID NO: 60) were preincubated with hIL-23 and subsequently added to Ba/F3 cells transfected with hIL-23R and hIL-12Rβ1. The transfected Ba/F3 cells proliferate in response to human IL-23.

The experiment shows that this biological activity is blocked by SEQ ID NO: 2 and the benchmark antibodies 3 and 4 with EC50 values of 1.2 nM (1.7/0.7), 3.0 nM (3.1/2.9), 1.2 nM (0.8/1.5), respectively. The negative control had no effect on cell proliferation. The data were fitted with a sigmoidal dose-response model.

Figure 11:
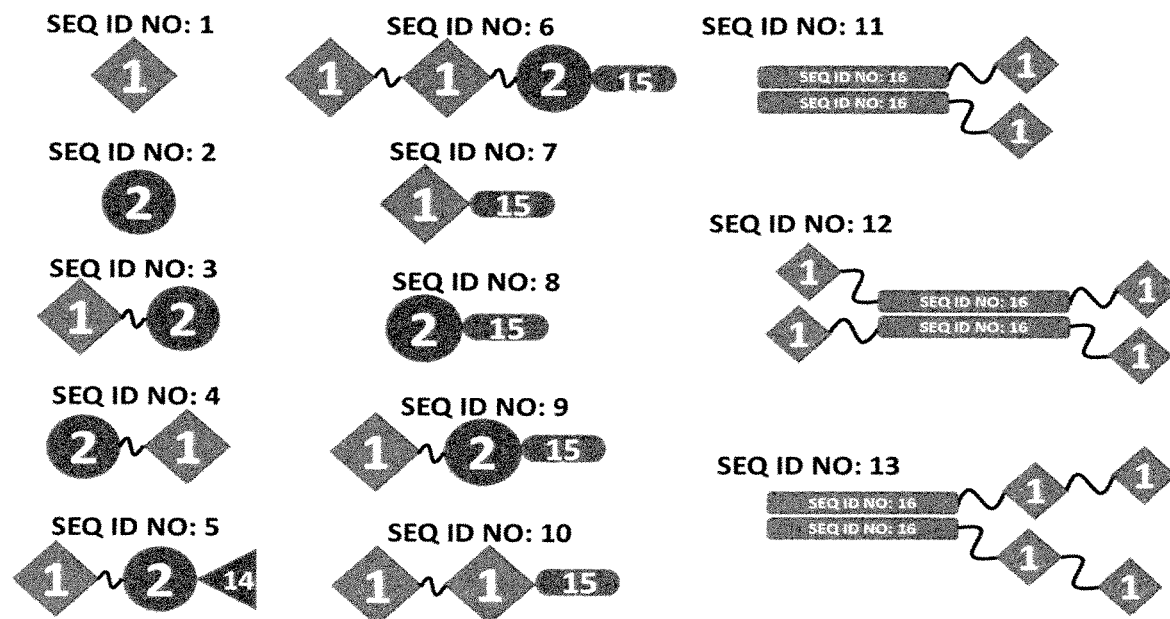

FIG. 11: provides a graphical overview over the constructs SEQ ID NOs: 1-13 characterised in Table 1. SEQ ID NO: 1 (abbreviated in FIG. 11 as "1") corresponds to the IL-17A-binding lipocalin mutein. SEQ ID NO: 2 (abbreviated as "2") corresponds to an IL-23-binding lipocalin mutein. SEQ ID NO: 14 (abbreviated as "14") corresponds to the albumin binding domain of streptococcal protein G. SEQ ID NO: 15 (abbreviated as "15") is an engineered, deimmunized version of SEQ ID NO: 14. SEQ ID NO: 16 (abbreviated as "16") corresponds to the Fc-part of a human IgG1 antibody.

Figure 12:
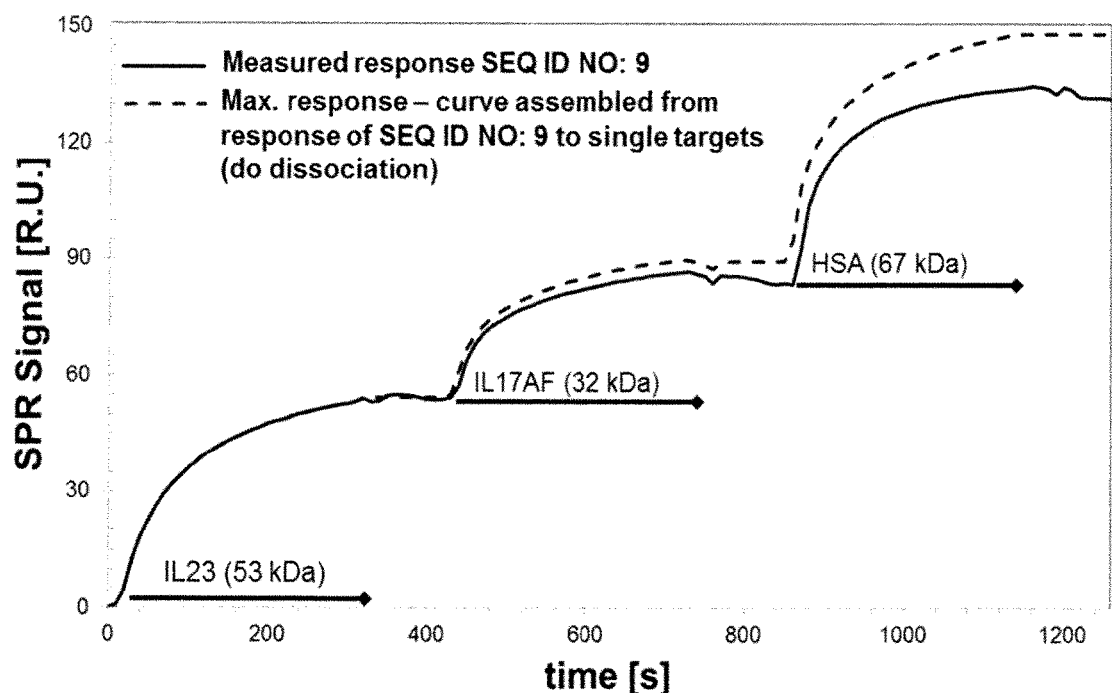

FIG. 12: demonstrates in an exemplary experiment that a multispecific fusion protein based on the lipocalin muteins disclosed herein is capable of binding IL-17A, IL-23 and human serum albumin (HSA) simultaneously, without interference by the respective other targets that are bound. SEQ ID NO: 9 is a heterodimeric fusion protein of the IL-17A binding lipocalin mutein SEQ ID NO: 1, the IL-23-binding lipocalin mutein SEQ ID NO: 2 and a human serum albumin binding peptide derived from the albumin binding domain of streptococcal protein G. In the surface plasmon resonance experiment shown in FIG. 12, biotinylated SEQ ID NO: 9 was captured on a sensor chip. To demonstrate simultaneous binding, dilutions of hIL-17AF, hIL-23 and HSA in buffer were consecutively applied to the prepared chip surface. The application of hIL-17AF, hIL-23 and HSA to immobilized SEQ ID NO: 9 was also performed employing the single target to obtain the maximum binding levels obtainable by binding a single target for comparison. The FIG. 12 shows the measured binding curve and a theoretical binding curve reflecting the response expected for complete binding of all three targets. The latter was obtained by assembling the experimental response of SEQ ID NO: 9 to the individual targets. The measured and the theoretical curve are nearly identical, with the exhibited difference attributable to dissociation of the targets in the experimental curve. The data shows that SEQ ID NO: 9 is capable of simultaneously binding all targets without a loss of signal intensity or a change in kinetics compared to binding a single target only.

Figure 13:
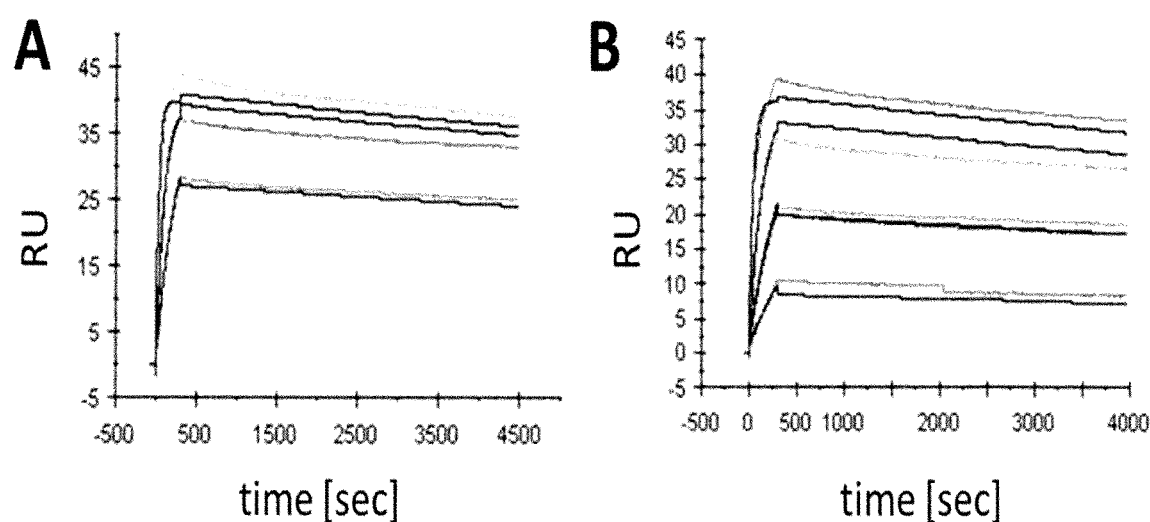

FIG. 13: provides typical measurements of on-rate and off-rate by Surface Plasmon Resonance for the lipocalin muteins SEQ ID NO: 45 (FIG. 13A) and SEQ ID NO: 46 (FIG. 13B) binding to human IL-23. The resulting dissociation constants ($K_D$) are 0-1 nM (SEQ ID NO: 45) and 0.6 nM (SEQ ID NO: 46), respectively.

Figure 14:
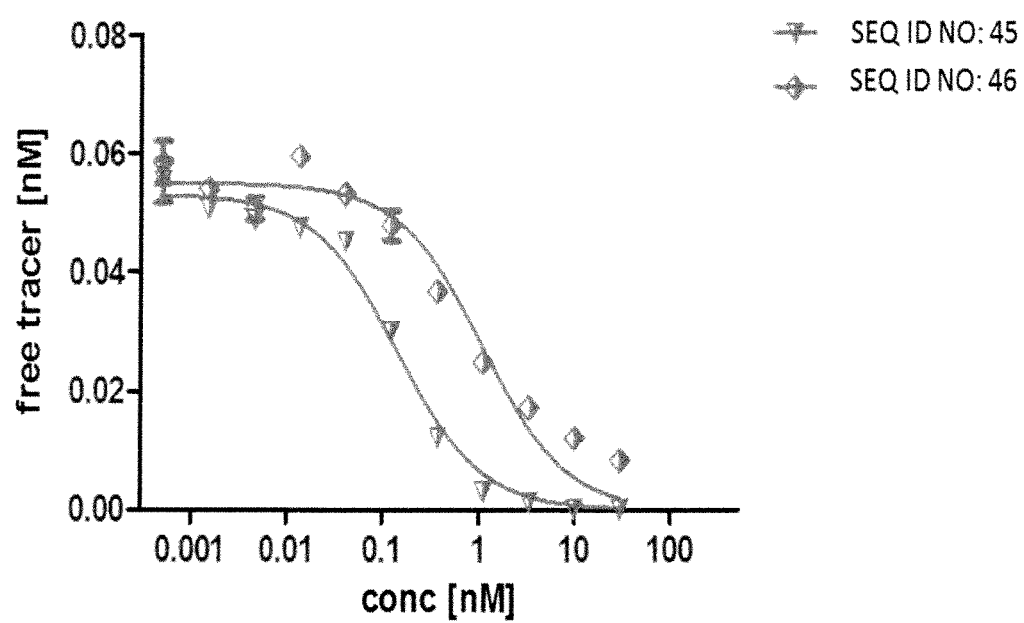

FIG. 14: demonstrates that the lipocalin muteins SEQ ID NO: 45 and SEQ ID NO: 46 are capable of blocking the interaction between hIL-23 and its receptor hIL-23R with an IC50 of 0.1 nM (SEQ ID NO: 45) and 1.1 nM (SEQ ID NO: 46), respectively. Biotinylated hIL-23 was pre-incubated with variable concentrations of said lipocalin muteins and non-neutralized hIL-23 was quantified on an ELISA plate with immobilized soluble hIL-23R. The data were fitted with a single-site binding model.

Figure 15:
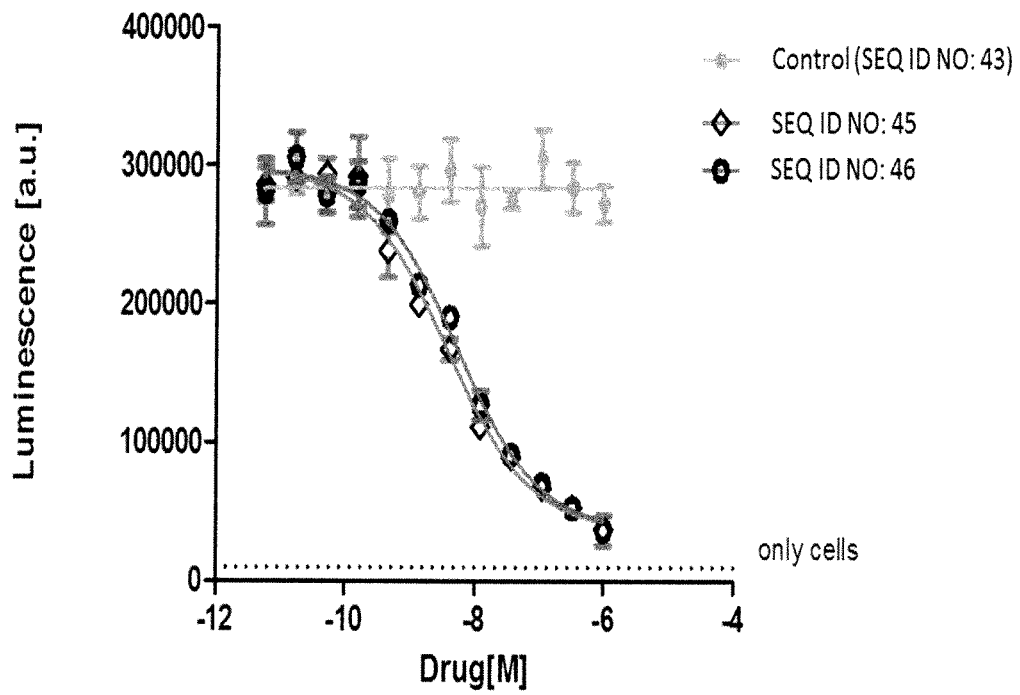

FIG. 15: demonstrates that the lipocalin muteins of SEQ ID NO: 45 and SEQ ID NO: 46 are capable of blocking the biological activity of hIL-23 in a cell-based proliferation assay. In the assay, SEQ ID NO: 45, SEQ ID NO: 46 and the negative control SEQ ID NO: 43 were preincubated with hIL-23 and subsequently added to Ba/F3 cells transfected with hIL-23R and hIL-12Rβ1. The transfected Ba/F3 cells proliferate in response to human IL-23. The experiment shows that this biological activity is blocked by SEQ ID NO: 45, SEQ ID NO: 46 with IC50 values of 3.7 nM, and 5.4 nM, respectively. The negative control SEQ ID NO: 43 had no effect on cell proliferation. The data were fitted with a sigmoidal dose-response model.

Figure 16:
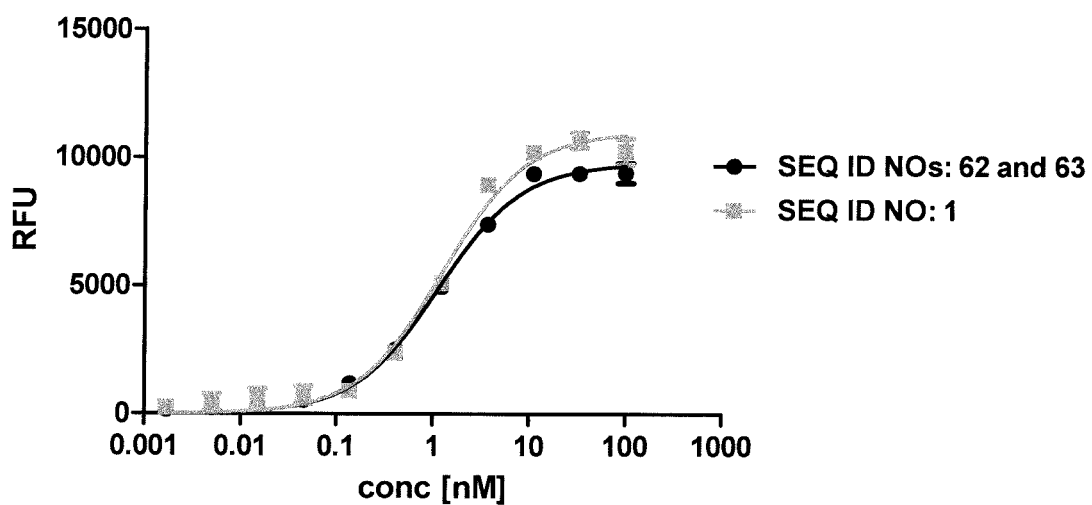

FIG. 16: provides a representative experiment in which the specificity of SEQ ID NOs: 63 and 62 and the lipocalin mutein of SEQ ID NO: 1 towards the target IL-17A was determined. Biotinylated IL-17A was captured on a microtiter plate and the test molecules were titrated. Bound test molecules were detected via an HRP-labeled anti-human TLc-specific antibody as described in Example 16. The data was fitted with a 1:1 binding model with EC50 value and the maximum signal as free parameters, and a slope that was fixed to unity.

Figure 17:
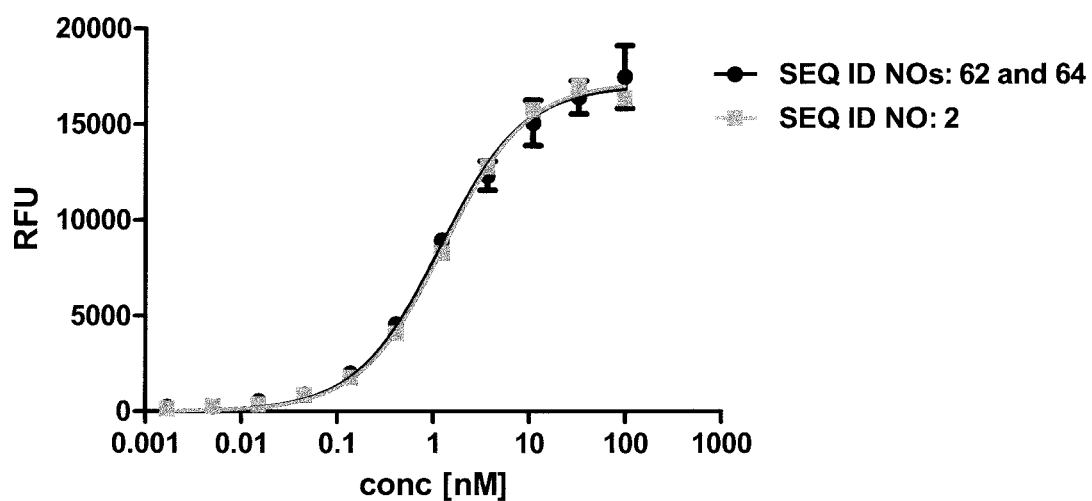

FIG. 17: provides a representative experiment in which the specificity of SEQ ID NOs: 64 and 62 and the lipocalin mutein of SEQ ID NO: 2 towards the target IL-23 was determined. Biotinylated IL-23 was captured on a microtiter plate, and the test molecules were titrated. Bound test molecules were detected via an HRP-labeled anti-human NGAL-specific antibody as described in Example 17. The data was fitted with a 1:1 binding model with EC50 value and the maximum signal as free parameters, and a slope that was fixed to unity.

Figure 18:
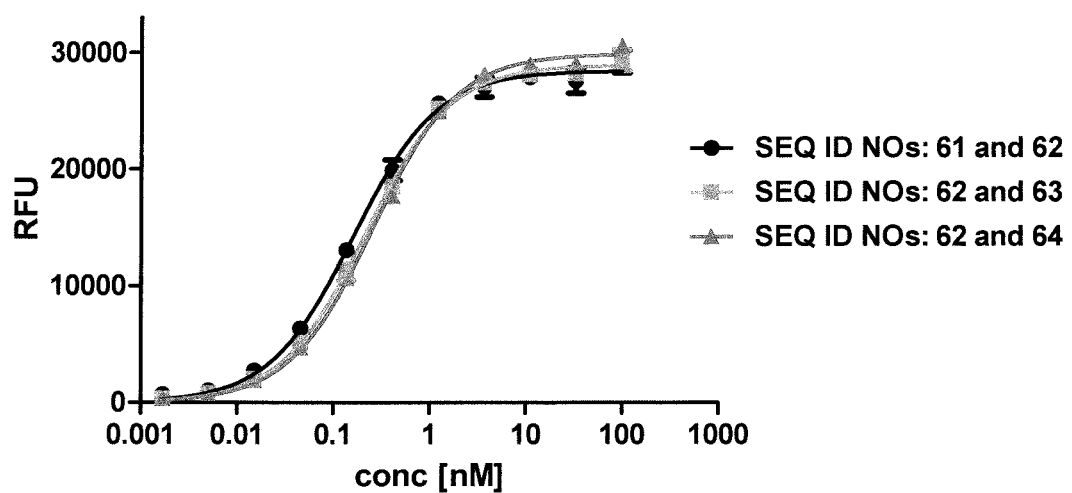

FIG. 18: provides a representative experiment in which the specificity of the polypeptide fusion of SEQ ID NOs: 63 and 62 and the polypeptide fusion of SEQ ID NOs: 64 and 62, as well as that of the antibody of SEQ ID NOs: 61 and 62 towards the target TNF-α was determined. TNF-α was coated on a microtiter plate, and the test molecules were titrated. Bound test molecules were detected via an HRP-labeled anti-human IgG Fc-specific antibody as described in Example 18. The data was fitted with a 1:1 binding model with EC50 value and the maximum signal as free parameters, and a slope that was fixed to unity.

Figure 19:
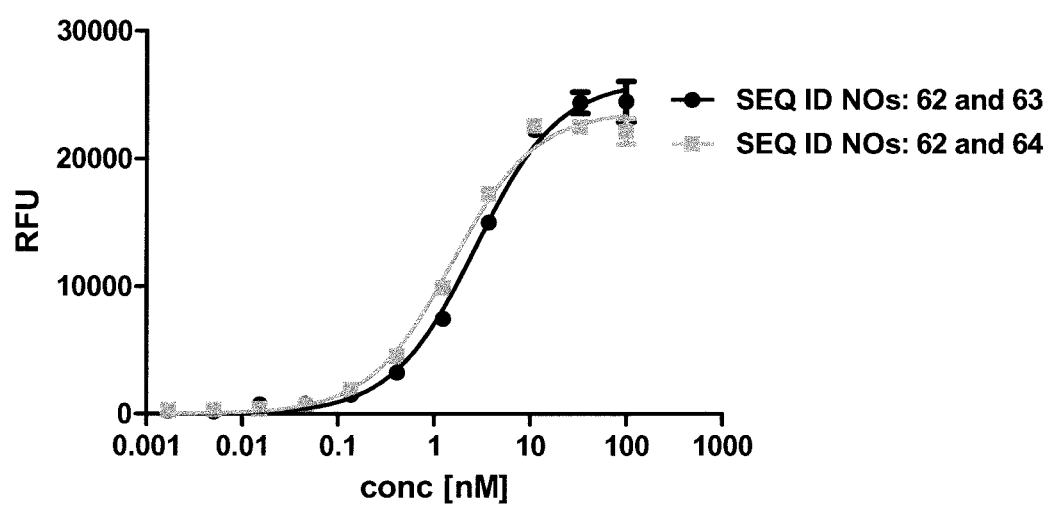

FIG. 19: provides a representative experiment in which the ability of the polypeptide fusion of SEQ ID NOs: 63 and 62 and the polypeptide fusion of SEQ ID NOs: 64 and 62 to simultaneously bind both targets—TNF-α and IL-17A, TNF-α and IL-23, respectively—was determined. Recombinant TNF-α was coated on a microtiter plate, followed by a titration of the polypeptide fusions. Subsequently, a constant concentration of either biotinylated IL-17A or IL-23 was added, which was detected via HRP-labeled extravidin as described in Example 19. The data was fitted with a 1:1 binding model with EC50 value and the maximum signal as free parameters, and a slope that was fixed to unity.

IV. DETAILED DESCRIPTION OF THE DISCLOSURE

The present disclosure contributes to the state of art a polypeptide or protein having binding specificity for IL-17A and/or IL-23p19, wherein the polypeptide comprises a lipocalin mutein that binds with at least a detectable affinity to IL-17A or IL-23p19.

In some embodiments, the polypeptide is a lipocalin mutein that is capable of binding IL-17A with at least a detectable affinity. In some embodiments, the polypeptide is a lipocalin mutein that is capable of binding IL-23p19 with at least a detectable affinity. The present disclosure also relates to use of both polypeptides, for the binding of IL-17A and IL-23p19 in a subject.

In some aspects, the polypeptide is a fusion protein comprising at least two subunits, wherein one subunit has binding specificity for IL-17A and another subunit has binding specificity for IL-23p19. In some further embodiments, the fusion protein may further comprise a subunit, wherein the subunit has binding specificity for IL-23p19 or IL-17A. In some still further embodiments, the fusion protein may comprise one subunit specific for IL-17A, one subunit specific for IL-23p19, and one subunit containing a bacterial albumin binding domain (ABD).

In some other aspects, a polypeptide of the disclosure may also be a fusion protein comprising at least two subunits specific for IL-17A, or a fusion protein comprising at least two subunits specific for IL-23p19.

In some embodiments, the subunit of the fusion protein having binding specificity for IL-17A comprises a lipocalin mutein specific for IL-17A of the disclosure. In some embodiments, the subunit of the fusion protein having binding specificity for IL-23p19 comprises an antibody that binds to IL-23p19. In some other embodiments, the subunit of the fusion protein having binding specificity for IL-23p19 comprises a lipocalin mutein specific for IL-23p19 of the disclosure. In some embodiments, the subunit of the fusion protein having binding specificity for IL-17A comprises an antibody that binds to IL-17A.

A polypeptide or protein of the disclosure can be a mutein of a lipocalin, preferably a lipocalin selected from the group consisting of retinol-binding protein (RBP), bilin-binding protein (BBP), apolipoprotein D (APO D), neutrophil gelatinase associated lipocalin (NGAL), tear lipocalin (TLPC or Tlc), $\alpha_2$-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1).

As used herein, a "lipocalin" is defined as a monomeric protein of approximately 18-20 kDA in weight, having a cylindrical β-pleated sheet supersecondary structural region comprising a plurality of (preferably eight) β-strands connected pair-wise by a plurality of (preferably four) loops at one end to define thereby a binding pocket. It is the diversity of the loops in the otherwise rigid lipocalin scaffold that gives rise to a variety of different binding modes among the lipocalin family members, each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350). Indeed, the lipocalin family of proteins have naturally evolved to bind a wide spectrum of ligands, sharing unusually low levels of overall sequence conservation (often with sequence identities of less than 20%) yet retaining a highly conserved overall folding pattern. The correspondence between positions in various lipocalins is well known to one of skill in the art. See, for example, U.S. Pat. No. 7,250,297.

As noted above, a lipocalin is a polypeptide defined by its supersecondary structure, namely cylindrical β-pleated sheet supersecondary structural region comprising eight β-strands connected pair-wise by four loops at one end to define thereby a binding pocket. The present disclosure is not limited to lipocalin muteins specifically disclosed herein. In this regard, the disclosure relates to a lipocalin mutein having a cylindrical 1-pleated sheet supersecondary structural region comprising eight β-strands connected pair-wise by four loops at one end to define thereby a binding pocket, wherein at least one amino acid of each of at least three of said four loops has been mutated and wherein said lipocalin is effective to bind IL-17A or IL-23p19 with detectable affinity.

In one particular embodiment, a lipocalin mutein disclosed herein is a mutein of human tear lipocalin (TLPC or Tlc), also termed lipocalin-1, tear pre-albumin or von Ebner gland protein. The term "human tear lipocalin" or "Tlc" or "lipocalin-1" as used herein refers to the mature human tear lipocalin with the SWISS-PROT/UniProt Data Bank Accession Number P31025 (Isoform 1). The amino acid sequence shown in SWISS-PROT/UniProt Data Bank Accession Number P31025 may be used as a preferred "reference sequence", more preferably the amino acid sequence shown in SEQ ID NO: 41 is used as reference sequence.

The present disclosure also encompasses Tlc muteins as defined above, in which the first four N-terminal amino acid residues of the sequence of mature human tear lipocalin (His-His-Leu-Leu; positions 1-4) and/or the last two C-terminal amino acid residues (Ser-Asp; positions 157-158) of the linear polypeptide sequence of the mature human tear lipocalin (SWISS-PROT Data Bank Accession Number P31025) have been deleted (SEQ ID NOs: 2-5). In addition, the present disclosure encompasses Tlc muteins as defined above, in which one GH loop amino acid residue (Lys) corresponding to sequence position 108 of the linear polypeptide sequence of the mature human tear lipocalin has been deleted (SEQ ID NO: 1 and SEQ ID NO: 43). Another possible mutation of the wild type polypeptide sequence of the mature human tear lipocalin is to change the amino acid sequence at sequence positions 5 to 7 (Ala Ser Asp) to Gly Gly Asp as described in PCT application WO 2005/019256, which is incorporated by reference its entirety herein.

A Tlc mutein according to the disclosure may further include an amino acid substitution Arg 111→Pro. A Tlc mutein according to the disclosure may also include a substitution Lys 114→Trp. It may also comprise a substitution Cys 101→Ser or Cys 101→Thr. In some preferred embodiments, a Tlc mutein according to the disclosure may also comprise a substitution Cys 153→Ser.

Modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a Tlc mutein for IL-17A or IL-23p19. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. Exemplary possibilities of such a mutation to introduce a cysteine residue into the amino acid sequence of a Tlc mutein include the substitutions Thr 40→Cys, Glu 73→Cys, Arg 90→Cys, Asp 95→Cys, and Glu 131→Cys. The generated thiol moiety at the side of any of the amino acid positions 40, 73, 90, 95 and/or 131 may be used to PEGylate or HESylate the mutein, for example, in order to increase the serum half-life of a respective Tlc mutein.

In another particular embodiment, a lipocalin mutein disclosed herein is a mutein of human lipocalin 2. The term "human lipocalin 2" or "human Lcn 2" or "human NGAL" as used herein refers to the mature human neutrophil gelatinase-associated lipocalin (NGAL) with the SWISS-PROT/UniProt Data Bank Accession Number P80188. A human lipocalin 2 mutein of the disclosure may also be designated herein as "an hNGAL mutein". The amino acid sequence shown in SWISS-PROT/UniProt Data Bank Accession Number P80188 may be used as a preferred "reference sequence", more preferably the amino acid sequence shown in SEQ ID NO: 43 is used as reference sequence.

In some embodiments, a lipocalin mutein binding IL-17A or IL-23p19 with detectable affinity may include at least one amino acid substitution of a native cysteine residue by another amino acid, for example, a serine residue. In some other embodiments, a lipocalin mutein binding IL-17A or IL-23p19 with detectable affinity may include one or more non-native cysteine residues substituting one or more amino acids of a wild type lipocalin. In a further particular embodiment, a lipocalin mutein according to the disclosure includes at least two amino acid substitutions of a native amino acid by a cysteine residue, hereby to form one or more cysteine bridges. In some embodiments, said cysteine bridge may connect at least two loop regions. The definition of these regions is used herein in accordance with Flower (Flower, 1996, supra, Flower, et al., 2000, supra) and Breustedt et al. (2005, supra).

Proteins of the disclosure, which are directed against or specific for IL-17A or IL-23p19, include any number of specific-binding protein muteins that are based on a defined protein scaffold. Preferably, the number of nucleotides or amino acids, respectively, that is exchanged, deleted or inserted is 1, 2, 3, 4, 5, 6, 7, 8, 9, 10, 11, 12, 13, 14, 15, 16, 17, 18, 19, 20 or more such as 25, 30, 35, 40, 45 or 50, with 1, 2, 3, 4, 5, 6, 7, 8, 9, 10, or 11 being preferred and 9, 10 or 11 being even more preferred. However, it is preferred that a lipocalin mutein of the disclosure is still capable of binding IL-17A or IL-23p19, in particular human IL-17A or human IL-23p19.

In one aspect, the present disclosure includes various lipocalin muteins that bind IL-17A or IL-23p19 with at least detectable affinity. In this sense, IL-17A or IL-23p19 can be regarded a non-natural ligand of the reference wild type lipocalin, where "non-natural ligand" refers to a compound that does not bind to wildtype lipocalins under physiological conditions. By engineering wildtype lipocalins with one or more mutations at certain sequence positions, the present inventors have demonstrated that high affinity and high specificity for the non-natural ligand, e.g. IL-17A or IL-23p19, is possible. In some embodiments, at 1, 2, 3, 4, 5, 6, 7, 8, 9, 10, 11, 12 or even more nucleotide triplet(s) encoding certain sequence positions on wildtype lipocalins, a random mutagenesis may be carried out through substitution at these positions by a subset of nucleotide triplets.

Further, the lipocalin muteins of the disclosure may have a mutated amino acid residue at any one or more, including at least at any one, two, three, four, five, six, seven, eight, nine, ten, eleven or twelve, of the sequence positions corresponding to certain sequence positions of the linear polypeptide sequence of the reference lipocalin.

A protein of the disclosure may include the wild type (natural) amino acid sequence of the "parental" protein scaffold (such as a lipocalin) outside the mutated amino acid sequence positions. In some embodiments, a lipocalin mutein according to the disclosure may also carry one or more amino acid mutations at a sequence position/positions as long as such a mutation does, at least essentially not hamper or not interfere with the binding activity and the folding of the mutein. Such mutations can be accomplished very easily on DNA level using established standard methods (Sambrook, J. et al. (2001) Molecular Cloning: A Laboratory Manual, 3rd Ed., Cold Spring Harbor Laboratory Press, Cold Spring Harbor, N.Y.). Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of the human tear lipocalin as long as these deletions or insertion result in a stable folded/functional mutein (for example, Tlc muteins with truncated N- and C-terminus). In such mutein, for instance, one or more amino acid residues are added or deleted at the N- or C-terminus of the polypeptide. Generally such a mutein may have about at least 70%, including at least about 80%, such as at least about 85% amino acid sequence identity, with the amino acid sequence of the mature human tear lipocalin. As an illustrative example, the present disclosure also encompasses Tlc muteins as defined above, in which the first four N-terminal amino acid residues of the sequence of mature human tear lipocalin (His-His-Leu-Leu; positions 1-4) and/ or the last two C-terminal amino acid residues (Ser-Asp; positions 157-158) of the linear polypeptide sequence of the mature human tear lipocalin have been deleted (SEQ ID NO: 1 and SEQ ID NO: 43).

The amino acid sequence of a lipocalin mutein disclosed herein has a high sequence identity to the reference lipocalin when compared to sequence identities with other lipocalins. In this general context, the amino acid sequence of a lipocalin mutein of the disclosure is at least substantially similar to the amino acid sequence of the reference lipocalin, with the proviso that possibly there are gaps (as defined below) in an alignment that are the result of additions or deletions of amino acids. A respective sequence of a lipocalin mutein of the disclosure, being substantially similar to the sequences of the reference lipocalin, has, in some embodiments, at least 70% identity or sequence homology, at least 75% identity or sequence homology, at least 80% identity or sequence homology, at least 82% identity or sequence homology, at least 85% identity or sequence homology, at least 87% identity or sequence homology, or at least 90% identity or sequence homology including at least 95% identity or sequence homology, to the sequence of the reference lipocalin, with the proviso that the altered position or sequence is retained and that one or more gaps are possible.

As used herein, a lipocalin mutein of the disclosure "specifically binds" a target (for example, IL-17A or IL-23p19) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In one embodiment, the lipocalin muteins of the disclosure are fused at its N-terminus and/or its C-terminus to a fusion partner which is a protein domain that extends the serum half-life of the mutein. In further particular embodiments, the protein domain is a Fc part of an immunoglobulin, a CH3 domain of an immunoglobulin, a CH4 domain of an immunoglobulin, an albumin binding domain, an albumin binding peptide, or an albumin binding protein.

In another embodiment, the lipocalin muteins of the disclosure are conjugated to a compound that extends the serum half-life of the mutein. More preferably, the mutein is conjugated to a compound selected from the group consisting of a polyalkylene glycol molecule, a hydroethylstarch, an Fc part of an immunoglobulin, a CH3 domain of an immoglobulin, a CH4 domain of an immunoglobulin, an albumin binding domain, an albumin binding peptide, and an albumin binding protein.

In yet another embodiment, the current disclosure relates to a nucleic acid molecule comprising a nucleotide sequence encoding a lipocalin mutein disclosed herein. The disclosure encompasses a host cell containing said nucleic acid molecule.

A Tlc mutein according to the present disclosure can be obtained by means of mutagenesis of a naturally occurring form of human tear lipocalin. An hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution—including non-conservative substitution or one or more from the exemplary substitutions below—is envisaged as long as the lipocalin mutein retains its capability to bind to IL-17A or IL-23p19, and/or it has an identity to the then substituted sequence in that it is at least 60%, such as at least 65%, at least 70%, at least 75%, at least 80%, at least 85% or higher identity to the amino acid sequence of the mature human tear lipocalin or the mature human lipocalin 2, respectively.

A. Lipocalin Muteins with Binding-Affinity for Interleukin-17A (IL-17A, Synonymous with IL-17)

In one aspect, the present disclosure provides human lipocalin muteins that bind human IL-17A (same as "IL-17") and useful applications therefor. Binding proteins described herein may bind human IL-17A homodimer (same as "IL-17 A") and/or heterodimers of human IL-17A and the human IL-17F homolog (same as "IL-17 A/F"). The disclosure also provides methods of making IL-17A binding proteins described herein as well as compositions comprising such proteins. IL-17A binding proteins of the disclosure as well as compositions thereof may be used in methods of detecting IL-17A (including IL-17 A/A and IL-17 A/F) in a sample or in methods of binding IL-17A (including IL-17 A/A and IL-17 A/F) in a subject. No such human lipocalin muteins having these features attendant to the uses provided by present disclosure have been previously described.

One embodiment of the current disclosure relates to a lipocalin mutein that is capable of binding Interleukin-17A (IL-17A) with an affinity measured by a $K_D$ of about 1 nM or lower, such as 0.8 nM, when measured in an assay essentially described in Example 1.

In some other embodiments, the lipocalin mutein is capable of inhibiting the binding of IL-17A to its receptor IL-17RA with an IC50 value of about 100 pM or lower, such as 75 pM, in a competition ELISA format essentially described in Example 3.

In some particular embodiments, the IL-17A-binding lipocalin mutein is crossreactive with human IL-17A, cynomolgus IL-17A and marmoset monkey IL-17A.

In some still further embodiments, a lipocalin mutein of the disclosure is capable of blocking IL-17A binding to its receptor IL-17RA. In some further embodiments, the lipocalin mutein has an average EC50 value at least as good as (i.e. where in difference is less than 0.1 nM) or superior to the EC50 value of a benchmark antibody, when said lipocalin mutein and the benchmark antibody are measured in an assay essentially as described in Example 5. In some embodiments, the benchmark antibody is a polypeptide comprising (i) SEQ ID NO: 53 or 55 as the first subunit and (ii) SEQ ID NO: 54 or 56 as the second subunit. The lipocalin mutein may have an average IC50 value of about 0.13 nM or even lower in the assay when at the same time the benchmark antibody has an EC50 value of about 2.33 nM or lower in the assay, such as about 0.12 nM.

In some other embodiments, an IL-17A-binding lipocalin mutein of the current disclosure is capable of binding IL-17A with a higher affinity than the lipocalin mutein of SEQ ID NO: 42, measured by a lower $K_D$ of the first said lipocalin mutein than the $K_D$ of the lipocalin mutein of SEQ ID NO: 42, for example, in an assay essentially described in Example 1. In some further embodiments, an IL-17A-binding lipocalin mutein of the current disclosure is capable of inhibiting the binding of IL-17A to its receptor IL-17RA with a lower EC50 value than that of the lipocalin mutein of SEQ ID NO: 42, for example, when measured in an assay essentially described in Example 5.

1. Exemplary Lipocalin Muteins with Binding-Affinity for Interleukin-17A (IL-17A)

In one aspect, the present disclosure relates to novel, specific-binding human tear lipocalin muteins directed against or specific for Interleukin-17A (IL-17A). Human tear lipocalin muteins disclosed herein may be used for therapeutic and/or diagnostic purposes. A human tear lipocalin mutein of the disclosure may also be designated herein as "a Tlc mutein". As used herein, a Tlc mutein of the disclosure "specifically binds" a target (e.g. here, IL-17A) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In this regard, the disclosure provides one or more Tlc muteins that are capable of binding Interleukin-17A (IL-17A) with an affinity measured by a KD of about 10 nM, about 1 nM, about 0.1 nM or lower. More preferably, the Tlc muteins can have an affinity measured by a KD of about 1 nM, 0.8 nM, 0.6 nM, 100 pM or lower.

In some particular embodiments, such Tlc mutein includes a mutated amino acid residue at one or more positions corresponding to positions 26-33, 56, 58, 60-61, 64, 92, 101, 104-106, 108, 111, 114 and 153 of the linear polypeptide sequence of the mature human tear lipocalin (SWISS-PROT Data Bank Accession Number P31025; SEQ ID NO: 41).

In further particular embodiments, such Tlc mutein may further include a mutated amino acid residue at one or more positions corresponding to positions 101, 111, 114 and 153 of the linear polypeptide sequence of the mature human tear lipocalin (SEQ ID NO: 41).

In some further embodiments, the Tlc mutein may contain at least 1, 2, 3, 4, 5, 6, 7, 8, 9, 10, 11, 12, 13, 14, 15, 16, 17, 18, 19, 20, 21, or even more, mutated amino acid residues at one or more sequence positions corresponding to sequence positions 26, 27, 28, 29, 30, 31, 32, 33, 56, 58, 60, 61, 64, 92, 101, 104, 105, 106, 108, 111, 114 and 153 ofthe linear polypeptide sequence of the mature human tear lipocalin (SEQ ID NO: 41).

In some still further embodiments, the disclosure relates to a polypeptide, wherein said polypeptide is a Tlc mutein, in comparison with the linear polypeptide sequence of the mature human tear lipocalin, comprising at least 2, 3, 4, 5, 6, 7, 8, 9, 10, 11, 12 or even more, mutated amino acid residues at the sequence positions 26-33, 56, 58, 60-61, 64, 92, 101, 104-106, 108, 111, 114 and 153 and wherein said polypeptide binds IL-17A, in particular human IL-17A.

In some embodiments, a lipocalin mutein according to the disclosure may include at least one amino acid substitution of a native cysteine residue by e.g. a serine residue. In some embodiments, a Tlc mutein according to the disclosure includes an amino acid substitution of a native cysteine residue at positions 61 and/or 153 by a serine residue. In this context it is noted that it has been found that removal of the structural disulfide bond (on the level of a respective naïve nucleic acid library) of wild type tear lipocalin that is formed by the cysteine residues 61 and 153 (cf. Breustedt, et al., 2005, supra) may provide tear lipocalin muteins that are not only stably folded but are also able to bind a given non-natural ligand with high affinity. Without wishing to be bound by theory, it is also believed that the elimination of the structural disulde bond provides the further advantage of allowing for the (spontaneous) generation or deliberate introduction of non-natural artificial disulfide bonds into muteins of the disclosure, thereby increasing the stability of the muteins. For example, in some embodiments, a Tlc mutein according to the disclosure includes an amino acid substitution of a native cysteine residue at position 101 by a serine residue. Further, in some embodiments, a mutein according to the disclosure includes an amino acid substitution of a native arginine residue at positions 111 by a proline residue. In some embodiments a mutein according to the disclosure includes an amino acid substitution of a native lysine residue at positions 114 by a tryptophan residue.

A Tlc mutein according to the disclosure may further include, with respect to the amino acid sequence of the mature human tear lipocalin (SWISS-PROT Data Bank Accession Number P31025), one or more, including at least two, at least three, at least four, at least five, at least six, at least seven, at least eight, at least nine, at least ten, at least eleven, at least twelve, at least thirteen or at least fourteen amino acid substitutions of native amino acid residues by cysteine residues at any of positions 26-33, 56, 58, 60-61, 64, 92, 101, 104-106, 108, 111, 114 and 153 of the mature human tear lipocalin.

In some embodiments, a mutein according to the disclosure includes an amino acid substitution of a native amino acid by a cysteine residue at positions 28 or 105 with respect to the amino acid sequence of mature human tear lipocalin. In some embodiments a mutein according to the disclosure includes an amino acid substitution of a native amino acid by a cysteine residue at positions 28 or 105 with respect to the amino acid sequence of mature human tear lipocalin. In a further particular embodiment, a mutein according to the disclosure includes an amino acid substitution of a native amino acid by two cysteine residues at positions 28 and 105 with respect to the amino acid sequence of mature human tear lipocalin.

In some embodiments, a Tlc mutein according to the disclosure includes a substituted amino acid of at least one or of both of the cysteine residues occurring at each of the sequences positions 61 and 153 by another amino acid and the mutation of at least three amino acid residue at any one of the sequence positions 26-33, 56, 58, 60-61, 64, 92, 101, 104-106, 108, 111, 114 and 153 of the linear polypeptide sequence of the mature human tear lipocalin (SWISS-PROT Data Bank Accession Number P31025). The positions 26-34 are included in the AB loop, the position 55 is located at the very end of a beta-sheet and following positions 56-58 as well as 60-61 and 64 are included in the CD loop. The positions 104-108 are included in the GH loop in the binding site at the open end of the β-barrel structure of the mature human tear lipocalin. The definition of these regions is used herein in accordance with Flower (Flower, 1996, supra, Flower, et al., 2000, supra) and Breustedt et al. (2005, supra). In some embodiments, the Tlc mutein according to the disclosure includes the amino acid substitutions Cys 61→Ala, Phe, Lys, Arg, Thr, Asn, Gly, Gln, Asp, Asn, Leu, Tyr, Met, Ser, Pro or Trp and Cys 153→Ser or Ala. Such a substitution has proven useful to prevent the formation of the naturally occurring disulphide bridge linking Cys 61 and Cys 153, and thus to facilitate handling of the mutein. However, tear lipocalin muteins that binds IL-17A and that have the disulphide bridge formed between Cys 61 and Cys 153 are also part of the present disclosure.

In some embodiments, an IL-17A-binding Tlc mutein according to the disclosure includes, at any one or more of the sequence positions 26-33, 56, 58, 60-61, 64, 92, 101, 104-106, 108, 111, 114 and 153 of the linear polypeptide sequence of the mature human tear lipocalin (SEQ ID NO: 41), one or more of the following mutated amino acid residues: Arg 26→Phe; Glu 27→Trpl; Phe 28→Cys; Pro 29→Ser; Glu 30→Gly; Met 31→Ile; Asn 32→His; Leu 33→Glu; Leu 56→Asp; Ser 58→Glu; Arg 60→Phe; Cys 61→Leu; Val 64→Phe; His 92→Arg; Cys101→Ser; Glu 104-Asp; Leu 105→Cys; His 106→Pro; deletion of Lys 108; Arg 111→Pro; Lys 114→Trp; and Cys 153→Ser. In some embodiments, a Tlc mutein of the disclosure includes two or more, such as 3, 4, 5, 6, 7, 8 or all mutated amino acid residues at these sequence positions of the mature human tear lipocalin.

In further particular embodiments, a Tlc mutein of the disclosure comprises an amino acid sequence as set forth in any one of SEQ ID NOs: 1 or a fragment or variant thereof.

In further particular embodiments, a Tlc mutein of the disclosure has at least 75%, at least 80%, at least 85% or higher identity to an amino acid sequence selected from the group consisting of SEQ ID NOs: 1.

The disclosure also includes structural homologues of a Tlc mutein having an amino acid sequence selected from the group consisting of SEQ ID NOs: 1, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said Tlc mutein.

In some particular embodiments, the present disclosure provides a lipocalin mutein that binds IL-17A with an affinity measured by a KD of about 1 nM or lower, wherein the lipocalin mutein has at least 90% or higher, such as 95%, identity to the amino acid sequence of SEQ ID NO: 1.

2. Applications of Lipocalin Muteins with Binding-Affinity for Interleukin-17A (IL-17A)

IL-17A is a pro-inflammatory cytokine produced by a subset of memory T cells (called Th17) that has been implicated in the pathogenesis of many disorders, e.g. multiple sclerosis (MS) (Hellings, P. W. et al., Am. J. Resp. Cell Mol. Biol. 28 (2003) 42-50; Matusevicius, D. et al., Multiple Sclerosis 5 (1999) 101-104), rheumatoid arthritis (RA) (Ziolkovvska, M. et al., J. Immunol. 164 (2000) 2832-38; Kotake, S. et al., J. Clin. Invest. 103 (1999) 1345-52; Hellings, P. W. et al., Am. J. Resp. Cell Mol. Biol. 28 (2003) 42-50). IL-17A plays a role in the induction of other inflammatory cytokines, chemokines and adhesion molecules (Komiyama, Y. et al., J. Immunol. 177 (2006) 566-573), psoriasis, Crohn's disease, chronic obstructive pulmonary disease (COPD), asthma, and transplant rejection.

IL-17A is involved in the induction of proinflammatory responses and induces or mediates expression of a variety of other cytokines, factors, and mediators including tissue necrosis factor-alpha (TNF-α), IL-6, IL-8, IL-1p, granulocyte colony-stimulating factor (G-CSF), prostaglandin E2 (PGE2), IL-10, IL-12, IL-IR antagonist, leukemia inhibitory factor, and stromelysin (Yao et al., J. Immunol, 155(12): 5483-5486 (1995); Fossiez et al., J. Exp. Med., 183(6): 2593-2603 (1996); Jovanovic et al., J. Immunol, 160: 3513-3521 (1998); Teunissen et al., J. Investig. Dermatol, 111: 645-649 (1998); Chabaud et al., J. Immunol, 161: 409-414 (1998)). IL-17A also induces nitric oxide in chondrocytes and in human osteoarthritis explants (Shalom-Barak et al., J. Biol Chem., 273: 27467-27473 (1998); Attur et al., Arthritis Rheum., 40: 1050-1053 (1997)). Through its role in T cell mediated autoimmunity, IL-17A induces the release of cytokines, chemokines, and growth factors (as noted above), is an important local orchestrator of neutrophil accumulation, and plays a role in cartilage and bone destruction. There is growing evidence that targeting IL-17A signaling might prove useful in a variety of autoimmune diseases including rheumatoid arthritis (RA), psoriasis, Crohn's disease, multiple sclerosis (MS), psoriatric disease, asthma, and lupus (SLE) (see, e.g., Aggarwal et al., J. Leukoc. Biol, 71(1): 1-8 (2002); Lubberts et al., "Treatment with a neutralizing anti-murine interleukin-17 antibody after the onset of collagen-induced arthritis reduces joint inflammation, cartilage destruction, and bone erosion," Arthritis Rheum., 50: 650-659 (2004)).

In addition, it is known in the art that inflammatory and immunoregulatory processes are implicated in the pathogenesis of various forms of cardiovascular disease (Biasucci, L., et al., Circulation 1999, 99:855-860; Albert, C, et al, Circulation 2002, 105:2595-9; Buffon, A., et al, NEJM 2002, 347:55-7; Nakajima, T., et al., Circulation 2002, 105:570-5). Recent studies have established a basis for treating cardiovascular disease by reducing inflammatory and immunoregulatory responses of the disease (Blankenberg, S., et al., Circulation 2002, 106:24-30; Mallat, Z., et al, Circulation 2001, 104:1598-603; Mallat, Z., et al, Circ Res. 2001, 89:E41-5). Cardiovascular disease encompasses a number of disorders that affect the muscle and/or blood vessels of the heart, peripheral blood vessels, muscles and various organs.

Numerous possible applications for the Tlc muteins of the disclosure, therefore, exist in medicine. In one further aspect, the disclosure relates to the use of a Tlc mutein disclosed for detecting IL-17A (including IL-17 A/A and IL-17 A/F) in a sample as well as a respective method of diagnosis.

The present disclosure also involves the use of one or more Tlc muteins as described for complex formation with IL-17A.

Therefore, in another aspect of the disclosure, the disclosed muteins are used for the detection of IL-17A. Such use may include the steps of contacting one or more said muteins, under suitable conditions, with a sample suspected of containing IL-17A, thereby allowing formation of a complex between the muteins and IL-17A, and detecting the complex by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins disclosed herein may also be used for the separation of IL-17A. Such use may include the steps of contacting one or more said muteins, under suitable conditions, with a sample supposed to contain IL-17A, thereby allowing formation of a complex between the muteins and IL-17A, and separating the complex from the sample.

In the use of the disclosed muteins for the detection of IL-17A as well as the separation of IL-17A, the muteins and/or IL-17A or a domain or fragment thereof may be immobilized on a suitable solid phase.

In still another aspect, the present disclosure features a diagnostic or analytical kit comprising a Tlc mutein according to the disclosure.

In addition to their use in diagnostics, in yet another aspect, the disclosure encompasses the use of a mutein of the disclosure or a composition comprising such mutein for the binding of IL-17A in a subject and/or inhibiting the binding of IL-17A to its receptor in a subject.

In still another aspect, the present disclosure features a method of binding IL-17A in a subject, comprising administering to said subject an effective amount of one or more lipocalin muteins of the disclosure or of one or more compositions comprising such muteins.

In still another aspect, the present disclosure involves a method for inhibiting the binding of IL-17A to its receptor in a subject, comprising administering to said subject an effective amount of one or more lipocalin muteins of the disclosure or of one or more compositions comprising such muteins.

In the context of the present disclosure, the disclosed lipocalin muteins with binding-affinity for IL-17A can bind to IL-17A that exists as a homodimer, but such muteins can also bind to IL-17A that exists as a heterodimer complexed with the homolog IL-17F to form heterodimeric IL-17 A/F. In one preferred embodiment, one lipocalin mutein of the disclosure may bind with a detectable affinity to IL-17A in complex with IL-17F.

B. Lipocalin Muteins with Binding-Affinity for Interleukin-23p19 (IL-23p19)

In addition, the present disclosure fulfills the need for alternative inhibitors of IL-23p19 by providing human lipocalin muteins that bind human IL-23p19 and useful applications therefor. Accordingly, the disclosure also provides methods of making and using the IL-23p19-binding proteins described herein as well as compositions that may be used in methods of detecting IL-23p19 in a sample or in methods of binding of IL-23p19 in a subject. No such human lipocalin muteins having these features attendant to the uses provided by present disclosure have been previously described.

One embodiment of the current disclosure relates to a lipocalin mutein that is capable of binding Interleukin-23p19 (IL-23p19), with an affinity measured by a $K_D$ of about 1 nM or lower, such as about 0.6 nM, when measured in an assay essentially described in Example 6 or Example 13.

In some other embodiments, the lipocalin mutein is capable of inhibiting the binding of IL-23 to its receptor IL-23R with an IC50 value of about 0.55 nM or lower in a competition ELISA format essentially described in Example 8 or Example 14.

In some particular embodiments, lipocalin mutein is crossreactive with both human IL-23 and mouse IL-23.

In some still further embodiments, a lipocalin mutein of the disclosure is capable of inhibiting the binding of IL-23 to its receptor IL-23R. In some further embodiments, the lipocalin mutein has an average EC50 value at least as good as (i.e. where the difference is less than 1.0 nM) or superior to the average EC50 value of of a benchmark antibody, when said lipocalin mutein and the benchmark antibody are measured in an assay essentially as described in Example 10 or Example 15. In some embodiments, the benchmark antibody is a polypeptide comprising (i) SEQ ID NO: 57 or 59 as the first subunit and (ii) SEQ ID NO: 58 or 60 as the second subunit. The lipocalin mutein may have an average EC50 value of about 1.2 nM or even lower in the assay when at the same time the benchmark antibody has an EC50 value of about 3 nM or lower in the assay, such as about 1.2 nM.

In some other embodiments, an IL-23p19-binding lipocalin mutein of the disclosure is more biophysically stable than the lipocalin mutein of SEQ ID NO: 44.

1. Exemplary Lipocalin Muteins with Binding-Affinity for Interleukin-23p19 (IL-23p19)

In one aspect, the present disclosure relates to novel, specific-binding human lipocalin 2 (Lcn2 or NGAL) muteins directed against or specific for Interleukin-23p19 (IL-23p19). Human lipocalin 2 muteins disclosed herein may be used for therapeutic and/or diagnostic purposes. A human lipocalin 2 mutein of the disclosure may also be designated herein as "a NGAL mutein". As used herein, a Tlc mutein of the disclosure "specifically binds" a target (here, IL-23p19) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In this regard, the disclosure provides one or more NGAL muteins that are capable of binding Interleukin-23p19 (IL-23p19) with an affinity measured by a KD of about 10 nM or lower. More preferably, the NGAL muteins can have an affinity measured by a KD of about 1 nM or lower.

In some embodiments, an hNGAL mutein of the disclosure includes at one or more positions corresponding to position 28, 36, 40-41, 49, 52, 65, 68, 70, 72-73, 75-77, 79, 81, 87, 96, 98, 100, 103, 106, 114, 120, 125, 127, 134 and 175 of the linear polypeptide sequence of the mature hNGAL (SEQ ID NO: 43) a substitution.

In particular embodiments, a lipocalin mutein of the disclosure comprises at least 1, 2, 3, 4, 5, 6, 7, 8, 9, 10, 11, 12, 13, 14, 15, 16, 17, 18, 19, 20, 21, or even more, substitution(s) at a sequence position corresponding to sequence position 28, 36, 40-41, 49, 52, 65, 68, 70, 72-73, 75-77, 79, 81, 87, 96, 98, 100, 103, 106, 114, 120, 125, 127, 134 and 175 of the linear polypeptide sequence of the mature hNGAL (SWISS-PROT Data Bank Accession Number P80188; SEQ ID NO: 43). Preferably, it is envisaged that the disclosure relates to a lipocalin mutein which comprises, in addition to one or more substitutions at positions corresponding to positions 36, 87 and/or 96 of the linear polypeptide sequence of the mature human NGAL, at one or more positions corresponding to positions position 28, 36, 40-41, 49, 52, 65, 68, 70, 72-73, 75-77, 79, 81, 87, 96, 98, 100, 103, 106, 114, 120, 125, 127, 134 and 175 of the linear polypeptide sequence of the mature hNGAL a substitution.

In some still further embodiments, the disclosure relates to a polypeptide, wherein said polypeptide is an hNGAL mutein, in comparison with the linear polypeptide sequence of the mature hNGAL, comprising at least 1, 2, 3, 4, 5, 6, 7, 8, 9, 10, 11, 12, 13, 14, 15, 16, 17, 18, 19, 20, 21, or even more, mutated amino acid residues at the sequence positions position 28, 36, 40-41, 49, 52, 65, 68, 70, 72-73, 75-77, 79, 81, 87, 96, 98, 100, 103, 106, 114, 120, 125, 127, 134 and 175, and wherein said polypeptide binds IL-23p19, in particular human IL-23p19.

In some embodiments, an IL-23p19-binding hNGAL mutein of the disclosure includes, at any one or more of the sequence positions 28, 36, 40-41, 49, 52, 65, 68, 70, 72-73, 75-77, 79, 81, 87, 96, 98, 100, 103, 106, 114, 120, 125, 127, 134 and 175 of the linear polypeptide sequence of the mature hNGAL (SEQ ID NO: 43), one or more of the following mutated amino acid residues: Gln 28→His; Leu 36→Giu; Ala 40→Leu; Ile 41→Leu; Gln 49→Arg; Tyr 52→Thr; Asn 65→Asp; Ser 68→Arg; Leu 70→Giu; Arg 72→Gly; Lys 73→Ala or Via; Lys 75→Thr; Asp 77→Lys; Trp 79→Gln or Arg; Arg 81→Gly; Asn 96→Gly; Lys 98→Glu; Tyr 100→Met; Leu 103→Met; Tyr 106→Phe; Asn 114→Asp; Met 120→Ile; Lys 125→Tyr; Ser 127→Tyr; and Lys 134→Giu. In some embodiments, an hNGAL mutein of the disclosure includes two or more, such as 3, 4, 5, 6, 7, 8, 9, 10, 11, 12, even more or all mutated amino acid residues at these sequence positions of the mature hNGAL.

Additionally, an IL-23p19-binding hNGAL mutein according to the disclosure may also comprise the following substitution: Cys 87→Ser. Furthermore, an IL-23p19-binding hNGAL mutein according to the disclosure may also comprise the following substitution: Cys 76→Tyr or Arg. Furthermore, an IL-23p19-binding hNGAL mutein according to the disclosure may also comprise the following substitution: Cys 175→Ala.

In some additional embodiments, an hNGAL mutein of the disclosure, which binds to IL-23p19 includes the one of following sets of amino acid replacements in comparison with the linear polypeptide sequence of the mature hNGAL:

(a) Gln 28→His; Leu 36→Giu; Ala 40-Leu; Ile 41→Leu; Gln 49→Arg; Tyr 52→Thr; Asn 65→Asp; Ser 68→Arg; Leu 70→Giu; Arg 72→Gly; Lys 73→Ala; Lys 75→Thr; Cys 76→Tyr; Asp 77→Lys; Trp 79→Gln; Arg 81→Gly; Asn 96→Gly; Lys 98→Giu; Tyr 100→Met; Leu 103→Met; Tyr 106→Phe; Met 120→Ile; Lys 125→Tyr; Ser 127→Tyr; and Lys 134→Giu;

(b) Gln 28→His; Leu 36→Giu; Ala 40-Leu; Gln 49→Arg; Tyr 52→Thr; Asn 65→Asp; Ser 68→Arg; Leu 70→Giu; Arg 72→Gly; Lys 73→Vla; Lys 75→Thr; Cys 76→Arg; Asp 77→Lys; Trp 79→Arg; Arg 81→Gly; Asn 96→Gly; Tyr 100⊖Met; Leu 103→Met; Tyr 106→Phe; Lys 125→Tyr; Ser 127→Tyr; and Lys 134→Giu; or (c) Gln 28→His; Leu 36→Giu; Ala 40-Leu; Ile 41→Leu; Gln 49→Arg; Tyr 52→Thr; Asn 65→Asp; Ser 68→Arg; Leu 70→Giu; Arg 72→Gly; Lys 73→Val; Lys 75→Thr; Cys 76→Tyr; Asp 77→Lys; Trp 79→Gln; Arg 81→Gly; Asn 96→Gly; Tyr 100→Met; Leu 103→Met; Tyr 106→Phe; Asn 114→Asp; Lys 125→Tyr; Ser 127→Tyr; and Lys 134→Giu.

In the residual region, i.e. the region differing from sequence positions 28, 36, 40-41, 49, 52, 65, 68, 70, 72-73, 75-77, 79, 81, 87, 96, 98, 100, 103, 106, 114, 120, 125, 127, 134 and 175, an hNGAL mutein of the disclosure may include the wild type (natural) amino acid sequence outside the mutated amino acid sequence positions.

In further particular embodiments, a lipocalin mutein according to the current disclosure comprises an amino acid sequence selected from the group consisting of SEQ ID NOs: 2 and 45-46 or a fragment or variant thereof.

The amino acid sequence of an IL-23p19-binding hNGAL mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 2 and 45-46.

The disclosure also includes structural homologues of an hNGAL mutein having an amino acid sequence selected from the group consisting of SEQ ID NOs: 2 and 45-46, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said hNGAL mutein.

In some particular embodiments, the present disclosure provides a lipocalin mutein that binds IL-23p19 with an affinity measured by a $K_D$ of about 1 nM or lower, wherein the lipocalin mutein has at least 90% or higher, such as 95%, identitiy to the amino acid sequence of SEQ ID NO: 2.

2. Applications of Lipocalin Muteins with Binding-Affinity for Interleukin-23p19 (IL-23p19)

Interleukin-23 (IL-23) is a heterodimeric cytokine composed of a unique subunit, p19 (herein referred to interchangeably as "IL-23p19"), and the p40 subunit, which is shared with interleukin-12 (IL-12) (Oppmann, Immunity 13:115 (2000)). IL-23 has been found to stimulate the production and/or maintenance of IL-17A and IL-17F from activated CD4 T cells in what has now been termed as a "new" T-helper (Th) subset, designated Thl 7. A review of IL-23 cytokine and receptor biology is reviewed in Holscher, Curr. Opin. Invest. Drugs 6:489 (2005) and Langrish et al. Immunol Rev. 202:96 (2004). Similar to Thl and Th2 lineages, Thl7 cells have most likely evolved to provide adaptive immunity to specific classes of pathogens, such as extracellular bacteria. However, inappropriate Th 17 responses have been strongly implicated in a growing list of autoimmune disorders, including multiple sclerosis, rheumatoid arthritis, inflammatory bowel disease, and psoriasis.

In this regard, IL-23 promotes a distinct CD4 T cell activation state characterized by the production of interleukin-17 (J. Biol. Chem. 278:1910-191 (2003); see also Langrish et al). IL-23 drives a pathogenic T cell population that induces autoimmune inflammation (J. Exp. Med. 201: 233-240 (2005); Starnes et al. "Cutting edge: IL-17F, a novel cytokine selectively expressed in activated T cells and monocytes, regulates angiogenesis and endothelial cell cytokine production" J. Immunol. 167:4137-4140 (2001)).

Numerous possible applications for the muteins with binding-affinity for IL-23p19 of the disclosure, therefore, exist in medicine. In one further aspect, the disclosure relates to the use of such a mutein disclosed for detecting IL-23p19 in a sample as well as a respective method of diagnosis.

The present disclosure also involves the use of one or more muteins with binding-affinity for IL-23p19 as described for complex formation with IL-23p19.

Therefore, in another aspect of the disclosure, the disclosed muteins are used for the detection of IL-23p19. Such use may include the steps of contacting one or more said muteins, under suitable conditions, with a sample suspected of containing IL-23p19, thereby allowing formation of a complex between the muteins and IL-23p19, and detecting the complex by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins disclosed herein may also be used for the separation of IL-23p19. Such use may include the steps of contacting one or more said muteins, under suitable conditions, with a sample supposed to contain IL-23p19, thereby allowing formation of a complex between the muteins and IL-23p19, and separating the complex from the sample.

In the use of the disclosed muteins for the detection of IL-23p19 as well as the separation of IL-23p19, the muteins and/or IL-23p19 or a domain or fragment thereof may be immobilized on a suitable solid phase.

Accordingly, the presence or absence of a molecule such as IL-23p19, e.g., in a sample, as well as its concentration or level may be determined.

In still another aspect, the present disclosure features a diagnostic or analytical kit comprising a mutein with binding-affinity for IL-23p19 according to the disclosure.

In addition to their use in diagnostics, in yet another aspect, the disclosure encompasses the use of such a mutein of the disclosure or a composition comprising such mutein for the binding of IL-23p19 in a subject and/or inhibiting the binding of IL-23 to its receptor in a subject.

In still another aspect, the present disclosure features a method of binding IL-23p19 in a subject, comprising administering to said subject an effective amount of one or more lipocalin muteins with binding-affinity for IL-23p19 of the disclosure or of one or more compositions comprising such a mutein.

In still another aspect, the present disclosure involves a method for inhibiting the binding of IL-23 to its receptor in a subject, comprising administering to said subject an effective amount of one or more lipocalin muteins with binding-affinity for IL-23p19 of the disclosure or of one or more compositions comprising such a mutein.

C. Compositions Comprising an IL-17A Binding Lipocalin Mutein and/or an IL-23p19 Binding Lipocalin Mutein and Uses of the Lipocalin Muteins IL-17A and IL-23 are cytokines involved in inflammation. Human interleukin-17A (also known as "IL-17", including IL-17 A/A and IL-17 A/F) is a cytokine which stimulates the expression of interleukin-6 (IL-6), intracellular adhesion molecule 1 (ICAM-I), interleukin-8 (IL-8), granulocyte macrophage colony-stimulating factor (GM-CSF), and prostaglandin E2 expression, and plays a role in the preferential maturation of CD34+ hematopoietic precursors into neutrophils (Yao et al, J. Immunol 755:5483 (1995); Fossiez et al, J. Exp. Med. 183:2593 (1996)). Human interleukin-23 (also known as "IL-23") is a cytokine which has been reported to promote the proliferation of T cells, in particular memory T cells.

Both IL-17A (including IL-17A in complex with IL-17F, also termed as IL-17 A/F) and IL-23 have been reported to play important roles in many autoimmune diseases, such as multiple sclerosis, rheumatoid arthritis, Crohn's disease, and psoriasis. Both IL-23 and IL-17A are overexpressed in the central nervous system of humans with multiple sclerosis and in mice undergoing an animal model of multiple sclerosis, experimental autoimmune encephalomyelitis (EAE). The overexpression is observed in mice when the EAE is induced by either myelinoligodendrocyte glycoprotein (MOG) 35-55 peptide- or proteolipid peptide (PLP). Furthermore, neutralization of either IL-23p19 or IL-17A results in amelioration of EAE symptoms in mice (Park et al., Immunol 6:1133 (2005); Chen et al., J Clin Invest. 116:1317 (2006)).

It has also been demonstrated that IL-17A and Th17 cells can be produced from IL-23-independent sources, and the in vivo development of an IL-17 effector response has been shown to be IL-23-independent (Mangan et al., Nature 441:231 (2006)). Neutralization of IL-23 would theoretically eliminate existing IL-17A producing cells, but would not completely prevent the development of new Th17 cells.

The present disclosure, therefore, concerns the binding of both of these proinflammatory cytokines, IL-17A and IL-23p19, since binding both IL-23 (via p19) and IL-17A is more effective therapeutically than neutralization of IL-23p19 alone or IL-17A alone and thus, beneficial for the effective treatment of inflammatory diseases.

Although antibodies against IL-17A and/or IL-23p19 have been described, these antibody-based approaches still have a number of serious drawbacks such as the necessity of complex mammalian cell production systems, a dependency on disulfide bond stability, the tendency of some antibody fragments to aggregate, limited solubility and last but not least, they may elicit undesired immune responses even when humanized. There is an unmet need to, therefore, to develop small globular proteins such as lipocalins as scaffolds for the generation of a novel class of IL-17A or IL-23p19 binding proteins, e.g. lipocalin muteins with binding-affinity for IL-17A or IL-23p19.

Accordingly, it is an object of the present disclosure to provide human lipocalin muteins that bind IL-17A (including IL-17 A/A and IL-17 A/F) and/or IL-23p19 and can be used in pharmaceutical applications. The disclosure also provides one or more compositions comprising such lipocalin muteins and, optionally, one or more pharmaceutically or diagnostically acceptable excipients (e.g. adjuvants, diluents or carriers). Lipocalin muteins of the disclosure as well as compositions thereof may be used in methods of detecting IL-17A (including IL-17 A/A and IL-17 A/F) and/or IL-23p19 in a sample or in methods of binding of IL-17A (including IL-17 A/A and IL-17 A/F) and/or IL-23p19 in a subject.

As discussed above, binding IL-17A (including IL-17 A/A and IL-17 A/F) and IL-23p19 concomitantly with lipocalin muteins specific for IL-17A (including IL-17 A/A and IL-17 A/F) or IL-23p19, respectively, could overcome some of the hypoxia-mediated effects that binding IL-17A (including IL-17 A/A and IL-17 A/F) alone or binding IL-23p19 alone, respectively, might induce. The present disclosure, therefore, encompasses use of (i) a first lipocalin mutein specific for IL-17A and (ii) a second lipocalin mutein specific for IL-23p19, for the binding of IL-17A and IL-23p19 in a subject. Such use includes a step of administering to a subject an effective amount of (i) a first lipocalin mutein specific for IL-17A and (ii) a second lipocalin mutein specific for IL-23p19.

In the context of the present disclosure, the lipocalin mutein specific for IL-17A can binds to IL-17A that exists as a homodimer (i.e. IL-17 A/A), but it can also binds to IL-17A that exists as a heterodimer complexed with the homolog IL-17F to form heterodimeric IL-17 A/F. In one preferred embodiment, said lipocalin mutein binds to IL-17A and IL-17F complex.

The first lipocalin mutein and the second lipocalin mutein may be administered in combination, including concurrently, concomitantly or in series. In some embodiments, the first lipocalin mutein and the second lipocalin mutein may be included in a composition that may be administered. The composition may include an effective amount of the first and the second lipocalin mutein as active ingredients, in association with at least one pharmaceutically acceptable adjuvant, diluent or carrier. The first lipocalin mutein and the second lipocalin mutein may also be administered independent from each other, including at individual intervals at independent points of time.

In some embodiments, the present disclosure also relates to a composition comprising a first lipocalin mutein specific for IL-17A and (ii) a second lipocalin mutein specific for IL-23p19, which composition can be used in a method of binding of IL-17A and IL-23p19 e.g. in a subject. In addition, such composition may be used in a method of detecting IL-17A (including IL-17 A/A and IL-17 A/F) and IL-23p19 e.g. in a sample.

In some other embodiments, the present disclosure relates to a combination of a first lipocalin mutein and a second lipocalin mutein. One of these lipocalin muteins can bind to IL-17A as a given non-natural target with detectable affinity. The other lipocalin mutein can bind to IL-23p19 as a given non-natural target with detectable affinity. The respective lipocalin mutein thus binds to IL-17A or to IL-23p19, respectively, as a given non-natural target. The term "non-natural target" refers to a compound, which does not bind to the corresponding lipocalin under physiological conditions. For example, the first lipocalin mutein can bind to IL-17A and the second lipocalin mutein can bind to IL-23p19, or vice versa. The combination of the first lipocalin mutein and the second lipocalin mutein may be provided in various forms.

In some embodiments, the lipocalin mutein specific for IL-17A as used in the disclosure is able to bind IL-17A with detectable affinity, i.e. with a dissociation constant of at least 200 nM, including about 100 nM, about 50 nM, about 25 nM or about 15 nM. In some embodiments, the lipocalin mutein specific for IL-23p19 as used in the disclosure is able to bind IL-23p19 with detectable affinity, i.e. with a dissociation constant of at least 200 nM including about 100 nM, about 50 nM, about 25 nM or about 15 nM. In some further preferred embodiments, a lipocalin mutein of the combination according to the disclosure binds IL-17A or IL-23p19, respectively, with dissociation constant for IL-17A or IL-23p19 of at least about 10 nM, about 1 nM, about 0.1 nM, about 10 pM, or even lower. The present disclosure, thus, provides a combination of (i) a mutein of a lipocalin that has a particularly high affinity to IL-17A and (ii) a mutein of a lipocalin that has a particularly high affinity to IL-23p19.

In some embodiments, the lipocalin muteins with a detectable affinity for IL-17A are muteins of human tear lipocalin. These and further details on lipocalin muteins with a detectable affinity for IL-17A can be found in Section A of the current disclosure.

In a particularly preferred embodiment, a lipocalin mutein that is specific for IL-17A is shown in SEQ ID NO: 1.

In some embodiments, the lipocalin muteins with a detectable affinity for IL-23p19 are muteins of human tear lipocalin or muteins of human neutrophil gelatinase associated lipocalin. These and further details of lipocalin muteins with a detectable affinity for IL-23p19 have been disclosed in in Section B of the current disclosure.

In a particular preferred embodiment, the lipocalin mutein that is specific for IL-23p19 is shown in any one of SEQ ID NOs: 2, 45 and 46.

In still another aspect, the present disclosure features a method of binding IL-17A and IL-23 in a subject comprising administering to said subject an effective amount of (i) a first lipocalin mutein specific for IL-17A and (ii) a second lipocalin mutein specific for IL-23p19.

In still another aspect, the present disclosure involves a method for inhibiting the binding of IL-17A and IL-23 to their respective receptor(s) in a subject comprising administering to said subject an effective amount of (i) a first lipocalin mutein specific for IL-17A and (ii) a second lipocalin mutein specific for IL-23p19.

The present disclosure also involves the use of (i) a first lipocalin mutein specific for IL-17A and (ii) a second lipocalin mutein specific for IL-23p19 for complex formation with IL-17A and IL-23p19.

Therefore, in another aspect of the disclosure, the disclosed muteins can be used for the detection of IL-17A and IL-23p19. Such use may include the steps of contacting two or more said muteins, under suitable conditions, with a sample suspected of containing IL-17A and IL-23p19, thereby allowing formation of a complex between the muteins and IL-17A or between the muteins and IL-23p19, respectively, and detecting the complex by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins disclosed herein may also be used for the separation of IL-17A and IL-23p19. Such use may include the steps of contacting one or more said muteins, under suitable conditions, with a sample supposed to contain IL-17A and IL-23p19, thereby allowing formation of a complex between the muteins and IL-17A or between the muteins and IL-23, respectively, and separating the complex from the sample.

In the use of the disclosed muteins for the detection of IL-17A and IL-23p19 as well as the separation of IL-17A and IL-23p19, the muteins and/or IL-17A and IL-23p19 or a domain or fragment thereof may be immobilized on a suitable solid phase.

Accordingly, the presence or absence of IL-17A and/or IL-23p19, e.g., in a sample, as well as their concentration or level may be determined.

In another aspect, the disclosure provides for a kit of parts. The kit includes a first and a second container. The first container includes the first lipocalin mutein and the second container includes the second lipocalin mutein. In one aspect, the disclosure relates to a kit that includes, in one or more containers, separately or in admixture, a lipocalin mutein specific for IL-17A. In yet another aspect, the disclosure also relates to a kit that includes, in one or more containers, separately or in admixture, a lipocalin mutein specific for IL-23p19. In some embodiments, the disclosure relates to a kit that includes, in one or more containers, separately or in admixture, a lipocalin mutein specific for IL-17A and a lipocalin mutein specific for IL-23p19. In some further preferred embodiments, the kid comprises a first container that includes a first lipocalin mutein specific for IL-17A and a second container that includes a second lipocalin mutein specific for IL-23p19. In some embodiments the kit further includes integrally thereto or as one or more separate documents, information pertaining to the contents or the kit and the use of the lipocalin muteins. The kit may include in some embodiments one or more compositions that are formulated for reconstitution in a diluent. Such a diluent, e.g. a sterile diluent, may also be included in the kit, for example within a container.

D. Fusion Proteins with Binding Affinity for IL-17A and/or IL-23p19 and Uses Thereof In one aspect, the present disclosure relates to a fusion protein comprising at least two subunits in any order: one subunit has binding specificity for IL-17A and another subunit has binding specificity for IL-23p19.

For example, the present disclosure provides a fusion protein that has protein moieties with binding specificity for IL-17A (including IL-17 A/A and IL-17 A/F) and IL-23p19, respectively. In this regard, one subunit of said fusion protein may comprise a lipocalin mutein of the disclosure specific for IL-17A (including IL-17 A/A and IL-17 A/F) while another subunit of said fusion protein may comprise a lipocalin mutein of the disclosure specific for IL-23p19.

In another aspect, the present disclosure is pertinent to a fusion protein comprising at least two subunits, where each has a binding specificity for IL-17A (including IL-17 A/A and IL-17 A/F). In some embodiments, at least one subunit comprises a lipocalin mutein specific for IL-17A. In some embodiments, the fusion protein has a binding affinity for IL-17A by a KD of about 1 nM or lower in an assay essentially described in Example 2. In some additional embodiments, the fusion protein is capable of inhibiting the binding of IL-17A to its receptor in a competition ELISA format essentially described in Example 3 or in an assay essentially described in Example 5.

In some further embodiments, each of the two subunits comprises a lipocalin mutein specific for IL-17 A/A. In some further embodiments, each of the two subunits comprises a lipocalin mutein specific for IL-17 A/F. The two lipocalin muteins may have a different amino acid sequence. Hence, in some embodiment, the two lipocalin muteins bind to a different epitope on IL-17A. In some other embodiments, however, the two lipocalin muteins may be identical to each other. For example, such a fusion protein may comprise two I amino acid sequences of SEQ ID NO: 1. In this regard, the fusion protein may have the amino acid sequence shown in SEQ ID NO: 10, SEQ NO: 12 or SEQ ID NO: 13.

In some embodiments, a fusion protein of the disclosure having two subunits that have binding specificity to IL-17A (including IL-17 A/A and IL-17 A/F) may exhibit a higher potency than a single subunit, due to an avidity effect of the two subunits, which is brought about by the dimeric nature of the target (e.g. IL17 A/A). In this regard, the fusion protein can be a bivalent fusion protein. In still another aspect, the present disclosure also encompasses a fusion protein comprising at least two subunits that have binding specificity for IL-23p19. In some embodiments, at least one subunit comprises a lipocalin mutein specific for IL-23p19. In some embodiments, the fusion protein has a binding affinity for IL-23p19 by a KD of about 10 nM or lower in an assay essentially described in Example 7. In some additional embodiments, the fusion protein is capable of inhibiting the binding of IL-23 to its receptor in a competition ELISA format essentially described in Example 8 or Example 14 or in an assay essentially described in Example 10 or Example 15.

In some further embodiments, each of the two subunits comprises a lipocalin mutein specific for IL-23p19. The two lipocalin muteins may have a different amino acid sequence. Hence, in some embodiment, the two lipocalin muteinsbind to a different epitope on IL-23p19. In some other embodiments, however, the two lipocalin muteins may be identical to each other.

In one further aspect, the present application discloses a fusion protein comprising (i) the Fc part of an immunoglobulin, including a full-length human antibody, such as an IgG antibody, and (ii) a lipocalin mutein specific for IL-17A.

In another aspect, the present application discloses a fusion protein comprising (i) the Fc part of an immunoglobulin, including a full-length human antibody, such as an IgG antibody, and (ii) a lipocalin mutein specific for IL-23p19.

Exemplary lipocalin muteins specific for IL-17A (including IL-17 A/A and IL-17 A/F) include those disclosed in Section A of the current disclosure. In a particularly preferred embodiment, the lipocalin mutein is shown in SEQ ID NO: 1.

Exemplary lipocalin muteins specific for IL-23p19 include those disclosed in Section B of the current disclosure. In a particularly preferred embodiment, the lipocalin mutein is shown in any one of the SEQ ID NOs: 2, 45 and 46.

In some particular embodiments, the lipocalin mutein can be linked, for example, via a peptide bond, to the C-terminus and/or the N-terminus of the Fc part of a human antibody (see FIG. 11). In a particular embodiment, a fusion protein of the disclosure may comprise a lipocalin mutein attached to the Fc part of an IgG antibody. In this regard, one of such fusion proteins comprises the amino acid sequences shown in SEQ ID NO: 16.

In a still preferred embodiment, a fusion protein of the disclosure comprises the amino acids shown in SEQ ID NO: 11, SEQ ID NO: 12 or SEQ ID NO: 13.

In a related embodiment, one or more fusion proteins of the disclosure are capable of inhibiting the binding of IL-17A and the binding of IL-23 to their respective receptor(s). In some further embodiments, one or more fusion proteins of the disclosure are capable of engaging IL-17A and IL-23p19 simultaneously, and, hence, thereby are capable of inhibiting the binding of IL-17A and the binding of IL-23 to their respective receptor(s) at the same time.

In this aspect, the present disclosure relates to a fusion protein comprising at least two subunits in any order, including one subunit comprises a lipocalin mutein specific for IL-17A (including IL-17 A/A and IL-17 A/F) and one subunit comprises a lipocalin mutein specific for IL-23p19. In some further embodiments, the fusion protein may contain an additional subunit, which subunit comprises a lipocalim mutein specific for IL-17A (including IL-17 A/A and IL-17 A/F) or IL-23p19. In some embodiments, two IL-17A-specific lipocalin muteins, as included in two different subunits of the fusion protein, may bind to different epitopes on the IL-17A target; alternatively, the two IL-17A-specific lipocalin muteins, as included in two different subunits of the fusion protein, may have the same amino acid sequence and, hence, have the specificity for the same epitope on the IL-17A target. A fusion protein of the disclosure having two subunits binding to IL-17A may exhibit a stronger binding to IL-17A than a fusion protein having only one subunit binding to IL-17A, due to an avidity effect brought about by the dimeric nature of the target. Likewise, two IL-23p19-specific lipocalin muteins, as included in two different subunits of the fusion protein, may bind to different epitopes on the IL-23p19 target; alternatively, the two IL-23p19-specific lipocalin mutein, as included in two different subunits of the fusion protein, may have the same amino acid sequence and, hence, the specificity for the same epitope on the IL-23p19 target. A fusion protein may also include a linker that links one subunit to another subunit.

In some embodiments, one subunit of a fusion protein of the disclosure comprises a lipocalin mutein disclosed in Section A of the current disclosure. In a particularly preferred embodiment, the subunit comprises a lipocalin mutein shown in SEQ ID NO: 1.

In some embodiments, one subunit of a fusion protein of the disclosure comprises a lipocalin mutein disclosed in in Section B of the current disclosure. In a particular preferred embodiment, the subunit comprises a lipocalin mutein shown in any one of the SEQ ID NOs: 2, 45 and 46.

In some embodiments, a fusion protein of the disclosure comprises a lipocalin mutein disclosed in Section A as well as a lipocalin mutein disclosed in in Section B.

In a particular embodiment, a fusion protein of the disclosure comprises the amino acid sequence shown in SEQ ID NO: 3.

In a particular embodiment, a fusion protein of the disclosure comprises the amino acid sequence shown in SEQ ID NO: 4.

In a still preferred embodiment, a fusion protein of the disclosure comprises the amino acids shown in SEQ ID NO: 12 or SEQ ID NO: 13.

In another aspect, the present application discloses a fusion protein comprising at least two subunits, wherein one subunit has binding specificity for IL-17A or IL-23p19 and another subunit contains an albumin binding domain (ABD) or an albumin binding peptide. In some embodiments, the subunit has binding specificity for IL-17A or IL-23p19 comprises a lipocalin mutein specific for IL-17A or IL-23p19 of the disclosure. Furthermore, the fusion protein may comprise in any order (i) one subunit specific for IL-17A, (ii) one subunit specific for IL-23p19 and (iii) one subunit that contains a bacterial albumin binding domain. In some embodiments, the subunit has binding specificity for IL-17A comprises a lipocalin mutein specific for IL-17A of the disclosure. In some other embodiments, the subunit has binding specificity for IL-23p19 comprises a lipocalin mutein specific for IL-23p19 of the disclosure.

In some embodiments, the albumin binding domain (ABD) may be a streptococcal protein G (König, T., & Skerra, A. (1998) *J. Immunol. Methods* 218, 73-83) or a fragment thereof, e.g. as shown in SEQ ID NO: 14. In some other embodiments, the albumin binding peptide is a human serum albumin binding peptide derived from the albumin binding domain of streptococcal protein G, for example, as disclosed in PCT application WO2012/004384, which is incorporated by reference its entirety herein. In some still preferred embodiments, the albumin binding peptide comprises the amino acid sequence shown in SEQ ID NO: 15.

In particular, the present disclosure provides a fusion protein, which is capable of binding to both human serum albumin (HSA) and IL-23p19 simultaneously, for example, comprising the amino acid sequence shown in SEQ ID NO: 7.

The present disclosure provides a fusion protein, which is capable of binding to both HSA and IL-17A simultaneously, for example, comprising the amino acid sequence shown in SEQ ID NO: 8 or SEQ ID NO: 10. In some still preferred embodiment, such fusion protein may include two IL-17A-specific lipocalin muteins, for example, comprising the amino acid sequence shown in SEQ ID NO: 10.

In addition, the present application features a fusion protein, which is capable of binding to all HSA, IL-17A and IL-23p19 simultaneously, for example, when the fusion protein is measured in an assay essentially described in Example 12, In some further embodiments, the fusion protein comprises the amino acid sequence shown in SEQ ID NO: 5, SEQ ID NO: 6 or of SEQ ID NO: 9. In some still preferred embodiment, such fusion protein may include two IL-17A-specific lipocalin muteins, for example, comprising the amino acid sequence shown in SEQ ID NO: 6.

In an additional aspect, the present disclosure relates to a fusion protein comprising at least two subunits in any order: one subunit has binding specificity for IL-17A or has binding specificity for IL-23p19 and another subunit has binding specificity for TNF, for example, comprising a TNF-inhibiting protein. Tumor necrosis factors (or the TNF family) refer to a group of cytokines that can cause cell death (apoptosis) such as TNF-alpha (TNF-α) and Lymphotoxin-alpha. Exemplary TNF inhibitors include adalimumab, infliximab, etanercept, certolizumab pegol and golimumab. In some further embodiments, the TNF-specific subunit comprises an anti-TNF-α antibody, such as the antibody of SEQ ID NOs: 61 and 62. In some additional embodiments, the subunit has binding specificity for IL-17A or has binding specificity for IL-23p19 comprises a lipocalin mutein of the disclosure such as the lipocalin of SEQ ID NO: 1 or the lipocalin of SEQ ID NO: 2. In some still further embodiments, the fusion proteins comprises the amino acid sequences of SEQ ID NOs: 63 and 62 or the amino acid sequences of SEQ ID NOs: 64 and 62.

In some embodiments, the fusion protein is capable of binding 17A and, in some preferred embodiments, may have an average EC50 value at least as good as or superior to the average EC50 value of the lipocalin mutein as included in the fusion protein, for example, when the fusion protein and the lipocalin mutein are measured in an assay essentially described in Example 16. In some embodiments, the fusion protein is capable of binding IL-23 and in some preferred embodiments, may have an average EC50 value at least as good as or superior to the average EC50 value of the lipocalin mutein as included in the fusion protein, for example, when the fusion protein and the lipocalin mutein are measured in an assay essentially described in Example 17. In some embodiments, the fusion protein is capable of binding TNF-α and, in some preferred embodiments, may have an average EC50 value at least as good as or superior to the average EC50 value of the antibody as included in the fusion protein, when the antibody and the fusion protein are measured in an assay essentially described in Example 18. In some further embodiments, the fusion protein may be capable of binding to all TNF-α, IL-17A and IL-23p19 simultaneously, for example, when the fusion protein is measured in an assay essentially described in Example 19.

In some embodiments, a fusion protein of the disclosure has a binding affinity for IL-17A (including IL-17 A/A and IL-17 A/F) measured by a KD of about 1 nM or lower. More preferably, said fusion protein may have an affinity measured by a KD of 0.1 nM or lower. In some further embodiments, the IL-17A-binding moiety (or moieties) of a fusion protein of the disclosure may have a binding affinity or inhibiting ability for IL-17A (including IL-17 A/A and IL-17 A/F) as good as that of such moiety as a stand-alone polypeptide (see Table 1).

In some embodiments, a fusion protein of the disclosure has a binding affinity for IL-23p19 measured by a KD of about 10 nM or lower. More preferably, said fusion protein may have an affinity measured by a KD of about 1 nM or lower. In some further embodiments, the IL-23p19-binding moiety (or moieties) of a fusion protein of the disclosure may have a binding affinity or inhibiting ability for IL-23p19 as good as that of such moiety as a stand-alone polypeptide (see Table 1 below).

Table 1: provides an overview of the activity of individual lipocalin muteins SEQ ID NO: 1 and SEQ ID NO: 2, compared to their fusion proteins SEQ ID NO's: 3-13 in competition ELISA, surface plasmon resonance (SPR) and functional cell-based assays. Values were determined for interaction with IL-17 and/or IL-23, depending on whether the respective construct contains the IL-17A-binding lipocalin mutein SEQ ID NO: 1, the IL-23-binding lipocalin mutein SEQ ID NO: 2, or both. To determine the activity towards IL-17 and IL-23, respectively, competition ELISA experiments were carried out as described in Example 3 and/or Example 8, SPR experiment in reverse format—i.e. with the protein constructs immobilised on the sensor chip—were carried out as described in Example 2 and/or Example 6, and cell assays were based on either IL-17A-induced G-CSF secretion (Example 5) and/or IL-23 induced Ba/F3 cell proliferation (Example 10). Note that the reverse format SPR experiment performed to determine IL-23 affinity was carried out in the presence of unphysiologically high concentrations of NaCl, and that the values therefore do not reflect the affinity to IL-23 under physiological conditions, but serve to determine whether the relative affinity to IL-23 is different in the SEQ ID NO: 2-containing fusion proteins of SEQ ID NO's: 3-13, compared to the individual mutein SEQ ID NO: 2. Table 1 demonstrates that the IL-17A-binding activity of all fusions containing SEQ ID NO: 1 is at least as good as that of SEQ ID NO: 1 itself in all assay formats. SEQ ID NO: 1 can therefore flexibly be employed in any fusion protein without activity loss. The IL-23-binding activity of all fusions containing SEQ ID NO: 2 is very close to that of SEQ ID NO: 2 itself in all assay formats. SEQ ID NO: 2 can therefore flexibly be employed in any fusion protein without significant activity loss.

| SEQ ID | Competition ELISA (IC50, IL17A) cf. Example 3 | Biacore. rev. format (Kd, IL17AF) cf. Example 2 | G-CSF secretion (EC50, IL17A) cf. Example 5 | Competition ELISA (IC50, IL23) cf. Example 8 | Biacore. rev. format (Kd, IL23) cf. Example 7 | Cell proliferation (EC50, IL23) cf. Example 10 |
|---|---|---|---|---|---|---|
| SEQ ID NO: 1 | 0.08 nM (0.06-0.09) | 0.10 nM | 0.13 nM (0.17/0.1) | | | |
| SEQ ID NO: 2 | | | | 0.54 nM (0.26-0.83) | 2.9 | 1.2 nM (1.7/0.7) |
| SEQ ID NO: 8 | 0.10 nM (0.07-0.13) | 0.10 nM | | | | |
| SEQ ID NO: 7 | | | | 1.11 nM (0.69-1.53) | 2.4 | |
| SEQ ID NO: 10 | 0.05 nM (0.03-0.07) | 0.04 nM | 0.1 nM (0.15/0.04) | | | |
| SEQ ID NO: 3 | 0.04 nM (0.03-0.05) | 0.10 nM | 0.15 nM (0.21/0.09) | 0.64 nM (0.49-0.79) | 3.0 | 0.9 nM (1.1/0.6) |
| SEQ ID NO: 4 | 0.07 nM (0.05-0.09) | 0.08 nM | 0.24 nM (0.20/0.29) | 0.99 nM (0.69-1.29) | 2.0 | 2.8 nM (2.8/2.7) |
| SEQ ID NO: 5 | 0.05 nM (0.03-0.06) | 0.08 nM | 0.15 nM (0.20/0.10) | 1.09 nM (0.63-1.56) | 1.7 | n.d. |
| SEQ ID NO: 9 | 0.05 nM (0.04-0.07) | 0.09 nM | 0.16 nM (0.19/0.12) | 2.07 nM (0.91-3.22) | 1.9 | 2.1 nM (2.4/1.7) |
| SEQ ID NO: 6 | 0.04 nM (0.02-0.05) | 0.10 nM | 0.05 nM (0.06/0.04) | 0.97 nM (0.61-1.33) | 1.9 | 0.8 nM (0.9/0.7) |
| SEQ ID NO: 11 | 0.09 nM (0.06-0.12) | 0.07 nM | 0.06 ± 0.04 nM (n = 3) | | | |
| SEQ ID NO: 12 | 0.03 nM (0.01-0.04) | 0.04 nM | 0.05 ± 0.04 nM (n = 3) | | | |
| SEQ ID NO: 13 | 0.04 nM (0.03-0.05) | n.d. | 0.05 ± 0.04 nM (n = 3) | | | |

In a related embodiment, one or more fusion proteins of the disclosure are capable of inhibiting the binding of IL-17A to its receptor.

In a related embodiment, a fusion protein of the disclosure is capable of inhibiting the binding of IL-23 to its receptor.

In some embodiments, a fusion protein of the disclosure may also include a linker (e.g. a peptide bond) that covalently links a lipocalin mutein of the disclosure and another lipocalin mutein of the disclosure to each other. This can be achieved, for example, by expression of the linked lipocalin muteins as a single polypeptide connected by a peptide linker. A suitable peptide linker can be comprised of a stretch of amino acids of arbitrary length containing any amino acids, e.g. as described herein. A preferred linker design utilizes a repeated stretch of amino acids of glycines and serines following the formula (GxSy)n, where x is the number of glycine repeats and y the number of serine repeats in a building block that is repeated n times. The values of each of the variables x, y, and n can range from 0 to 100, preferably from 0 to 10. Non-limiting examples are hereby provided with SEQ ID NOs: 18-20.

In some other embodiments, chemical methods of covalently linking may be applied to link a lipocalin mutein of the disclosure to another lipocalin mutein of the disclosure. One example is the use of bifunctional linkers that allow reactive chemistry between the linker and an amino acid side chain, for example, between a maleimide and a free cysteine in a lipocalin mutein, or an activated carboxylic acid ester and a primary amine in the lipocalin mutein. This includes reaction with non-natural amino acid side chains that may be included during protein expression, and which provide a functionality that can be selectively derivatised. In some still further embodiments, "click" chemistry, such as the cycloaddtion of an azide and an alkine, may be used to link one or more subunits of a fusion protein of the disclosure.

In some further preferred embodiments, a fusion protein of the disclosure further comprises the amino acid sequence shown in any one of SEQ ID NOs: 18-20.

In some further embodiments, one subunit comprising a lipocalin mutein of the disclosure may be, directly or via a chemical linker attached, to another subunit comprising a lipocalin mutein of the disclosure in a fusion protein as disclosed herein.

In some still further embodiments, a lipocalin mutein of the disclosure can be fused either to the N- or C-terminus or to both the N- and the C-termini of another lipocalin mutein.

In some embodiments, each of the subunits as comprised in a fusion protein of disclosure, stay thermostable (e.g. can resist a melting temperature at a $T_m$ of at least 40° C.). In some embodiments, each of said three subunits, comprised in a fusion protein of disclosure, are with high cooperativity of unfolding with respect to one or more other subunits (e.g. eliminate partial unfolding, and thus significantly reducing their rate of degradation). This elimination of partial unfolding is termed "cooperative," because unfolding is an all-or-none process. In some further embodiments, one or more lipocalin muteins as included in the fusion protein can resist a melting temperature at a Tm of at least 50° C., at least 55° C., at least 60° C. or even higher. In some still further embodiments, one or more HSA component as included in the fusion protein can resist a melting temperature at a $T_m$ of at least 30° C., at least 35° C., at least 40° C. or even higher.

In some embodiments, the one or more fusion proteins of the disclosure comprise multimers: e.g., tetramers, trimers or dimers of the lipocalin muteins of the disclosure, wherein at least one lipocalin mutein is fused to at least one side (e.g. to the N-terminus) of another lipocalin mutein. In some further embodiments, multimeric fusion proteins may be preferred to the corresponding monomeric fusion protein. For example, a dimeric fusion protein of the disclosure binding to IL-17A may exhibit a stronger binding to IL-17A due to an avidity effect brought about by the dimeric nature of the target.

In some further embodiment, one or more fusion proteins of the disclosure result in the formation of "Duocalins" as described in Schlehuber, S., and Skerra, A. (2001), Duocalins, engineered ligand-binding proteins with dual specificity derived from the lipocalin fold. *Biol. Chem.* 382, 1335-1342, the disclosure of which is hereby incorporated by reference in its entirety.

In still another aspect, the disclosure encompasses the use of one or more fusion proteins of the disclosure or of one or more compositions comprising such proteins for the binding of IL-17A and/or IL-23p19 in a subject and/or inhibiting the binding of IL-17 and/or IL-23 to their respective receptor(s) in a subject.

In still another aspect, the present disclosure features a method of binding IL-17A and/or IL-23p19 in a subject, comprising administering to said subject an effective amount of one or more fusion proteins of the disclosure or of one or more compositions comprising such proteins.

In still another aspect, the present disclosure involves a method for inhibiting the binding of IL-17 and/or IL-23 to their respective receptor(s) in a subject, comprising administering to said subject an effective amount of one or more fusion proteins of the disclosure or of one or more compositions comprising such proteins.

Fusion proteins of the disclosure may also include a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences are known in the art. An illustrative signal sequence for secretion a polypeptide into the periplasm of *E. coli* is the OmpA-signal sequence.

The present disclosure also involves the use of one or more fusion proteins of the disclosure for complex formation with IL-17A and/or IL-23p19.

Therefore, in another aspect of the disclosure, one or more fusion proteins of the disclosure can be used for the detection of IL-17A and/or IL-23p19. Such use may include the steps of contacting one or more fusion proteins of the disclosure, under suitable conditions, with a sample suspected of containing IL-17A and/or IL-23p19, thereby allowing formation of a complex between the proteins and IL-17A and/or between the proteins and IL-23p19, respectively, and detecting the complex by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The one or more fusion proteins disclosed herein may also be used for the separation of IL-17A and/or IL-23p19 from a sample that contains other substances. Such use may include the steps of contacting one or more said fusion proteins, under suitable conditions, with a sample supposed to contain IL-17A and/or IL-23p19, thereby allowing formation of a complex between the proteins and IL-17A and/or between the proteins and IL-23, respectively, and separating the complex from the sample.

In the use of a disclosed fusion proteins for the detection of IL-17A and/or IL-23p19 as well as the separation of IL-17A and/or IL-23p19, the fusion protein, IL-17A, IL-23p19 and/or a domain or fragment thereof may be immobilized on a suitable solid phase.

Accordingly, the presence or absence of molecules such as IL-17A and/or IL-23p19, e.g., in a sample, as well as its concentration or level may be determined.

In another aspect, the disclosure provides for a kit comprising at least one fusion protein of the disclosure and one or more instructions for using the kit.

In some embodiments the kit further includes integrally thereto or as one or more separate documents, information pertaining to the contents or the kit and the use of the fusion proteins. The kit may include in some embodiments one or more fusion proteins of the disclosure that are formulated for reconstitution in a diluent. Such a diluent, e.g. a sterile diluent, may also be included in the kit, for example within a container.

In some embodiments, the one or more fusion proteins of the disclosure may be used in the treatment of several conditions where the suppression of the immune response is desired such as Rheumatoid arthritis, Psoriatic arthritis, Ankylosing spondylitis, Crohn's disease, Ulcerative colitis, Plaque psoriasis, and Juvenile idiopathic arthritis.

E. Lipocalin Mueteins and Fusion Proteins of the Disclosure

Lipocalins are proteinaceous binding molecules that have naturally evolved to bind ligands. Lipocalins occur in many organisms, including vertebrates, insects, plants and bacteria. The members of the lipocalin protein family (Pervaiz, S., & Brew, K. (1987) FASEB J. 1, 209-214) are typically small, secreted proteins and have a single polypeptide chain. They are characterized by a range of different molecular-recognition properties: their ability to bind various, principally hydrophobic molecules (such as retinoids, fatty acids, cholesterols, prostaglandins, biliverdins, pheromones, tastants, and odorants), their binding to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signalling, and the synthesis of prostaglandins. The lipocalins have also been implicated in the regulation of the immune response and the mediation of cell homoeostasis (reviewed, for example, in Flower, D. R. (1996) Biochem. J. 318, 1-14 and Flower, D. R. et al. (2000) Biochim. Biophys. Acta 1482, 9-24).

The lipocalins share unusually low levels of overall sequence conservation, often with sequence identities of less than 20%. In strong contrast, their overall folding pattern is highly conserved. The central part of the lipocalin structure consists of a single eight-stranded anti-parallel β-sheet closed back on itself to form a continuously hydrogen-bonded β-barrel. This β-barrel forms a central cavity. One end of the barrel is sterically blocked by the N-terminal peptide segment that runs across its bottom as well as three peptide loops connecting the β-strands. The other end of the β-barrel is open to the solvent and encompasses a target-binding site, which is formed by four flexible peptide loops. It is this diversity of the loops in the otherwise rigid lipocalin scaffold that gives rise to a variety of different binding modes each capable of accommodating targets of different size, shape, and chemical character (reviewed, e.g., in Flower, D. R. (1996), supra; Flower, D. R. et al. (2000), supra, or Skerra, A. (2000) Biochim. Biophys. Acta 1482, 337-350).

A lipocalin mutein according to the present disclosure may be a mutein of any chosen lipocalin. Examples of suitable lipocalins (also sometimes designated as "protein 'reference' scaffolds" or simply "scaffolds") of which a mutein may be used include, but are not limited to, tear lipocalin (lipocalin-1, von Ebner gland protein), retinol binding protein, neutrophil, lipocalin-type prostaglandin D-synthase, β-lactoglobulin, bilin-binding protein (BBP), apolipoprotein D (APO D), neutrophil gelatinase associated lipocalin (NGAL), tear lipocalin (Tlc), α2-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1). In related embodiments, the lipocalin mutein is selected from the group consisting of human neutrophil gelatinase associated lipocalin (NGAL), human tear lipocalin (Tlc), human apolipoprotein D (APO D) and the bilin-binding protein of *Pieris brassicae*.

When used herein in the context of the lipocalin muteins of the present disclosure that bind to IL-17A or IL-23p19, the term "specific for" includes that the lipocalin mutein is directed against, binds to, or reacts with IL-17A or IL-23p19, respectively. Thus, being directed to, binding to or reacting with includes that the lipocalin mutein specifically binds to IL-17A or IL-23p19, respectively. The term "specifically" in this context means that the lipocalin mutein reacts with an IL-17A protein or an IL-23p19 protein, as described herein, but essentially not with another protein. The term "another protein" includes any non-IL-17A or non-IL-23p19 protein, respectively, including proteins closely related to or being homologous to IL-17A or IL-23p19 against which the lipocalins disclosed herein are directed to. However, IL-17A or IL-23p19 proteins, fragments and/or variants from species other than human such as those described in the context of the definition "subject" are not excluded by the term "another protein". The term "does not essentially bind" means that the lipocalin mutein of the present disclosure does not bind another protein, i.e., shows a cross-reactivity of less than 30%, preferably 20%, more preferably 10%, particularly preferably less than 9, 8, 7, 6 or 5%. Whether the lipocalin specifically reacts as defined herein above can easily be tested, inter alia, by comparing the reaction of a lipocalin mutein of the present disclosure with IL-17A or IL-23p19 and the reaction of said lipocalin with (an) other protein(s). "Specific binding" can also be determined, for example, in accordance with Western blots, ELISA-, RIA-, ECL-, IRMA-tests, FACS, IHC and peptide scans.

The amino acid sequence of a lipocalin mutein according to the disclosure has a high sequence identity to respective lipocalin when compared to sequence identities with another lipocalin (see also above). In this general context the amino acid sequence of a lipocalin mutein of the combination according to the disclosure is at least substantially similar to the amino acid sequence of the corresponding lipocalin (the wild-type or reference lipocalin). A respective sequence of a lipocalin mutein of the combination according to the disclosure, being substantially similar to the sequences of the corresponding lipocalin, has in some to the wild-type (or reference) lipocalin, one or more amino acid embodiments at least 65%, at least 70%, at least 75%, at least 80%, at least 82%, at least 85%, at least 87%, at least 90% identity, including at least 95% identity to the sequence of the corresponding lipocalin. In this regard, a lipocalin mutein of the disclosure of course may contain, in comparison substitutions as described herein which renders the lipocalin mutein capable of binding to IL-17A or IL-23p19, respectively. Typically a mutein of a lipocalin includes one or more mutations—relative to the native sequence lipocalin—of amino acids in the four loops at the open end of the ligand binding site of the lipocalin (cf. above). As explained above, these regions are essential in determining the binding specificity of a lipocalin mutein for a desired target. As an illustrative example, a mutein derived from a polypeptide of tear lipocalin, NGAL lipocalin or a homologue thereof, may have one, two, three, four or more mutated amino acid residues at any sequence position in the N-terminal region and/or in the three peptide loops BC, DE, and FG arranged at the end of the β-barrel structure that is located opposite to the natural lipocalin binding pocket. As a further illustrative example, a mutein derived from a polypeptide of tear lipocalin or a homologue thereof, may have no mutated amino acid residues in peptide loop DE arranged at the end of the β-barrel structure, compared to wild type sequence of tear lipocalin.

A lipocalin mutein according to the disclosure includes one or more, such as two, three, four, five, six, seven, eight, nine, ten, eleven, twelve, thirteen, fourteen, fifteen, sixteen, seventeen, eighteen, nineteen or even twenty substitutions in comparison to the corresponding native lipocalin, provided that such a lipocalin mutein should be capable of binding to IL-17A or IL-23p19, respectively. For example, a lipocalin mutein can have a substitution at a position corresponding to a distinct position (i.e. at a corresponding position) of the wild-type lipocalin having the wild-type sequence of, for example, tear lipocalin, NGAL lipocalin, or any other lipocalin disclosed herein. In some embodiments a lipocalin mutein of the combination according to the disclosure includes at least two amino acid substitutions, including 2, 3, 4 or 5, sometimes even more, amino acid substitutions of a native amino acid by an arginine residue. Accordingly, the nucleic acid of a protein 'reference' scaffold as described herein is subject to mutagenesis with the aim of generating a lipocalin mutein which is capable of binding to IL-17A or IL-23p19, respectively.

Also, a lipocalin mutein of the present disclosure can comprise a heterologous amino acid sequence at its N- or C-Terminus, preferably C-terminus, such as a Strep-tag, e.g., Strep II tag without affecting the biological activity (binding to its target e.g. IL-17A or IL-23p19, respectively) of the lipocalin mutein. A preferred example of a tag is shown in SEQ ID NO: 17).

Likewise, a lipocalin mutein of the present disclosure may lack 1, 2, 3, 4 or more amino acids at its N-terminal end and/or 1, 2 or more amino acids at its C-terminal end, in comparison to the respective wild-type lipocalin; for example, SEQ ID NOs: 2-7 and 12-14.

Specifically, in order to determine whether an amino acid residue of the amino acid sequence of a lipocalin mutein different from a wild-type lipocalin corresponds to a certain position in the amino acid sequence of a wild-type lipocalin, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a wild-type lipocalin can serve as "subject sequence" or "reference sequence", while the amino acid sequence of a lipocalin different from the wild-type lipocalin described herein serves as "query sequence". The terms "reference sequence" and "wild type sequence" are used interchangeably herein.

In some embodiments a substitution (or replacement) is a conservative substitution. Nevertheless, any substitution—including non-conservative substitution or one or more from the exemplary substitutions listed below—is envisaged as long as the lipocalin mutein retains its capability to bind to IL-17A or IL-23p19, respectively, and/or it has an identity to the then substituted sequence in that it is at least 60%, such as at least 65%, at least 70%, at least 75%, at least 80%, at least 85% or higher identical to the "original" sequence.

Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

a. Alanine (Ala), Glycine (Gly);
b. Aspartic acid (Asp), Glutamic acid (Glu);
c. Asparagine (Asn), Glutamine (Gln);
d. Arginine (Arg), Lysine (Lys);
e. Isoleucine (Ile), Leucine (Leu), Methionine (Met), Valine (Val);
f. Phenylalanine (Phe), Tyrosine (Tyr), Tryptophan (Trp);
g. Serine (Ser), Threonine (Thr); and
h. Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gln→Giu; Giu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

Substantial modifications in the biological properties of the lipocalin are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, methionine, alanine, valine, leucine, iso-leucine; (2) neutral hydrophilic: cysteine, serine, threonine; (3) acidic: asparitic acid, glutamic acid; (4) basic: asparagine, glutamine, histidine, lysine, arginine; (5) residues that influence chain orientation: glycine, proline; and (6) aromatic: tryptophan, tyrosine, phenylalanine.

Non-conservative substitutions will entail exchanging a member of one of these classes for another class. Any cysteine residue not involved in maintaining the proper conformation of the respective lipocalin also may be substituted, generally with serine, to improve the oxidative stability of the molecule and prevent aberrant crosslinking. Conversely, cysteine bond (s) may be added to the lipocalin to improve its stability.

Any mutation, including an insertion as discussed above, can be accomplished very easily on the nucleic acid, e.g. DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) iso-leucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of tear lipocalin as long as these deletions or insertion result in a stable folded/functional mutein.

Modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein or a fusion protein for a given target. Furthermore, mutations can be introduced in order to modulate certain characteristics of the mutein or fusion protein such as to improve folding stability, serum stability, protein resistance or water solubility or to reduce aggregation tendency, if necessary. For example, naturally occurring cysteine residues may be mutated to other amino acids to prevent disulphide bridge formation. It is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. The generated thiol moiety may be used to PEGylate or HESylate the mutein or the fusion protein, for example, in order to increase the serum half-life of a respective lipocalin mutein or fusion protein.

In some embodiments, if one of the above moieties is conjugated to a lipocalin mutein or a fusion protein of the disclosure, conjugation to an amino acid side chain can be advantageous. Suitable amino acid side chains may occur naturally in the amino acid sequence of a human lipocalin or may be introduced by mutagenesis. In case a suitable binding site is introduced via mutagenesis, one possibility is the replacement of an amino acid at the appropriate position by a cysteine residue.

For example, such mutation includes at least one of Thr 40→Cys, Glu 73→Cys, Arg 90→Cys, Asp 95→Cys or Glu 131→Cys substitution in the wild type sequence of human tear lipocalin. The newly created cysteine residue at any of these positions can in the following be utilized to conjugate the mutein or the fusion protein to a moiety prolonging the serum half-life of the mutein or a fusion protein thereof, such as PEG or an activated derivative thereof.

With respect to a mutein of human Lipocalin 2, exemplary possibilities of such a mutation to introduce a cysteine residue into the amino acid sequence of a lipocalin including human Lipocalin 2 mutein to include the introduction of a cysteine (Cys) residue at at least at one of the sequence positions that correspond to sequence positions 14, 21, 60, 84, 88, 116, 141, 145, 143, 146 or 158 of the wild type sequence of human NGAL. In some embodiments where a human Lipocalin 2 mutein of the disclosure has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No P80188. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human Lipocalin 2 mutein or a fusion protein thereof.

In another embodiment, in order to provide suitable amino acid side chains for conjugating one of the above moieties to a lipocalin mutein or a fusion protein according to the present disclosure, artificial amino acids may be introduced by mutagenesis. Generally, such artificial amino acids are designed to be more reactive and thus to facilitate the conjugation to the desired compound. One example of such an artificial amino acid that may be introduced via an artificial tRNA is para-acetyl-phenylalanine.

For several applications of the muteins or fusion proteins disclosed herein it may be advantageous to use them in the form of conjugates, for example, as fused to a moiety which is a protein, or a protein domain or a peptide. In some embodiments, a lipocalin mutein or a fusion protein thereof is fused at the N-terminus or the C-terminus of the lipocalin mutein (including as comprised in a fusion protein of the disclosure) to a protein, a protein domain or a peptide, for instance, a signal sequence and/or an affinity tag.

Affinity tags such as the Strep-tag® or Strep-tag® II (Schmidt, T. G. M. et al. (1996) *J. Mol. Biol.* 255, 753-766), the myc-tag, the FLAG-tag, the His$_6$-tag or the HA-tag or proteins such as glutathione-S-transferase also allow easy detection and/or purification of recombinant proteins are further examples of suitable fusion partners. Finally, proteins with chromogenic or fluorescent properties such as the green fluorescent protein (GFP) or the yellow fluorescent protein (YFP) are suitable fusion partners for lipocalin muteins of the disclosure as well.

In general, it is possible to label the lipocalin muteins or fusion proteins of the disclosure with a compound including any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of X-rays when using a radioactive label. Alkaline phosphatase, horseradish peroxidase and β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the lipocalin muteins or fusion proteins of the disclosure. The lipocalin muteins or fusion proteins of the disclosure may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The lipocalin muteins or fusion proteins of the disclosure may, however, also be conjugated with therapeutically active nucleic acids such as antisense nucleic acid molecules, small interfering RNAs, micro RNAs or ribozymes. Such conjugates can be produced by methods well known in the art.

As indicated above, a lipocalin mutein or a fusion protein of the disclosure may in some embodiments be conjugated to a moiety that extends the serum half-life of the mutein or the fusion protein (in this regard see also PCT publication WO 2006/56464 where such conjugation strategies are described with references to muteins of human neutrophile gelatinase-associated lipocalin with binding affinity for CTLA-4). The moiety that extends the serum half-life may be a polyalkylene glycol molecule, hydroxyethyl starch, fatty acid molecules, such as palmitic acid (Vajo & Duckworth 2000, *Pharmacol. Rev.* 52, 1-9), an Fc part of an immunoglobulin, a CH3 domain of an immunoglobulin, a CH4 domain of an immunoglobulin, an albumin binding domain, an albumin binding peptide, or an albumin binding protein, transferrin to name only a few. The albumin binding protein may be a bacterial albumin binding protein, an antibody, an antibody fragment including domain antibodies (see U.S. Pat. No. 6,696,245, for example), or a lipocalin mutein with binding activity for albumin. Accordingly, suitable conjugation partner for extending the half-life of a lipocalin mutein or a fusion protein of the disclosure includes a bacterial albumin binding domain, such as the one of streptococcal protein G (König, T., & Skerra, A. (1998) *J. Immunol. Methods* 218, 73-83) or the one as shown in SEQ ID NO: 39. In addition, examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, His, lie, Leu, or Lys; Xaa$_3$ is Ala, Asp, Phe, Trp, or Tyr; and Xaa$_4$ is Asp, Gly, Leu, Phe, Ser, or Thr as described in US patent application 2003/0069395 or Dennis et al. (Dennis, M. S., Zhang, M., Meng, Y. G., Kadkhodayan, M., Kirchhofer, D., Combs, D. & Damico, L. A. (2002) *J Biol Chem* 277, 35035-35043).

In other embodiments, albumin itself (Osborn, B. L. et al., 2002, *J. Pharmacol. Exp. Ther.* 303, 540-548), or a biological active fragment of albumin can be used as conjugation partner of a lipocalin mutein or a fusion protein of the disclosure. The term "albumin" includes all mammal albumins such as human serum albumin or bovine serum albumin or rat albumine If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

When transferrin is used as a moiety to extend the serum half-life of the lipocalin muteins or the fusion proteins of the disclosure, the muteins or the fusion proteins can be genetically fused to the N or C terminus, or both, of non-glycosylated transferrin. Non-glycosylated transferrin has a half-life of 14-17 days, and a transferrin-conjugated mutein or fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the lipocalin muteins or fusion proteins of the disclosure, the SynFusion™ technology, commercially available from Syntonix Pharmaceuticals, Inc (MA, USA), may be used. The use of this Fc-fusion technology allows the creation of longer-acting biopharmaceuticals and may, for example, consist of two copies of a mutein linked to the Fc region of an antibody to improve pharmacokinetics, solubility, and production efficiency.

Yet another alternative to prolong the half-life of the lipocalin muteins or fusion proteins of the disclosure is to fuse to the N- or C-terminus of the muteins (including as comprised in fusion proteins of the disclosure) long, unstructured, flexible glycine-rich sequences (for example, poly-glycine with about 20 to 80 consecutive glycine residues). This approach disclosed in WO2007/038619, for example, has also been term "rPEG" (recombinant PEG).

If polyalkylene glycol is used as conjugation partner, the polyalkylene glycol can be substituted, unsubstituted, linear or branched. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins *J. Control. Release* 11, 139-148). The molecular weight of such a polymer, such as polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. No. 6,500,930 or 6,620,413, carbohydrate oligo- and polymers such as starch or hydroxyethyl starch (HES) can be conjugated to a mutein or a fusion protein of the disclosure for the purpose of serum half-life extension.

In addition, a lipocalin mutein or fusion protein disclosed herein may be conjugated to a moiety that may confer new characteristics to the lipocalin muteins or fusion proteins of the disclosure such as enzymatic activity or binding affinity for other molecules. Examples of suitable moieties include alkaline phosphatase, horseradish peroxidase, gluthation-S-transferase, the albumin-binding domain of protein G, protein A, antibody fragments, oligomerization domains or toxins.

In addition, it may be possible to fuse a lipocalin mutein or fusion protein disclosed herein with a separate enzyme active site such that both "components" of the resulting fusion protein together act on a given therapeutic target. For example, the binding domain of the lipocalin mutein (including as comprised in a fusion protein of the disclosure) may attach to the disease-causing target, allowing the enzyme domain to abolish the biological function of the target.

In some embodiments, a lipocalin mutein or a fusion protein of the disclosed may be conjugated to a moiety via a linker (e.g. a peptide bond) that covalently links a lipocalin mutein of the disclosure and another disclosed moiety to each other. This can be achieved, for example, by expression of the linked lipocalin muteins as a single polypeptide connected by a peptide linker. A suitable peptide linker can be comprised of a stretch of amino acids of arbitrary length containing any amino acids. A preferred linker design utilizes a repeated stretch of amino acids of glycines and serines following the formula (GxSy)n, where x is the number of glycine repeats and y the number of serine repeats in a building block that is repeated n times. The values of each of the variables x, y, and n can range from 0 to 100, preferably from 0 to 10. Non-limiting examples are hereby provided with SEQ ID NO: 18 and SEQ ID NOs: 36-38.

In some other embodiments, chemical methods of covalently linking may be applied to link a lipocalin mutein of the disclosure to another disclosed moiety. One example is the use of bifunctional linkers that allow reactive chemistry between the linker and an amino acid side chain, for example, between a maleimide and and a free cysteine in a lipocalin mutein, or an activated carboxylic acid ester and a primary amine in the lipocalin mutein. This includes reaction with non-natural amino acid side chains that may be included during protein expression, and which provide a functionality that can be selectively derivatised. In some still further embodiments, "click" chemistry, such as the cycloaddtion of an azide and an alkine, may be used to link one or more subunits of a fusion protein of the disclosure.

The present disclosure also relates to nucleic acid molecules (DNA and RNA) that include nucleotide sequences encoding the lipocalin muteins and the fusion proteins of the disclosure. Since the degeneracy of the genetic code permits substitutions of certain codons by other codons specifying the same amino acid, the disclosure is not limited to a specific nucleic acid molecule encoding a lipocalin mutein or a fusion protein as described herein but encompasses all nucleic acid molecules that include nucleotide sequences encoding a functional mutein or a functional fusion protein. In this regard, the present disclosure provides nucleotide sequences encoding some exemplary lipocalin muteins, some exemplary fusion proteins generic as shown in SEQ ID NOs: 23-35, 45-49 and 54.

In one embodiment of the disclosure, the method includes subjecting the nucleic acid molecule to mutagenesis at nucleotide triplets coding for at least one, sometimes even more, of the sequence positions corresponding to the sequence positions 28, 36, 40-41, 49, 52, 68, 70, 72-73, 75, 77, 79, 81, 87, 96, 100, 103, 106, 125, 127, 132 and 134 of the linear polypeptide sequence of human NGAL (SEQ ID NO: 8).

In another embodiment of the method according to the disclosure, a nucleic acid molecule encoding a human tear lipocalin is firstly subjected to mutagenesis at one or more of the amino acid sequence positions 26-34, 55-58, 60-61, 64, 104-108 of the linear polypeptide sequence of human tear lipocalin (SEQ ID NO: 1). Secondly, the nucleic acid molecule encoding a human tear lipocalin is also subjected to mutagenesis at one or more of the amino acid sequence positions 101, 111, 114 and 153 of the linear polypeptide sequence of the mature human tear lipocalin.

The disclosure also includes nucleic acid molecules encoding the lipocalin muteins and fusion proteins of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the muteins and the fusion proteins.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments a nucleic acid molecule of the disclosure includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a lipocalin mutein or a fusion protein as described herein, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a lipocalin mutein or a fusion protein as described herein, and in particular a cloning vector containing the coding sequence of such a mutein can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a lipocalin mutein or a fusion protein of the disclosure. Suitable host cells can be prokaryotic, such as *Escherichia coli* (*E. coli*) or *Bacillus subtilis*, or eukaryotic, such as *Saccharomyces cerevisiae, Pichia pastoris*, SF9 or High5 insect cells, immortalized mammalian cell lines (e.g., HeLa cells or CHO cells) or primary mammalian cells.

The disclosure also relates to a method for the production of a polypeptide as described herein, wherein the lipocalin mutein or the fusion protein is produced starting from the nucleic acid coding for the lipocalin mutein or the fusion protein by means of genetic engineering methods. The method can be carried out in vivo, the lipocalin mutein or the fusion protein can for example be produced in a bacterial or eucaryotic host organism and then isolated from this host organism or its culture. It is also possible to produce a protein in vitro, for example by use of an in vitro translation system.

When producing the lipocalin mutein, the fusion protein or the fragment in vivo, a nucleic acid encoding such mutein is introduced into a suitable bacterial or eukaryotic host organism by means of recombinant DNA technology (as already outlined above). For this purpose, the host cell is first transformed with a cloning vector that includes a nucleic acid molecule encoding a lipocalin mutein or a fusion protein as described herein using established standard methods. The host cell is then cultured under conditions, which allow expression of the heterologous DNA and thus the synthesis of the corresponding polypeptide. Subsequently, the polypeptide is recovered either from the cell or from the cultivation medium.

In some embodiments, a nucleic acid molecule, such as DNA, disclosed in this application may be "operably linked" to another nucleic acid molecule of the disclosure to allow expression of a fusion protein of the disclosure. In this regard, an operable linkage is a linkage in which the sequence elements of the first nucleic acid molecule and the sequence elements of the second nucleic acid molecule are connected in a way that enables expression of the fusion protein as a single polypeptide.

In addition, in some embodiments, the naturally occurring disulfide bond between Cys 76 and Cys 175 may be removed in NGAL muteins of the disclosure (including as comprised in fusion proteins of the disclosure). In some embodiments for Tlc muteins of the disclosure as well (including as comprised in fusion proteins of the disclosure), the naturally occurring disulfide bond between Cys 61 and Cys 153 may be removed. Accordingly, such muteins or fusion proteins can be produced in a cell compartment having a reducing redox milieu, for example, in the cytoplasma of Gram-negative bacteria.

In case a lipocalin mutein or a fusion protein of the disclosure includes intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds.

It is, however, also possible to produce a lipocalin mutein or a fusion protein of the disclosure in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8.).

However, a lipocalin mutein or a fusion protein as described herein may not necessarily be generated or produced only by use of genetic engineering. Rather, such a lipocalin mutein or a fusion protein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for IL-17A. Methods for the solid phase and/or solution phase synthesis of proteins are well known in the art (see e.g. Bruckdorfer, T. et al. (2004) *Curr. Pharm. Biotechnol.* 5, 29-43).

In another embodiment, the lipocalin muteins or the fusion proteins of the disclosure may be produced by in vitro transcription/translation employing well-established methods known to those skilled in the art.

The skilled worker will appreciate methods useful to prepare lipocalin muteins contemplated by the present disclosure but whose protein or nucleic acid sequences are not explicitly disclosed herein. As an overview, such modifications of the amino acid sequence include, e.g., directed mutagenesis of single amino acid positions in order to simplify sub-cloning of a mutated lipocalin gene or its parts by incorporating cleavage sites for certain restriction enzymes. In addition, these mutations can also be incorporated to further improve the affinity of a lipocalin mutein or a fusion protein for its target (e.g. IL-17A or IL-23p19, respectively). Furthermore, mutations can be introduced to modulate certain characteristics of the mutein or the fusion protein, such as, to improve folding stability, serum stability, protein resistance or water solubility or to reduce aggregation tendency, if necessary. For example, naturally occurring cysteine residues may be mutated to other amino acids to prevent disulphide bridge formation.

The lipocalin muteins and fusion proteins, disclosed herein, as well as their derivatives can be used in many fields similar to antibodies or fragments thereof. For example, the lipocalin muteins and/or fusion proteins, as well as their respective derivatives, can be used for labeling with an enzyme, an antibody, a radioactive substance or any other group having biochemical activity or defined binding characteristics. By doing so, their respective targets thereof can be detected or brought in contact with them. In addition, lipocalin muteins and/or fusion proteins of the disclosure can serve to detect chemical structures by means of established analytical methods (e.g., ELISA or Western Blot) or by microscopy or immunosensorics. In this regard, the detection signal can either be generated directly by use of a suitable mutein, or a suitable fusion protein; or indirectly by immunochemical detection of the bound mutein via an antibody.

Other protein scaffolds that can be engineered in accordance with the present invention to provide protein muteins that bind IL-17 and/or IL-23 with detectable affinity include: an EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill. et al. "Design and construction of a hybrid immunoglobulin domain with properties of both heavy and light chain variable regions" Protein Eng 10:949-57 (1997)), "Minibodies" (Martin et al. "The affinity-selection of a minibody polypeptide inhibitor of human interleukin-6" EMBO J 13:5303-9 (1994)), "Diabodies" (Holliger et al. "'Diabodies': small bivalent and bispecific antibody fragments" PNAS USA 90:6444-6448 (1993)), "Janusins" (Traunecker et al. "Bispecific single chain molecules (Janusins) target cytotoxic lymphocytes on HIV infected cells" EMBO J 10:3655-3659 (1991) and Traunecker et al. "Janusin: new molecular design for bispecific reagents" Int J Cancer Suppl 7:51-52 (1992), a nanobody, an adnectin, a tetranectin, a microbody, an affilin, an affibody an ankyrin, a crystallin, a knottin, ubiquitin, a zinc-finger protein, an autofluorescent protein, an ankyrin or ankyrin repeat protein or a leucine-rich repeat protein, an avimer (Silverman, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P 2005, Nat Biotech, December; 23(12):1556-61, E-Publication in Nat Biotech. 2005 Nov. 20 edition); as well as multivalent avimer proteins evolved by exon shuffling of a family of human receptor domains as also described in Silverman J, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P, Nat Biotech, December; 23(12):1556-61, E-Publication in Nat. Biotechnology. 2005 Nov. 20 edition).

Additional objects, advantages, and features of this disclosure will become apparent to those skilled in the art upon examination of the following Examples and the attached Figures thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

V. EXAMPLES

Example 1: Affinity of Lipocalin Mutein to IL-17A Measured by SPR

To measure the binding affinity of the lipocalin mutein of SEQ ID NO: 1 to IL-17A, a surface plasmon resonance (SPR) based assay was employed utilizing a Biacore T200 instrument (GE Healthcare). In the SPR affinity assay (FIG. 1), IL-17A was immobilized on a sensor chip using standard amine chemistry: The surface of the chip was activated using 1-Ethyl-3-(3-dimethylaminopropyl)carbodiimid (EDC) and N-hydroxysuccinimid (NHS). Subsequently, 5 µg/mL of IL-17A solution in 10 mM Acetate pH 5 was applied at a flow rate of 10 µL/min until an immobilization level of 279 resonance units (RU) was achieved. Residual activated groups were quenched with ethanolamine. The reference channels underwent blank immobilization by treatment with EDC/NHS following ethanolamine.

To determine the affinity, four dilutions of SEQ ID NO: 1 were prepared in HBS-EP+ buffer and applied to the prepared chip surface. The binding assay was carried out with a contact time of 300 s, dissociation time of 1200 s and applying a flow rate of 30 µL/min. All measurements were performed at 25° C. Regeneration of the immobilized IL-17A surface was achieved with consecutive injections of 10 mM aqueous $H_3PO_4$ (30 s) and 10 mM glycine-HCl pH 1.5 (15 s) followed by an extra wash with running buffer and a stabilization period of 30 s. Prior to the protein measurements three startup cycles were performed for conditioning purposes. Data were evaluated with Biacore T200 Evaluation software (V 1.0). Double referencing was used. The 1:1 binding model was used to fit the raw data.

The resulting fit curves are shown in FIG. 1. The data shows that SEQ ID NO: 1 bound with high affinity to IL-17A, with an association rate constant of $k_a=7.0 \times 10^4$ $M^{-1}sec^{-1}$ and a dissociation rate constant of $k_d=5.3 \times 10^{-5}$ $sec^{-1}$, resulting in a dissocation constant of $K_D=0.8$ nM.

Example 2: Affinity of Lipocalin Mutein to IL-17 A/F Measured by SPR in an Alternative Format To measure the binding affinity of the lipocalin mutein of SEQ ID NO: 1 to IL-17AF in a Surface Plasmon Resonance (SPR) based assay in an alternative assay format—capturing SEQ ID NO: 1 as a ligand and applying human IL-17 A/F as an analyte—a Biacore T200 instrument (GE Healthcare) was used. In this format, human IL-17 A/F was employed (as opposed to the homodimeric IL-17A, which was used in Example 1) to avoid potential avidity effects in the assay. SEQ ID NO: 1 was biotinylated for 2 h at room temperature applying an appropriate excess of EZ-Link NHS-PEG4-Biotin (Thermo, Cat #21329) followed by separation of non-reacted Biotin using a Zeba Spin Desalting Plate (Thermo, Cat #21329) according to the manufacturers instructions.

In the SPR affinity assay, biotinylated SEQ ID NO: 1 was captured on a sensor chip CAP using the Biotin CAPture Kit (GE Healthcare): The sensor Chip CAP was pre-immobilized with an ssDNA oligonucleotide. Undiluted Biotin CAPture Reagent (streptavidin conjugated with the complementary ss-DNA oligonucleotide) was applied at a flow rate of 2 µL/min for 300 s. Subsequently, 0.4 to 10 µg/mL of biotinylated SEQ ID NO: 1 was applied for 300 s at a flow rate of 5 µL/min. The reference channel was loaded with Biotin CAPture Reagent only.

To determine the binding affinity, five dilutions of human IL-17 A/F (0.2-20 nM) were prepared in HBS-EP+ buffer and applied to the prepared chip surface. Applying a flow rate of 30 µL/min, a single cycle kinetics approach was used with a sample contact time of 300 s and a dissociation time of 2400 s. After ligand immobilization, all 5 concentrations were applied consecutively in ascending order before the dissociation was monitored. All measurements were performed at 25° C. Regeneration of the Sensor Chip CAP surface was achieved with an injection of 6 M Gua-HCl with 0.25 M NaOH followed by an extra wash with running buffer and a stabilization period of 120 s. Data were evaluated with Biacore T200 Evaluation software (V 1.0). Double referencing was used. A single cycle kinetic 1:1 binding model was used to fit the raw data.

The resulting fit curves are shown in FIG. 2. The data shows that SEQ ID NO: 1 bound with high affinity to human IL-17 A/F, with an association rate constant of $k_a=1.2 \times 10^6$ $M^{-1}sec^{-1}$ and a dissociation rate constant of $k_d=1.2 \times 10^{-4}$ $sec^{-1}$, resulting in a calculated equilibrium dissocation constant of $K_D=100$ pM. A comparison to Example 1 shows that the result of the SPR assay is somewhat dependent on the assay format. However, in both formats, the affinity of SEQ ID NO: 1 to human IL-17A and human IL-17 A/F, respectively, is high and in the subnanomolar range. The assay is important for allowing a comparison between SEQ ID NO: 1 and fusions containing this mutein (see below Example 11).

Example 3: Competitive Mode of Action of Lipocalin Mutein Binding to IL-17A

Whether SEQ ID NO: 1 binds to IL-17A in a competitive mode was tested in vitro using a competition ELISA format (FIG. 3). In this experiment, a constant concentration of biotinylated human IL-17A was incubated with variable concentrations of SEQ ID NO: 1 for 1 h. After this pre-incubation in solution, an aliquot of the lipocalin mutein/IL-17A mixture was transferred to an ELISA plate coated with human IL-17RA to measure the concentration of hIL-17A that was not blocked to bind to hIL-17RA (FIG. 3).

All incubation steps were performed with shaking at 300 rpm, and the plate was washed after each incubation step with 80 µl PBS-T buffer (PBS, 0.05% Tween 20) for five times using a Biotek EL405 select CW washer. In the first step, a 384 well MSD plate was directly coated with 20 µl of soluble human IL-17RA at a concentration of 1 µg/ml in PBS over night at 4° C. After washing, the receptor coated wells were blocked with 60 µl PBS-T/BSA (2% BSA in PBS containing 0.1% Tween 20) for 1 h at room temperature.

A fixed concentration of 0.01 nM human IL-17A was incubated in solution with varying concentrations of SEQ ID NO: 1, or with SEQ ID NO: 41 as a negative control, using a suitable starting concentration of SEQ ID NO: 1 and SEQ ID NO: 41 which was serially diluted at a 1:4 ratio down to the picomolar range in PBS-T/BSA buffer. After 1h incubation at room temperature, 20 µl of the reaction mixture was transferred to the hIL-17RA-coated MSD plate to capture unbound (free) or non-competitively bound hIL-17A for 20 min at RT. To allow for transformation of ELISA readout results into absolute free hIL-17A concentrations (cf. below), a standard curve containing varying concentrations of hIL-17A was prepared in PBS-T/BSA and incubated for 20 min on the same MSD plate as well.

To allow for detection and quantitation of bound biotinylated hIL-17A, the residual supernatants were discarded and 20 µl Strepavidin Sulfo-tag was added at a concentration of 1 µg/mL in PBS-T/BSA and incubated for 1 h at RT. After washing, 60 µl MSD Read Buffer T (2×) was added to each well and the plate was read within 15 min.

The resulting Electrochemoluminescence (ECL) signal was measured using the SECTOR Imager 2400 (Meso Scale Discovery). The evaluation was performed as follows: free IL-17A concentration $c(IL-17A)_{free}$ was calculated (from the standard curve determined in parallel) and plotted versus SEQ ID NO: 1 concentration, c(SEQ ID NO: 1). To obtain the SEQ ID NO: 1 concentration at which formation of the IL-17A/IL-17 RA-complex was blocked by 50% (IC50), the curves were fitted by nonlinear regression with a single-sites binding model according to $c(IL-17A)_{free}=c(IL-17A)_{tot}/(1+c(SEQ\ ID\ NO:\ 1)/IC50))$, with the total tracer concentration $c(IL-17A)_{tot}$ and the IC50 value as free parameters. Curve fitting was performed using GraphPad Prism 4 software.

FIG. 3 shows that the negative control SEQ ID NO: 41 does not bind to hIL-17A; in contrast, SEQ ID NO: 1 demonstrates a strong competitive binding to hIL-17A, with a fitted IC50 value of 75 pM.

Example 4: Specificity and Species Crossreactivity of Lipocalin Mutein to IL-17A Specificity and species crossreactivity (FIG. 4) of the lipocalin mutein of SEQ ID NO: 1 were assayed by a "solution competition ELISA", the principle of which was as follows: A constant concentration of SEQ ID NO: 1 was incubated with variable concentrations of ligands the ligands human IL-17A, cynomolgus monkey IL-17A (cIL-17A), and marmoset IL-17A or 1 h. After this pre-incubation in solution, an aliquot of the mutein/ligand mixture was transferred to an ELISA plate with biotinylated hIL-17A immobilized via neutravidin to measure the remaining concentration of free SEQ ID NO: 1. The concentration of free (non ligand-bound) SEQ ID NO: 1 was determined via a quantitative ELISA setup (FIG. 4). Note that this assay relied on that all ligands were targeting the same binding site on the SEQ ID NO: 1, i.e. that the ligands bound to the SEQ ID NO: 1 in competition with each other.

In the following detailed experimental protocol, incubation and washing steps were performed as described above in the competition ELISA protocol. A 384-well plate suitable for fluorescence measurements (Greiner FLUOTRAC™ 600, black flat bottom, high-binding) was coated with 20 µl of Neutravidin at a concentration of 5 µg/ml in PBS over night at 4° C. After washing, the Neutravidin-coated wells were blocked with 100 µl blocking buffer (PBS-T/BSA) for 1h at room temperature. After washing again, 20 µl biotinylated hIL-17A at a concentration of 1 µg/mL in PBS was added for 1h at room temperature, and excess reagent was removed.

A fixed concentration of 0.25 nM SEQ ID NO: 1 was incubated in solution with varying concentrations of ligands (hIL-17A, cIL-17A and marmoset IL-17A), using a suitable starting concentration which was serially diluted at a 1:3 ratio down to the picomolar range in PBS-T/BSA. After 1h incubation at room temperature, 20 µl of the reaction mixture was transferred to the 384-well plate upon which biotinylated hIL-17A was immobilized to capture unbound (free) SEQ ID NO: 1 for 20 min at RT. To allow for transformation of ELISA readout results into absolute free SEQ ID NO: 1 concentrations (cf. below), a standard curve containing varying concentrations of SEQ ID NO: 1 was prepared in PBS-T/BSA and incubated for 20 min on the same ELISA plate as well.

The residual supernatants were discarded and 20 µl HRP-labeled anti-lipocalin antibody was added at a predetermined optimal concentration in PBS-T/BSA and incubated for 1 h at RT. The anti-lipocalin antibody had been obtained by immunization of rabbits with a mixture of lipocalin muteins, and was subsequently coupled to HRP using a kit (EZ-link Plus Activated Peroxidase, Thermo Scientific) according to the manufacturer's instructions, to obtain the antibody-HRP conjugate. After washing, 20 µl fluorogenic HRP substrate (Quantablue, Pierce) was added to each well, and the reaction was allowed to proceed for 60 minutes. The fluorescence intensity of every well on the plate was read using a Genios Plus Microplate reader (Tecan). To evaluate the data, free SEQ ID NO: 1 concentration, $c(SEQ\ ID\ NO:\ 1)_{free}$, was calculated based on the standard curve results, and plotted versus ligand concentration, c(Ligand). To obtain the ligand concentration at which formation of the IL-17A/SEQ ID NO: 1 complex was blocked by 50% (IC50), the curves were fitted by nonlinear regression with a single-sites binding model according to $c(SEQ\ ID\ NO:\ 1)_{free}=c(SEQ\ ID\ NO:\ 1)_{tot}/(1+c(Ligand)/IC50))$, with the total tracer concentration $c(SEQ\ ID\ NO:\ 1)_{tot}$ and the IC50 value as free parameters. Curve fitting was performed using GraphPad Prism 4 software.

In summary, curve fitting yielded the following results: $IC50_{hIL-17A}=0.1$ nM, $IC50_{cIL-17A}=0.1$ nM and $IC50_{marmoset\ IL-17A}=0.2$ nM. As depicted in FIG. 4, the data demonstrates that SEQ ID NO: 1 displays high affinity towards IL-17A from human, cynomolgus monkey and marmoset monkey, and therefore, shows that SEQ ID NO: 1 is fully crossreactive with cynomolgus and marmoset monkey IL-17A.

Example 5: Lipocalin-Mutein-Mediated Blockade of IL-17A Induced G-CSF Secretion in a Cell-Based Assay We employed a cell-based assay to demonstrate the ability of SEQ ID NO: 1 to block the biological activity of IL-17A. The assay was based on IL-17A-induced secretion of G-CSF in U87-MG cells (ATCC catalog #HTB-14). This highly sensitive functional assay was employed to compare the potency of SEQ ID NO: 1 to two benchmark antibodies that are developed clinically. In this assay, recombinant hIL-17A was preincubated with SEQ ID NO: 1, benchmark antibody molecules or controls and added to the cells. Besides SEQ ID NO: 1, the following benchmarks and controls were included in the assay: benchmark antibody 1 (heavy chain SEQ ID NO: 53; light chain SEQ ID NO: 54), benchmark antibody 2 (heavy chain SEQ ID NO 55; light chain SEQ ID NO: 56) and SEQ ID NO: 2 and a human IgG isotype antibody (Dianova, CAT #009-000-002) as negative controls. The concentration of G-CSF in the supernatant was then measured by ELISA.

U87-MG cells were cultured in cell culture flasks under standard conditions (Dulbecco's Modified Eagle Medium DMEM (PAN Biotech GmbH) containing 10% fetal calf serum FCS (PAA Laboratories), 37° C., 5% $CO_2$ atmosphere).

On day 1 of the experiment, the adherent cells were dissociated from their substrate with Accutase (PAA Laboratories) according to the manufacturer's instructions. Subsequently, cells were centrifuged down for 5 minutes at 1000 rpm, resuspended in medium and filtered through a 100 µm cell strainer (Falcon) to remove cell aggregates. Cells were then seeded in 96-well flat bottom tissue culture plates (Greiner) at a density of 5000 cells per well using an end volume of 100 µl. They were incubated overnight under standard conditions.

SEQ ID NO: 1, SEQ ID NO: 2, a human IgG isotype antibody (Dianova, CAT #009-000-002), benchmark antibody 1 and benchmark antibody 2 (as described above) were the molecules under study ("MUS"). On day 2, the medium of the cells grown in the 96-well plate was replaced by 80 µl fresh medium and a fixed concentration of 0.1 nM recombinant hIL-17A and a dilution series of MUS-solutions were subsequently added to the cells. This was done in triplicate for each MUS or control. The cells were incubated for a further 20-24 hours under standard conditions. Before collection of the supernatants for measurement of G-CSF levels, wells were visually inspected with a microscope. Wells that exhibited considerable cell death or the presence of cellular aggregates were excluded from evaluation. G-CSF levels were determined using the G-CSF Ultra-Sensitive Kit from MSD. To evaluate the data, the G-CSF concentration in arbitrary units was plotted versus the MUS concentration, c(MUS). To obtain the MUS concentration at which induction of G-CSF production by U-87 MG cells was reduced to 50% (IC50), the curves were fitted by nonlinear regression with a single-sites binding model according to $c(G-CSF) = c(G-CSF)_{Min} + [c(G-CSF)_{Max} - c(G-CSF)_{Min}]/[1+c(MUS)/IC50]$, with free parameters being IC50, the induced G-CSF concentration $c(G-CSF)_{Max}$, and the uninduced G-CSF concentration $c(G-CSF)_{Min}$. Here, it was assumed that $c(G-CSF)_{Max}$ and $c(G-CSF)_{Min}$ were independent of the antagonist or control molecule under study, and they were therefore fitted to common values for all molecules.

FIG. 5 shows a representative example of the experiment, which was performed in duplicate. The resulting average EC50 value for SEQ ID NO: 1 was 0.13 nM (0.17 nM in the first experiment, 0.10 nM in the repeat experiment), which was significantly more potent that benchmark 1, which exhibited an EC50=2.33 (2.65/2.01) nM, and in a similar range compared to benchmark 2, with an EC50=0.12 (0.14/0.10) nM. Negative controls, consisting of SEQ ID NO: 2 and a human IgG isotype antibody (Dianova, CAT #009-000-002, not shown in FIG. 5), had no effect on IL-17A-induced G-CSF production of the cells.

Example 6: Affinity of Lipocalin Mutein to IL-23 Measured by SPR

To measure the binding affinity of the lipocalin muteins of SEQ ID NO: 2 to human IL-23, a surface plasmon resonance (SPR) based assay was employed utilizing a Biacore T200 instrument (GE Healthcare). In the SPR affinity assay (FIG. 6), hIL-23 was immobilized on a sensor chip using standard amine chemistry: The surface of the chip was activated using EDC and NHS. Subsequently, 5 µg/mL of hIL-23 solution in 10 mM acetate pH 4.5 was applied at a flow rate of 10 µL/min until a sufficient immobilization level was achieved. Residual activated groups were quenched with ethanolamine. The reference channels were treated with EDC/NHS following ethanolamine (blank immobilization).

To determine the binding affinity of SEQ ID NO: 2, five dilutions of SEQ ID NO: 2 were prepared in HBS-EP+ buffer and applied to the prepared chip surface. The binding assay was carried out with a contact time of 300 s, dissociation time of 1200 s and applying a flow rate of 30 µL/min. All measurements were performed at 25° C. Regeneration of the immobilized hIL-23 surface was achieved by injection of 10 mM aqueous $H_3PO_4$ (30 s) followed by an extra wash with running buffer and a stabilization period of 30 s. Prior to the protein measurements three startup cycles were performed for conditioning purposes. Data were evaluated with Biacore T200 Evaluation software (V 1.0). Double referencing was used. The 1:1 binding model was used to fit the raw data.

FIG. 6 shows a representative example of the experiment, which were performed in triplicate. The resulting fit curves demonstrate that SEQ ID NO: 2 bound with high affinity to hIL-23, with an association rate constant of $k_a = 5.0 \times 10^4$ $M^{-1} sec^{-1}$ and a dissociation rate constant of $k_d = 1.9 \times 10^{-5}$ $sec^{-1}$. The average dissocation constant determined in three replicate experiments amounted to $K_D = 0.35 \pm 0.20$ nM, demonstrating the high-affinity interaction between SEQ ID NO: 2 and human IL-23.

Example 7: Affinity of Lipocalin Mutein to IL-23 Measured by SPR in an Alternative Format To measure the binding affinity of SEQ ID NO: 2 to human IL-23 using surface plasmon resonance (SPR) in an alternative assay format—capturing SEQ ID NO: 2 as a ligand and applying hIL-23 as an analyte—a Biacore T200 instrument (GE Healthcare) was used. SEQ ID NO: 2 and controls were biotinylated as described in Example 2. In the SPR affinity assay, biotinylated SEQ ID NO: 2 was captured on a sensor chip CAP using the Biotin CAPture Kit (GE Healthcare). To this end, undiluted Biotin CAPture Reagent was applied at a flow rate of 2 μL/min for 300 s. Subsequently, 0.4 to 10 μg/mL of biotinylated SEQ ID NO: 2 or controls was applied for 300 s at a flow rate of 5 μL/min. The reference channel was loaded with Biotin CAPture Reagent only.

To determine the binding affinity, five dilutions of hIL-23 (7-600 nM) were prepared in HBS-EP+ buffer supplemented with 350 mM NaCl and applied to the prepared chip surface. The addition of 350 mM NaCl was required to minimize non-specific interaction of hIL-23 with the chip surface. Applying a flow rate of 30 μL/min, a single cycle kinetics approach was used with a sample contact time of 300 s and a dissociation time of 4000 s or 7200 s. After ligand immobilization, all 5 concentrations were applied consecutively in ascending order before the dissociation was monitored. All measurements were performed at 25° C. Regeneration of the Sensor Chip CAP surface and data evaluation was accomplished as described in Example 2.

The resulting fit curves are shown in FIG. 7. The data shows that SEQ ID NO: 2 bound with rather high affinity to hIL-23, with an association rate constant of $k_a=1.23 \times 10^{-4}$ $M^{-1}sec^{-1}$ and a dissociation rate constant of $k_d=3.55 \times 10^{-5}$ $sec^{-1}$, resulting in a calculated equilibrium dissocation constant of $K_D=2.9$ nM. A comparison to Example 6 shows a strong drop in affinity when using this SPR assay format, which is attributable to the high and nonphysiological concentration of NaCl (350 mM) that had to be included in the buffer to minimize nonspecific interactions of hIL-23 with the chip surface, and therefore facilitate carrying out the assay in this format. The assay is important for allowing a comparison between SEQ ID NO: 2 and fusions containing this mutein (see below Example 11).

Example 8: Competitive Mode of Action of Lipocalin Mutein Binding to IL-23

Whether the lipocalin mutein SEQ ID NO: 2 binds to hIL-23 in a competitive mode was tested in vitro using a competition ELISA format (FIG. 8), in analogy to Example 3, but using hIL-23 as the target.

All incubation steps were performed with shaking 300 rpm, and the plate was washed after each incubation step with 80 μl PBS/0.05% Tween 20 for five times using a Biotek EL405 select CW washer. A 384 well MSD plate was directly coated with 20 μl of soluble human IL-23 receptor at a concentration of 1 μg/ml in PBS over night at 4° C. After washing, the receptor-coated wells were blocked with 60 μl PBS-T/BSA for 1 h at room temperature.

A fixed concentration of 0.01 nM biotinylated human IL-23 was incubated in solution with varying concentrations of SEQ ID NO: 2, or with SEQ ID NO: 43 as a negative control, using suitable starting concentrations which were serially diluted at a 1:4 ratio down to the picomolar range in PBS-T/BSA. After 1h incubation at room temperature, 20 μl of the reaction mixture was transferred to the IL-23 receptor-coated MSD plate to capture unbound (free) or non-competitively bound hIL-23 for 20 min at RT. To allow for transformation of ELISA readout results into absolute free hIL-23 concentrations (cf. below), a standard curve containing varying concentrations of hIL-23 starting with 100 nM (1:4 serially diluted in 11 steps) was prepared in PBS-T/BSA and incubated for 20 min on the same MSD plate as well. To allow for detection and quantitation of bound biotinylated hIL-23, the residual supernatants were discarded and 20 μl Strepavidin Sulfo-tag was added at a concentration of 1 μg/mL in PBS-T/BSA and incubated for 1 h at RT. After washing, 60 μl MSD Read Buffer T (2×) was added to each well and the plate was read within 15 min.

The resulting ECL signal was measured using the SECTOR Imager 2400 (Meso Scale Discovery). The evaluation was performed in analogy to Example 3. As shown in FIG. 8, the negative control SEQ ID NO: 43 did not bind to hIL-23, in contrast, SEQ ID NO: 2 demonstrated a competitive binding to hIL23, with a fitted IC50 value of 0.54 nM.

Example 9: Specificity and Species Crossreactivity of Lipocalin Mutein to IL-23

The specificity and species crossreactivity of the lipocalin mutein of SEQ ID NO: 2 (FIG. 9) was assayed by a "solution competition ELISA", in analogy to Example 4, but studying different ligands, namely, IL-23 from human, cynomolgus monkey (cIL-23), marmoset monkey and mouse.

In the following detailed experimental protocol, incubation and washing steps were performed as described above in the competition ELISA protocol. A 384-well plate suitable for fluorescence measurements (Greiner FLUOTRAC™ 600, black flat bottom, high-binding) was coated with 20 μl of Neutravidin at a concentration of 5 μg/ml in PBS over night at 4° C. After washing, the Neutravidin-coated wells were blocked with 100 μl PBS-T/BSA for 1h at room temperature. After washing again, 20 μl biotinylated hIL-23-Bio at a concentration of 0.25 μg/mL in PBS was added for 1h at room temperature, and excess reagent was removed.

A fixed concentration of 0.5 nM SEQ ID NO: 2 was incubated in solution with varying concentrations of the ligands (hIL-23, cIL-23, marmoset IL-23 and mouse IL-23), using a suitable starting concentration which was serially diluted at a 1:3 ratio down to the picomolar range in PBS-T/BSA. After 20 minutes incubation at room temperature, 20 μl of the reaction mixture was transferred to the hIL-23 coated 384-well plate to capture unbound (free) SEQ ID NO: 2 for 20 min at RT. To allow for transformation of ELISA readout results into absolute free SEQ ID NO: 2 concentrations (cf. below), a standard curve containing varying concentrations of SEQ ID NO: 2 was prepared in PBS-T/BSA and incubated for 20 min on the same MSD plate as well.

To quantitate plate-captured SEQ ID NO: 2, the residual supernatants were discarded and 20 μl HRP-labeled anti-lipocalin antibody was added at a predetermined optimal concentration in PBS-T/BSA and incubated for 1 h at RT. The anti-ipocalin antibody had been obtained by immunization of rabbits with a mixture of lipocalin muteins, and was subsequently coupled to HRP using a kit (EZ-link Plus Activated Peroxidase, Thermo Scientific) according to the manufacturer's instructions, to obtain the antibody-HRP conjugate. Further handling of the plates, data acquisition and evaluation were performed as described in Example 4.

As shown in FIG. 9, the result demonstrates that SEQ ID NO: 2 is fully crossreactive with human and mouse IL-23, and displays a somewhat reduced affinity towards IL-23 of cynomolgus and marmoset monkey, with $IC50_{hIL-23}=0.9$ nM, $IC50_{cIL-23}=4.8$ nM, $IC50_{marmIL-23}=12$ nM and $IC50_{mIL-23}=0.5$ nM.

Example 10: Lipocalin-Mutein-Mediated Blockade of IL-23 in Cell-Based Proliferation Assays The ability of the lipocalin mutein of SEQ ID NO: 2 to neutralize the biological activity of hIL-23 was assessed by the application of short-term proliferation bioassays employing cells that recombinantly express the human IL-23 receptor. The Ba/F3 transfectant cell line expresses both subunits of the receptor, hIL-23R and hIL-12Rβ1, and is responsive to both human IL-23 and cynomolgus monkey IL-23. The Ba/F3 cells proliferate responding to hIL-23 in a dose-dependent manner, and proliferation can be inhibited by an hIL-23-neutralizing agent. In the assay, SEQ ID NO: 2 was preincubated at various concentrations with a constant amount of hIL-23, and the mixtures were subsequently added to Ba/F3 cells in culture. After three days in culture, the extent of proliferation was assessed by quantifying the number of viable cells. This was performed using the CellTiter-Glo Luminescent Cell Viability Assay (Promega CAT #G7571) to measure ATP levels, which correlate with the number of metabolically active cells. The ability of SEQ ID NO: 2 to neutralize hIL-23 was assessed by its IC50 value, i.e. the concentration of the lipocalin mutein that leads to half-maximal inhibition of hIL-23 induced proliferation.

The detailed procedure of setting up the assay is hereby described in the following. Ba/F3 transfectants were maintained in RPMI-1640 medium, 10% fetal calf serum, 0.05 mM 2-mercaptoethanol, 500 µg/mL geneticin (G418), 1 ng/mL mIL-3, 2 µg/mL puromycin, and 200 µg/mL zeocin. Ba/F3 proliferation assays were carried out in RPMI-1640 medium, 10% fetal calf serum, and 0.05 mM 2-mercaptoethanol. Assays were performed in 384-well white clear flat-bottom plates (Greiner) in 25 µL per well.

On day 1, cells from a Ba/F3 suspension cell culture were counted, pelleted, washed twice in assay medium, and plated at a density of 2500 cells per well. 50 pM of hIL-23 (CAT #HZ-1254, HumanZyme)—corresponding to the predetermined EC50 required to induce Ba/F3 cell proliferation—and dilution series of SEQ ID NO: 2, a negative control (human IgG isotype antibody, CAT #. 009-000-003, Dianova) and of benchmark antibodies (benchmark 3: SEQ ID NO: 57 and SEQ ID NO: 58, benchmark 4: SEQ ID NO: 59 and SEQ ID NO: 60) were added to the wells. All titration series were performed with a serial 1:3 dilution in assay medium and a suitable starting concentration. Subsequently, the cells were allowed to proliferate for 72 hours at 37° C. To ensure that the potency of hIL-23 was not subject to inter- and intra-day variability, the dose-dependent proliferation response of the Ba/F3 cells to hIL-23 was checked by adding a dilution series of hIL-23 alone to Ba/F3 cells, using 1:3 dilution steps in assay medium starting with 50 nM. To quantify cell proliferation after 72 hours, 25 µL CellTiter-Glo reagents were added to the cells in each of the wells and incubated for 2 minutes on an orbital shaker to induce cell lysis, and luminescence was measured using the PheraStar FS reader.

EC50 values were determined using GraphPad Prism software (GraphPad Software Inc., San Diego, Calif., USA) by plotting Luminescence signal agains samples' concentration and non-linear regression of the data with a sigmoidal dose-response model.

The result of the experiment is shown in FIG. 10. The proliferation assay disclosed above is representative of two independent experiments. SEQ ID NO: 2 displayed an average EC50 of 1.2 nM (1.7 nM in a first experiment, 0.7 nM in the repeat experiment), benchmark 3 exhibited an EC50 of 3.0 nM (3.1/2.9), and benchmark 4 exhibited an EC50 of 1.2 nM (0.8/1.5). The negative control had no effect on proliferation. The data therefore demonstrates that SEQ ID NO: 2 and the benchmark molecules exhibit a comparable potency in this functional assay.

Example 11: Design and Characterization of Fusion Proteins

Various fusion proteins containing either one or both of the IL-17A and IL-23-binding lipocalin muteins were generated, expressed and characterized as follows and as depicted in FIG. 11.

SEQ ID NO: 8 is a fusion protein of SEQ ID NO: 1 and a deimmunised albumin binding peptide (dABD, SEQ ID NO: 15), which is derived from the albumin binding domain of streptococcal protein G.

SEQ ID NO: 7 is a fusion protein of SEQ ID NO: 2 and SEQ ID NO: 15.

SEQ ID NO: 10 is a homodimeric fusion protein of two SEQ ID NO: 1 sequences in a row, linked via linker SEQ ID NO: 18, and fused to SEQ ID NO: 15.

SEQ ID NO: 3 is a heterodimeric fusion protein of SEQ ID NO: 1 and SEQ ID NO: 2, linked via linker SEQ ID NO: 18; while SEQ ID NO: 4 is a heterodimeric fusion protein with a reversed lipocalin mutein order, SEQ ID NO: 2 and SEQ ID NO: 1, and linked with the slightly different linker SEQ ID NO: 19.

SEQ ID NO: 5 is a fusion protein corresponding to SEQ ID NO: 3, but with an additional C-terminal fusion to the albumin binding domain of streptococcal protein G (SEQ ID NO: 14)

SEQ ID NO: 9 is a fusion protein corresponding to SEQ ID No: 3, but with an additional C-terminal fusion to dABD (SEQ ID NO: 15).

SEQ ID 6 is a trimeric fusion protein consisting of two SEQ ID NO: 1 sequences in a row, fused C-terminally to SEQ ID NO: 2 and dABD (SEQ ID NO: 15). The linkers between the lipocalins consisted of SEQ ID NO: 18.

We also generated fusion proteins of one or more SEQ ID NO: 1 moeities to the Fc part of IgG1, which corresponds to SEQ ID NO: 16:

SEQ ID NO: 11 is a fusion protein corresponding to a C-terminal fusion of SEQ ID NO: 1 to SEQ ID NO: 16, linked via the peptide linker SEQ ID NO: 19.

SEQ ID NO: 12 is a fusion protein corresponding to a N- and C-terminal double fusion of SEQ ID NO: 1, such that the Fc molecule of SEQ ID NO: 16 is endowed with SEQ ID NO: 1 at both the N- and the C-termini.

SEQ ID NO: 13 is a fusion protein corresponding to a C-terminal fusion of the homodimeric fusion protein of SEQ ID NO: 10 to the Fc molecule of SEQ ID NO: 16.

All fusion proteins were—where applicable—fully characterized by assays exactly as described above for SEQ ID NO: 1 and SEQ ID NO: 2: competition ELISA assays for hIL-17A (Example 3) and hIL-23 (Example 8), SPR assays where the fusion protein was immobilized on an SPR chip for hIL-17AF (Example 2) and hIL-23 (Example 6), and functional cell-based assays as described for hIL-17A (Example 5) and hIL-23 (Example 10).

The experimental results are summarized in Table 1. The table provides an overview of the activity of individual ipocalin muteins SEQ ID NO: 1 and SEQ ID NO: 2, compared to their fusion proteins SEQ ID NOs: 3-13 in competition ELISA, surface plasmon resonance (SPR) and functional cell-based assays. Values were determined for the interaction with IL-17 and/or IL-23, depending on whether the respective construct contains the IL-17A-binding lipocalin mutein SEQ ID NO: 1, the IL-23-binding lipocalin mutein SEQ ID NO: 2, or both. To determine the activity towards IL-17 and IL-23, respectively, competition ELISA experiments were carried out as described in Example 3 and/or Example 8, SPR experiment in reverse format—i.e. with the protein constructs immobilized on the sensor chip—were carried out as described in Example 2 and/or Example 6, and cell assays were based on either IL-17A-induced G-CSF secretion (Example 5) and/or IL-23 induced Ba/F3 cell proliferation (Example 10). Note that the reverse format SPR experiment performed to determine IL-23 affinity was carried out in the presence of unphysiologically high concentrations of NaCl, and that the values therefore do not reflect the affinity to IL-23 under physiological conditions, but serve to determine whether the relative affinity to IL-23 is different in the fusion proteins SEQ ID NO's: 3-13 compared to the individual muteins SEQ ID NO: 1 and SEQ ID NO: 2. Table 1 demonstrates that the IL-17A-binding activity of all fusions containing SEQ ID NO: 1 is at least as good as that of SEQ ID NO: 1 itself in all assay formats. SEQ ID NO: 1 can therefore flexibly be employed in any fusion protein without activity loss. The IL-23-binding activity of all fusions containing SEQ ID NO: 2 is very close to that of SEQ ID NO: 2 itself in all assay formats. SEQ ID NO: 2 can therefore flexibly be employed in any fusion protein without significant activity loss.

Example 12: An SPR Experiment Designed to Show Simultaneous Binding of all Targets by Fusion Protein To demonstrate simultaneous binding of the fusion protein of SEQ ID NO: 9 to hIL-17A, hIL-23 and human serum albumin (HSA), a surface plasmon resonance (SPR) based assay was employed using a Biacore T200 instrument (GE Healthcare). SEQ ID NO: 9 was biotinylated as described in Example 2. In the SPR affinity assay, biotinylated SEQ ID NO: 9 was captured on a sensor chip CAP using the Biotin CAPture Kit (GE Healthcare). To this end, undiluted Biotin CAPture Reagent was applied at a flow rate of 2 µL/min for 300 s. Subsequently, 0.4 to 10 µg/mL of biotinylated SEQ ID NO: 9 was applied for 300 s at a flow rate of 5 µL/min. The reference channel was loaded with Biotin CAPture Reagent only.

To demonstrate simultaneous binding, dilutions of hIL-17 A/F, hIL-23 and HSA (200 nM, 1000 nM and 2000 nM) were prepared in HBS-EP+ buffer supplemented with 350 mM NaCl and consecutively applied to the prepared chip surface. Applying a flow rate of 30 µL/min, hIL-17 A/F, hIL-23 and HSA were consecutively injected with a sample contact time of 300 s. The application of target to immobilized SEQ ID NO: 9 was also performed employing the single ligands hIL-17 A/F, hIL-23 and HSA, to obtain the maximum binding levels obtainable by binding a single target for comparison.

FIG. 12 compares the measured binding curve with a theoretical binding curve reflecting complete binding of all ligands. The latter was obtained by assembling the experimental response of SEQ ID NO: 9 to the individual ligands. The measured and the theoretical curve are nearly identical, with the exhibited difference attributable to dissociation of the targets in the experimental curve. The data shows that SEQ ID NO: 9 is capable of simultaneously binding all targets, hIL-17A, hIL-23 and HSA, without a loss of signal intensity or a change in kinetics compared to binding a single target only.

Example 13: Affinity of Alternative Lipocalin Muteins to IL-23

To measure the binding affinity of the lipocalin muteins SEQ ID NO: 45 and SEQ ID NO: 46 to human IL-23, a Surface Plasmon Resonance (SPR) based assay was employed utilizing a Biacore T200 instrument (GE Healthcare). In the SPR affinity assay (FIG. 13), hIL-23 was immobilized on a sensor chip using standard amine chemistry: Activation of the chip, immobilization of hIL-23, SPR measurements and data evaluation were performed as described in Example 6.

As shown in FIG. 13, the resulting fit curves demonstrate that SEQ ID NO: 45 bound with high affinity to hIL-23, with an association rate constant of $k_a=3.0\times10^5$ $M^{-1}sec^{-1}$ and a dissociation rate constant of $k_d=3\times10^{-5}$ $sec^{-1}$, resulting in a dissocation constant of $K_D=100$ pM. Similarly, as shown in FIG. 13, SEQ ID NO: 46 bound with high affinity to hIL-23, with an association rate constant of $ka=7.0\times10^4$ $M^{-1}sec^{-1}$ and a dissociation rate constant of $kd=4.0\times10^{-5}$ $sec^{-1}$, resulting in a dissocation constant of $K_D=0.6$ nM.

Example 14: Competitive Mode of Action of Lipocalin Muteins to IL-23

Whether the lipocalin muteins SEQ ID NO: 45 and SEQ ID NO: 46 bind to human IL-23 in a competitive mode was tested in vitro using a competition ELISA format (FIG. 14). The experiment and evaluation were carried out in an identical fashion compared to Example 8.

The result of the experiment is shown in FIG. 14. SEQ ID NO: 45 exhibits a competitive binding to hIL23, with a fitted IC50 value of 0.1 nM, and SEQ ID NO: 46 also displays a competitive binding to hIL23, with a fitted IC50 value of 1.1 nM.

Example 15: Lipocalin-Mutein-Mediated Blockade of IL-23 in Cell-Based Proliferation Assays The ability of the lipocalin muteins SEQ ID NO: 45 and SEQ ID NO: 46 to neutralize the biological activity of hIL-23 was assessed by the application of short-term proliferation bioassays employing cells that recombinantly express the human IL-23 receptor. The experiment and evaluation were carried out in analogy to Example 10. SEQ ID NO: 43 served as the negative control.

The result of the experiment is shown in FIG. 15. SEQ ID NO: 45 displays an average EC50 of 3.7 nM, and SEQ ID NO: 46 exhibits an EC50 of 5.4 nM. The negative control had no effect on proliferation. The data therefore demonstrates that SEQ ID NO: 2 and the lipocalin muteins of SEQ ID NO: 45 and of SEQ ID NO: 46 exhibit a comparable potency in this functional assay.

Example 16: Specificity of Fusion Protein Towards IL-17A

We employed an ELISA assay to determine the specificity of the fusion protein of SEQ ID NOs: 63 and 62 to IL-17A. Neutravidin was dissolved in PBS (5 µg/mL) and coated overnight on microtiter plates at 4° C. The plate was washed after each incubation step with 100 µL PBS supplemented with 0.1% (v/v) Tween 20 (PBS-T) five times. The plates were blocked with 2% BSA (w/v) in PBS-T (PBS-TB) for 1 h at room temperature and subsequently washed. IL-17A (Peprotech) which had been biotinylated was captured on neutravidin for 20 min at a concentration of 1 µg/ml. Unbound protein was washed off. Subsequently, different concentrations of the lipocalin mutein of SEQ ID NO: 1 or the fusion protein were added to the wells and incubated for 1 h at room temperature, followed by a wash step. Bound fusion protein or lipocalin mutein were detected after incubation with 1:2000 diluted anti-human TLc antibody conjugated to HRP in PBS-TB. After an additional wash step, fluorogenic HRP substrate (QuantaBlu, Thermo) was added to each well and the fluorescence intensity was detected using a fluorescence microplate reader.

The result of the experiment is depicted in FIG. 16, together with the fit curves resulting from a 1:1 binding sigmoidal fit, where the EC50 value and the maximum signal were free parameters, and the slope was fixed to unity. The resulting EC50 values are provided in Table 2, including the errors of the sigmoidal fit of the data. The observed EC50 values are, within the errors of the experiment, very similar for the antibody-lipocalin mutein fusion protein and the lipocalin mutein. The experiment shows that the lipocalin mutein of SEQ ID NO: 1 as included in the fusion protein can be fused to the antibody of SEQ ID NO: 61 and 62 without a loss in activity towards IL-17A.

TABLE 2

ELISA data for IL-17A binding

| Name | EC50 IL-17A [nM] |
|---|---|
| SEQ ID NO: 1 | 1.14 ± 0.10 |
| SEQ ID NOs: 63 and 62 | 1.25 ± 0.17 |

Example 17: Specificity of Fusion Protein Towards IL-23

We employed an ELISA assay to determine the specificity of the fusion protein of SEQ ID NOs: 64 and 62 towards IL-23. Neutravidin was dissolved in PBS (5 μg/mL) and coated overnight on microtiter plates at 4° C. The plate was washed after each incubation step with 100 μL PBS supplemented with 0.1% (v/v) Tween 20 (PBS-T) five times. The plates were blocked with 2% BSA (w/v) in PBS-T for 1 h at room temperature and subsequently washed. Biotinylated IL-23 was captured on neutravidin for 20 min at a concentration of 1 μg/ml. Unbound protein was washed off. Subsequently, different concentrations of the lipocalin mutein of SEQ ID NO: 2 or the fusion proteins were added to the wells and incubated for 1 h at room temperature, followed by a wash step. Bound fusion proteins or lipocalin mutein were detected after incubation with 1:1000 diluted anti-human NGAL antibody conjugated to HRP in PBS-T supplemented with 2% (w/v) BSA (PBS-TB). After an additional wash step, fluorogenic HRP substrate (QuantaBlu, Thermo) was added to each well and the fluorescence intensity was detected using a fluorescence microplate reader.

The result of the experiment is depicted in FIG. 17, together with the fit curves resulting from a 1:1 binding sigmoidal fit, where the EC50 value and the maximum signal were free parameters, and the slope was fixed to unity. The resulting EC50 values are provided in Table 3. The observed EC50 values for the antibody-lipocalin mutein fusion protein and the lipocalin mutein are very similar within the error of the experiment. This demonstrates that the lipocalin mutein of SEQ ID NO: 2 as included in the fusion protein can be fused to the antibody of SEQ ID NO: 64 and 62 without a loss in activity towards IL-23.

TABLE 3

ELISA data for IL-23 binding

| Name | EC50 IL-23 [nM] |
|---|---|
| SEQ ID NO: 2 | 1.3 ± 0.08 |
| SEQ ID NOs: 64 and 62 | 1.2 ± 0.08 |

Example 18: Specificity of Fusion Proteins Towards TNF-α

We employed an ELISA assay to determine the specificity of the fusion protein of SEQ ID NOs: 63 and 62 and the fusion protein of SEQ ID NOs: 64 and 62 to TNF-α. The antibody of SEQ ID NO: 61 and 62 served as the positive control. Recombinant TNF-α (R&D Systems, 210-TA-100/CF) was dissolved in PBS (1 μg/mL) and coated overnight on microtiter plates at 4° C. The plate was washed five times after each incubation step with 100 μL PBS-T. The plates were blocked with 2% BSA (w/v) in PBS-T for 1 h at room temperature and subsequently washed. Different concentrations of the TNFα-specific parental antibody or the fusion proteins were added to the wells and incubated for 1 h at room temperature, followed by a wash step. Bound fusion proteins or antibody were detected after incubation for 1 h at room temperature with 1:5000 diluted goat anti-human IgG Fab antibody conjugated to HRP (Jackson Laboratories) in PBS-TB. After an additional wash step, fluorogenic HRP substrate (QuantaBlu, Thermo) was added to each well and the fluorescence intensity was detected using a fluorescence microplate reader.

The result of the experiment is depicted in FIG. 18, together with the fit curves resulting from a 1:1 binding sigmoidal fit, where the EC50 value and the maximum signal were free parameters, and the slope was fixed to unity. The resulting EC50 values are provided in Table 4. The observed EC50 values for all proteins tested are very similar. This demonstrates that the antibody as included in the fusion proteins can be fused to different lipocalin muteins without compromising its activity towards TNFα.

TABLE 4

ELISA data for TNFα binding

| Name | EC50 TNFα [nM] |
|---|---|
| SEQ ID NOs: 61 and 62 | 0.16 ± 0.01 |
| SEQ ID NOs: 63 and 62 | 0.22 ± 0.01 |
| SEQ ID NOs: 64 and 62 | 0.26 ± 0.01 |

Example 19: Demonstration of Simultaneous Target Binding of Fusion Proteins in an ELISA-Based Setting In order to demonstrate the simultaneous binding of the fusion protein of SEQ ID NOs: 63 and 62 and the fusion protein of SEQ ID NOs: 64 and 62 to TNFα and IL-17A or IL-23, respectively, a dual-binding ELISA format was used. Recombinant TNF-α (R&D Systems, 210-TA-100/CF) in PBS (1 μg/mL) was coated overnight on microtiter plates at 4° C. The plate was washed five times after each incubation step with 100 μL PBS-T. The plates were blocked with 2% BSA (w/v) in PBS-T for 1 h at room temperature and subsequently washed again. Different concentrations of the fusion proteins were added to the wells and incubated for 1 h at room temperature, followed by a wash step. Subsequently, biotinylated IL-17A (in case of SEQ ID NOs: 63 and 62) or biotinylated IL-23 (in case of SEQ ID NOs: 64 and 62) were added at a constant concentration of 1 μg/mL in PBS-TB for 1 h. After washing, Extravidin-HRP (Sigma-Adrich, 1:5000 in PBS-TB) was added to the wells for 1 h. After an additional wash step, fluorogenic HRP substrate (QuantaBlu, Thermo) was added to each well and the fluorescence intensity was detected using a fluorescence microplate reader.

The result of the experiment is depicted in FIG. 19, together with the fit curves resulting from a 1:1 binding sigmoidal fit, where the EC50 value and the maximum signal were free parameters, and the slope was fixed to unity. The resulting EC50 values are provided in Table 5. All fusion proteins showed clear binding signals with EC50 values in the single digit nanomolar range, demonstrating that the fusion proteins are able to engage TNFα and either IL-17A or IL-23 simultaneously.

TABLE 5

ELISA data for simultaneous target binding

| Name | EC50 Dual binding [nM] |
|---|---|
| SEQ ID NOs: 63 and 62 | 2.70 ± 0.22 |
| SEQ ID NOs: 64 and 62 | 1.54 ± 0.16 |

Embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention. Thus, it should be understood that although the present embodiments have been specifically disclosed by preferred embodiments and optional features, modification and variations thereof may be resorted to by those skilled in the art, and that such modifications and variations are considered to be within the scope of the invention. All patents, patent applications, textbooks and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims.

Equivalents: Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference.

The invention claimed is:

1. A lipocalin mutein having binding specificity for IL-23p19, wherein the mutein binds IL-23 with a $K_D$ of about 1 nM or lower, wherein the mutein has at least 85% identity to an amino acid sequence selected from the group consisting of SEQ ID NOs: 2 and 45-46, and wherein the mutein comprises one of the following sets of amino acid substitutions in comparison with the linear polypeptide sequence of the mature human neutrophil gelatinase-associated lipocalin (NGAL) (SEQ ID NO: 43):

(1) Gln 28→His; Leu 36→Glu; Ala 40→Leu; Ile 41→Leu; Gln 49→Arg; Tyr 52→Thr; Asn 65→Asp; Ser 68→Arg; Leu 70→Glu; Arg 72→Gly; Lys 73→Ala; Lys 75→Thr; Cys 76→Tyr; Asp 77→Lys; Trp 79→Gln; Arg 81→Gly; Asn 96→Gly; Lys 98→Glu; Tyr 100→Met; Leu 103→Met; Tyr 106→Phe; Met 120→Ile; Lys 125→Tyr; Ser 127→Tyr; and Lys 134→Glu;

(2) Gln 28→His; Leu 36→Glu; Ala 40→Leu; Gln 49→Arg; Tyr 52→Thr; Asn 65→Asp; Ser 68→Arg; Leu 70→Glu; Arg 72→Gly; Lys 73→Val; Lys 75→Thr; Cys 76→Arg; Asp 77→Lys; Trp 79→Arg; Arg 81→Gly; Asn 96→Gly; Tyr 100→Met; Leu 103→Met; Tyr 106→Phe; Lys 125→Tyr; Ser 127→Tyr; and Lys 134→Glu; or (3) Gln 28→His; Leu 36→Glu; Ala 40→Leu; Ile 41→Leu; Gln 49→Arg; Tyr 52→Thr; Asn 65→Asp; Ser 68→Arg; Leu 70→Glu; Arg 72→Gly; Lys 73→Val; Lys 75→Thr; Cys 76→Tyr; Asp 77→Lys; Trp 79→Gln; Arg 81→Gly; Asn 96→Gly; Tyr 100→Met; Leu 103→Met; Tyr 106→Phe; Asn 114→Asp; Lys 125→Tyr; Ser 127→Tyr; and Lys 134→Glu.

2. The mutein of claim 1, wherein said mutein is cross-reactive with both human IL-23 and mouse IL-23.

3. The mutein of claim 1, wherein the mutein has at least 90% identity to an amino acid sequence selected from the group consisting of SEQ ID NOs: 2 and 45-46.

4. A composition comprising a mutein of claim 1.

5. A method of binding IL-23 in a subject, comprising administering to said subject an effective amount of one or more muteins of claim 1, or of one or more compositions comprising such muteins.

6. A method for inhibiting the binding of IL-23 to its receptor in a subject, comprising administering to said subject an effective amount of one or more muteins of claim 1, or of one or more compositions comprising such muteins.

7. A kit comprising at least one mutein of claim 1, and one or more instructions for using the kit.

8. A nucleic acid molecule comprising a nucleotide sequence encoding a mutein of claim 1.

9. A host cell containing a nucleic acid molecule of claim 8.

10. A method of producing a mutein of claim 1, wherein the mutein is produced starting from the nucleic acid coding for the mutein by means of genetic engineering methods.

11. The mutein of claim 1, wherein the mutein is capable of inhibiting the binding of IL-23 to its receptor IL-23R.

12. The mutein of claim 1, wherein the mutein is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxin, a metal complex, a metal, colloidal gold, and a moiety that extends the serum half-life of the mutein.

13. The mutein of claim 1, wherein the mutein is fused at its N-terminus and/or its C-terminus to a moiety which is a protein, a protein domain, or a peptide, or to a second subunit selected from the group consisting of a subunit having binding specificity for IL-17A, a subunit containing an albumin binding domain (ABD) or an albumin binding peptide, an Fc-part of a human antibody, and a subunit containing a TNF-inhibiting protein.

14. The mutein of claim 1, wherein the mutein comprises an amino acid sequence selected from the group consisting of SEQ ID NOs: 2 and 45-46.

* * * * *

SEQUENCE LISTING

<160> NUMBER OF SEQ ID NOS: 68

<210> SEQ ID NO 1
<211> LENGTH: 151
<212> TYPE: PRT
<213> ORGANISM: artificial
<220> FEATURE:
<223> OTHER INFORMATION: lipocalin mutein

<400> SEQUENCE: 1

Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Glu Gly Phe Leu Gln Glu Phe Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser Arg Val Lys Asp His Tyr Ile Phe Tyr
                85                  90                  95

-continued

Ser Glu Gly Asp Cys Pro Gly Pro Val Pro Val Trp Leu Val Gly
            100                 105                 110

Arg Asp Pro Lys Asn Asn Leu Glu Ala Leu Glu Asp Phe Glu Lys Ala
        115                 120                 125

Ala Gly Ala Arg Gly Leu Ser Thr Glu Ser Ile Leu Ile Pro Arg Gln
    130                 135                 140

Ser Glu Thr Ser Ser Pro Gly
145             150

<210> SEQ ID NO 2
<211> LENGTH: 178
<212> TYPE: PRT
<213> ORGANISM: artificial
<220> FEATURE:
<223> OTHER INFORMATION: lipocalin mutein

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Leu Leu Arg Glu Asp Lys Asp Pro
        35                  40                  45

Arg Lys Met Thr Ala Thr Ile Tyr Glu Leu Lys Glu Asp Lys Ser Tyr
    50                  55                  60

Asp Val Thr Arg Val Glu Phe Gly Ala Lys Thr Tyr Lys Tyr Gln Ile
65                  70                  75                  80

Gly Thr Phe Val Pro Gly Ser Gln Pro Gly Phe Thr Leu Gly Gly
                85                  90                  95

Ile Glu Ser Met Pro Gly Met Thr Ser Phe Leu Val Arg Val Val Ser
            100                 105                 110

Thr Asn Tyr Asn Gln His Ala Ile Val Phe Phe Lys Tyr Val Tyr Gln
        115                 120                 125

Asn Arg Glu Tyr Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ala Ile
                165                 170                 175

Asp Gly

<210> SEQ ID NO 3
<211> LENGTH: 351
<212> TYPE: PRT
<213> ORGANISM: artificial
<220> FEATURE:
<223> OTHER INFORMATION: fusion protein

<400> SEQUENCE: 3

Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Glu Gly Phe Leu Gln Glu Phe Lys Ala Val Leu
    50                  55                  60

```
Glu Lys Thr Asp Glu Pro Gly Lys Tyr Thr Ala Asp Gly Gly Lys His
 65                  70                  75                  80

Val Ala Tyr Ile Ile Arg Ser Arg Val Lys Asp His Tyr Ile Phe Tyr
                 85                  90                  95

Ser Glu Gly Asp Cys Pro Gly Pro Val Pro Gly Val Trp Leu Val Gly
                100                 105                 110

Arg Asp Pro Lys Asn Asn Leu Glu Ala Leu Glu Asp Phe Glu Lys Ala
            115                 120                 125

Ala Gly Ala Arg Gly Leu Ser Thr Glu Ser Ile Leu Ile Pro Arg Gln
            130                 135                 140

Ser Glu Thr Ser Ser Pro Gly Ser Asp Gly Gly Gly Ser Gly Gly
145                 150                 155                 160

Gly Gly Ser Gln Asp Ser Thr Ser Asp Leu Ile Pro Ala Pro Pro Leu
                165                 170                 175

Ser Lys Val Pro Leu Gln Gln Asn Phe Gln Asp Asn Gln Phe His Gly
                180                 185                 190

Lys Trp Tyr Val Val Gly Glu Ala Gly Asn Leu Leu Leu Arg Glu Asp
            195                 200                 205

Lys Asp Pro Arg Lys Met Thr Ala Thr Ile Tyr Glu Leu Lys Glu Asp
210                 215                 220

Lys Ser Tyr Asp Val Thr Arg Val Glu Phe Gly Ala Lys Thr Tyr Lys
225                 230                 235                 240

Tyr Gln Ile Gly Thr Phe Val Pro Gly Ser Gln Pro Gly Glu Phe Thr
                245                 250                 255

Leu Gly Gly Ile Glu Ser Met Pro Gly Met Thr Ser Phe Leu Val Arg
            260                 265                 270

Val Val Ser Thr Asn Tyr Asn Gln His Ala Ile Val Phe Phe Lys Tyr
            275                 280                 285

Val Tyr Gln Asn Arg Glu Tyr Phe Glu Ile Thr Leu Tyr Gly Arg Thr
            290                 295                 300

Lys Glu Leu Thr Ser Glu Leu Lys Glu Asn Phe Ile Arg Phe Ser Lys
305                 310                 315                 320

Ser Leu Gly Leu Pro Glu Asn His Ile Val Phe Pro Val Pro Ile Asp
                325                 330                 335

Gln Ala Ile Asp Gly Ser Ala Trp Ser His Pro Gln Phe Glu Lys
            340                 345                 350

<210> SEQ ID NO 4
<211> LENGTH: 349
<212> TYPE: PRT
<213> ORGANISM: artificial
<220> FEATURE:
<223> OTHER INFORMATION: fusion protein

<400> SEQUENCE: 4

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                 20                  25                  30

Val Val Gly Glu Ala Gly Asn Leu Leu Leu Arg Glu Asp Lys Asp Pro
             35                  40                  45

Arg Lys Met Thr Ala Thr Ile Tyr Glu Leu Lys Glu Asp Lys Ser Tyr
         50                  55                  60

Asp Val Thr Arg Val Glu Phe Gly Ala Lys Thr Tyr Lys Tyr Gln Ile
 65                  70                  75                  80
```

```
Gly Thr Phe Val Pro Gly Ser Gln Pro Gly Glu Phe Thr Leu Gly Gly
                85                  90                  95

Ile Glu Ser Met Pro Gly Met Thr Ser Phe Leu Val Arg Val Val Ser
            100                 105                 110

Thr Asn Tyr Asn Gln His Ala Ile Val Phe Lys Tyr Val Tyr Gln
        115                 120                 125

Asn Arg Glu Tyr Phe Glu Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ala Ile
                165                 170                 175

Asp Gly Gly Gly Gly Ser Gly Gly Gly Ser Ala Ser Asp Glu
            180                 185                 190

Glu Ile Gln Asp Val Ser Gly Thr Trp Tyr Leu Lys Ala Met Thr Val
            195                 200                 205

Asp Phe Trp Cys Ser Gly Ile His Glu Glu Ser Val Thr Pro Met Thr
        210                 215                 220

Leu Thr Thr Leu Glu Gly Gly Asn Leu Glu Ala Lys Val Thr Met Asp
225                 230                 235                 240

Ile Glu Gly Phe Leu Gln Glu Phe Lys Ala Val Leu Glu Lys Thr Asp
                245                 250                 255

Glu Pro Gly Lys Tyr Thr Ala Asp Gly Gly Lys His Val Ala Tyr Ile
            260                 265                 270

Ile Arg Ser Arg Val Lys Asp His Tyr Ile Phe Tyr Ser Glu Gly Asp
        275                 280                 285

Cys Pro Gly Pro Val Pro Gly Val Trp Leu Val Gly Arg Asp Pro Lys
290                 295                 300

Asn Asn Leu Glu Ala Leu Glu Asp Phe Glu Lys Ala Ala Gly Ala Arg
305                 310                 315                 320

Gly Leu Ser Thr Glu Ser Ile Leu Ile Pro Arg Gln Ser Glu Thr Ser
                325                 330                 335

Ser Pro Gly Ser Ala Trp Ser His Pro Gln Phe Glu Lys
            340                 345

<210> SEQ ID NO 5
<211> LENGTH: 406
<212> TYPE: PRT
<213> ORGANISM: artificial
<220> FEATURE:
<223> OTHER INFORMATION: fusion protein

<400> SEQUENCE: 5

Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Glu Gly Phe Leu Gln Glu Phe Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser Arg Val Lys Asp His Tyr Ile Phe Tyr
                85                  90                  95
```

```
Ser Glu Gly Asp Cys Pro Gly Pro Val Pro Gly Val Trp Leu Val Gly
            100                 105                 110

Arg Asp Pro Lys Asn Asn Leu Glu Ala Leu Glu Asp Phe Glu Lys Ala
        115                 120                 125

Ala Gly Ala Arg Gly Leu Ser Thr Glu Ser Ile Leu Ile Pro Arg Gln
    130                 135                 140

Ser Glu Thr Ser Ser Pro Gly Ser Asp Gly Gly Gly Ser Gly Gly
145                 150                 155                 160

Gly Gly Ser Gln Asp Ser Thr Ser Asp Leu Ile Pro Ala Pro Pro Leu
                165                 170                 175

Ser Lys Val Pro Leu Gln Gln Asn Phe Gln Asp Asn Gln Phe His Gly
            180                 185                 190

Lys Trp Tyr Val Val Gly Glu Ala Gly Asn Leu Leu Leu Arg Glu Asp
        195                 200                 205

Lys Asp Pro Arg Lys Met Thr Ala Thr Ile Tyr Glu Leu Lys Glu Asp
    210                 215                 220

Lys Ser Tyr Asp Val Thr Arg Val Glu Phe Gly Ala Lys Thr Tyr Lys
225                 230                 235                 240

Tyr Gln Ile Gly Thr Phe Val Pro Gly Ser Gln Pro Gly Glu Phe Thr
                245                 250                 255

Leu Gly Gly Ile Glu Ser Met Pro Gly Met Thr Ser Phe Leu Val Arg
            260                 265                 270

Val Val Ser Thr Asn Tyr Asn Gln His Ala Ile Val Phe Phe Lys Tyr
        275                 280                 285

Val Tyr Gln Asn Arg Glu Tyr Phe Glu Ile Thr Leu Tyr Gly Arg Thr
    290                 295                 300

Lys Glu Leu Thr Ser Glu Leu Lys Glu Asn Phe Ile Arg Phe Ser Lys
305                 310                 315                 320

Ser Leu Gly Leu Pro Glu Asn His Ile Val Phe Pro Val Pro Ile Asp
                325                 330                 335

Gln Ala Ile Asp Gly Ser Ala Gly Ala Val Asp Ala Asn Ser Leu Ala
            340                 345                 350

Glu Ala Lys Val Leu Ala Asn Arg Glu Leu Asp Lys Tyr Gly Val Ser
        355                 360                 365

Asp Tyr Tyr Lys Asn Leu Ile Asn Asn Ala Lys Thr Val Glu Gly Val
    370                 375                 380

Lys Ala Leu Ile Asp Glu Ile Leu Ala Ala Leu Pro Ser Ala Trp Ser
385                 390                 395                 400

His Pro Gln Phe Glu Lys
                405

<210> SEQ ID NO 6
<211> LENGTH: 556
<212> TYPE: PRT
<213> ORGANISM: artificial
<220> FEATURE:
<223> OTHER INFORMATION: fusion protein

<400> SEQUENCE: 6

Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45
```

```
Val Thr Met Asp Ile Glu Gly Phe Leu Gln Glu Phe Lys Ala Val Leu
    50                  55                  60
Glu Lys Thr Asp Glu Pro Gly Lys Tyr Thr Ala Asp Gly Gly Lys His
65                  70                  75                  80
Val Ala Tyr Ile Ile Arg Ser Arg Val Lys Asp His Tyr Ile Phe Tyr
                85                  90                  95
Ser Glu Gly Asp Cys Pro Gly Pro Val Pro Gly Val Trp Leu Val Gly
                100                 105                 110
Arg Asp Pro Lys Asn Asn Leu Glu Ala Leu Glu Asp Phe Glu Lys Ala
                115                 120                 125
Ala Gly Ala Arg Gly Leu Ser Thr Glu Ser Ile Leu Ile Pro Arg Gln
130                 135                 140
Ser Glu Thr Ser Ser Pro Gly Ser Asp Gly Gly Gly Ser Gly Gly
145                 150                 155                 160
Gly Gly Ser Ala Ser Asp Glu Ile Gln Asp Val Ser Gly Thr Trp
                165                 170                 175
Tyr Leu Lys Ala Met Thr Val Asp Phe Trp Cys Ser Gly Ile His Glu
                180                 185                 190
Glu Ser Val Thr Pro Met Thr Leu Thr Thr Leu Glu Gly Gly Asn Leu
                195                 200                 205
Glu Ala Lys Val Thr Met Asp Ile Glu Gly Phe Leu Gln Glu Phe Lys
210                 215                 220
Ala Val Leu Glu Lys Thr Asp Glu Pro Gly Lys Tyr Thr Ala Asp Gly
225                 230                 235                 240
Gly Lys His Val Ala Tyr Ile Ile Arg Ser Arg Val Lys Asp His Tyr
                245                 250                 255
Ile Phe Tyr Ser Glu Gly Asp Cys Pro Gly Pro Val Pro Gly Val Trp
                260                 265                 270
Leu Val Gly Arg Asp Pro Lys Asn Asn Leu Glu Ala Leu Glu Asp Phe
                275                 280                 285
Glu Lys Ala Ala Gly Ala Arg Gly Leu Ser Thr Glu Ser Ile Leu Ile
290                 295                 300
Pro Arg Gln Ser Glu Thr Ser Ser Pro Gly Ser Asp Gly Gly Gly Gly
305                 310                 315                 320
Ser Gly Gly Gly Gly Ser Gln Asp Ser Thr Ser Asp Leu Ile Pro Ala
                325                 330                 335
Pro Pro Leu Ser Lys Val Pro Leu Gln Gln Asn Phe Gln Asp Asn Gln
                340                 345                 350
Phe His Gly Lys Trp Tyr Val Val Gly Glu Ala Gly Asn Leu Leu Leu
                355                 360                 365
Arg Glu Asp Lys Asp Pro Arg Lys Met Thr Ala Thr Ile Tyr Glu Leu
                370                 375                 380
Lys Glu Asp Lys Ser Tyr Asp Val Thr Arg Val Glu Phe Gly Ala Lys
385                 390                 395                 400
Thr Tyr Lys Tyr Gln Ile Gly Thr Phe Val Pro Gly Ser Gln Pro Gly
                405                 410                 415
Glu Phe Thr Leu Gly Gly Ile Glu Ser Met Pro Gly Met Thr Ser Phe
                420                 425                 430
Leu Val Arg Val Val Ser Thr Asn Tyr Asn Gln His Ala Ile Val Phe
                435                 440                 445
Phe Lys Tyr Val Tyr Gln Asn Arg Glu Tyr Phe Glu Ile Thr Leu Tyr
450                 455                 460
```

```
Gly Arg Thr Lys Glu Leu Thr Ser Glu Leu Lys Glu Asn Phe Ile Arg
465                 470                 475                 480

Phe Ser Lys Ser Leu Gly Leu Pro Glu Asn His Ile Val Phe Pro Val
            485                 490                 495

Pro Ile Asp Gln Ala Ile Asp Gly Ser Gly Gly Gly Ser Leu Ala
            500                 505                 510

Glu Ala Lys Glu Ala Ala Asn Ala Glu Leu Asp Ser Tyr Gly Val Ser
            515                 520                 525

Asp Phe Tyr Lys Arg Leu Ile Asp Lys Ala Lys Thr Val Glu Gly Val
            530                 535                 540

Glu Ala Leu Lys Asp Ala Ile Leu Ala Ala Leu Pro
545                 550                 555

<210> SEQ ID NO 7
<211> LENGTH: 240
<212> TYPE: PRT
<213> ORGANISM: artificial
<220> FEATURE:
<223> OTHER INFORMATION: fusion protein

<400> SEQUENCE: 7

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Leu Leu Arg Glu Asp Lys Asp Pro
            35                  40                  45

Arg Lys Met Thr Ala Thr Ile Tyr Glu Leu Lys Glu Asp Lys Ser Tyr
50                  55                  60

Asp Val Thr Arg Val Glu Phe Gly Ala Lys Thr Tyr Lys Tyr Gln Ile
65                  70                  75                  80

Gly Thr Phe Val Pro Gly Ser Gln Pro Gly Glu Phe Thr Leu Gly Gly
            85                  90                  95

Ile Glu Ser Met Pro Gly Met Thr Ser Phe Leu Val Arg Val Val Ser
            100                 105                 110

Thr Asn Tyr Asn Gln His Ala Ile Val Phe Phe Lys Tyr Val Tyr Gln
            115                 120                 125

Asn Arg Glu Tyr Phe Glu Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ala Ile
                165                 170                 175

Asp Gly Ser Gly Gly Gly Ser Leu Ala Glu Ala Lys Glu Ala Ala
            180                 185                 190

Asn Ala Glu Leu Asp Ser Tyr Gly Val Ser Asp Phe Tyr Lys Arg Leu
            195                 200                 205

Ile Asp Lys Ala Lys Thr Val Glu Gly Val Glu Ala Leu Lys Asp Ala
210                 215                 220

Ile Leu Ala Ala Leu Pro Ser Ala Trp Ser His Pro Gln Phe Glu Lys
225                 230                 235                 240

<210> SEQ ID NO 8
<211> LENGTH: 215
<212> TYPE: PRT
<213> ORGANISM: artificial
```

-continued

<220> FEATURE:
<223> OTHER INFORMATION: fusion protein

<400> SEQUENCE: 8

```
Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Glu Gly Phe Leu Gln Glu Phe Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser Arg Val Lys Asp His Tyr Ile Phe Tyr
                85                  90                  95

Ser Glu Gly Asp Cys Pro Gly Pro Val Pro Gly Val Trp Leu Val Gly
            100                 105                 110

Arg Asp Pro Lys Asn Asn Leu Glu Ala Leu Glu Asp Phe Glu Lys Ala
        115                 120                 125

Ala Gly Ala Arg Gly Leu Ser Thr Glu Ser Ile Leu Ile Pro Arg Gln
    130                 135                 140

Ser Glu Thr Ser Ser Pro Gly Ser Asp Ser Gly Gly Gly Gly Ser Leu
145                 150                 155                 160

Ala Glu Ala Lys Glu Ala Ala Asn Ala Glu Leu Asp Ser Tyr Gly Val
                165                 170                 175

Ser Asp Phe Tyr Lys Arg Leu Ile Asp Lys Ala Lys Thr Val Glu Gly
            180                 185                 190

Val Glu Ala Leu Lys Asp Ala Ile Leu Ala Ala Leu Pro Ser Ala Trp
        195                 200                 205

Ser His Pro Gln Phe Glu Lys
    210                 215
```

<210> SEQ ID NO 9
<211> LENGTH: 403
<212> TYPE: PRT
<213> ORGANISM: artificial
<220> FEATURE:
<223> OTHER INFORMATION: fusion protein

<400> SEQUENCE: 9

```
Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Glu Gly Phe Leu Gln Glu Phe Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser Arg Val Lys Asp His Tyr Ile Phe Tyr
                85                  90                  95

Ser Glu Gly Asp Cys Pro Gly Pro Val Pro Gly Val Trp Leu Val Gly
            100                 105                 110
```

```
Arg Asp Pro Lys Asn Asn Leu Glu Ala Leu Glu Asp Phe Glu Lys Ala
            115                 120                 125

Ala Gly Ala Arg Gly Leu Ser Thr Glu Ser Ile Leu Ile Pro Arg Gln
        130                 135                 140

Ser Glu Thr Ser Ser Pro Gly Ser Asp Gly Gly Gly Ser Gly Gly Gly
145                 150                 155                 160

Gly Gly Ser Gln Asp Ser Thr Ser Asp Leu Ile Pro Ala Pro Pro Leu
                165                 170                 175

Ser Lys Val Pro Leu Gln Gln Asn Phe Gln Asp Asn Gln Phe His Gly
                180                 185                 190

Lys Trp Tyr Val Val Gly Glu Ala Gly Asn Leu Leu Leu Arg Glu Asp
        195                 200                 205

Lys Asp Pro Arg Lys Met Thr Ala Thr Ile Tyr Glu Leu Lys Glu Asp
    210                 215                 220

Lys Ser Tyr Asp Val Thr Arg Val Glu Phe Gly Ala Lys Thr Tyr Lys
225                 230                 235                 240

Tyr Gln Ile Gly Thr Phe Val Pro Gly Ser Gln Pro Gly Glu Phe Thr
                245                 250                 255

Leu Gly Gly Ile Glu Ser Met Pro Gly Met Thr Ser Phe Leu Val Arg
        260                 265                 270

Val Val Ser Thr Asn Tyr Asn Gln His Ala Ile Val Phe Phe Lys Tyr
    275                 280                 285

Val Tyr Gln Asn Arg Glu Tyr Phe Glu Ile Thr Leu Tyr Gly Arg Thr
290                 295                 300

Lys Glu Leu Thr Ser Glu Leu Lys Glu Asn Phe Ile Arg Phe Ser Lys
305                 310                 315                 320

Ser Leu Gly Leu Pro Glu Asn His Ile Val Phe Pro Val Pro Ile Asp
                325                 330                 335

Gln Ala Ile Asp Gly Ser Gly Gly Gly Ser Leu Ala Glu Ala Lys
                340                 345                 350

Glu Ala Ala Asn Ala Glu Leu Asp Ser Tyr Gly Val Ser Asp Phe Tyr
        355                 360                 365

Lys Arg Leu Ile Asp Lys Ala Lys Thr Val Glu Gly Val Glu Ala Leu
    370                 375                 380

Lys Asp Ala Ile Leu Ala Ala Leu Pro Ser Ala Trp Ser His Pro Gln
385                 390                 395                 400

Phe Glu Lys

<210> SEQ ID NO 10
<211> LENGTH: 378
<212> TYPE: PRT
<213> ORGANISM: artificial
<220> FEATURE:
<223> OTHER INFORMATION: fusion protein

<400> SEQUENCE: 10

Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Glu Gly Phe Leu Gln Glu Phe Lys Ala Val Leu
    50                  55                  60
```

```
Glu Lys Thr Asp Glu Pro Gly Lys Tyr Thr Ala Asp Gly Gly Lys His
 65                  70                  75                  80

Val Ala Tyr Ile Ile Arg Ser Arg Val Lys Asp His Tyr Ile Phe Tyr
                 85                  90                  95

Ser Glu Gly Asp Cys Pro Gly Pro Val Pro Gly Val Trp Leu Val Gly
            100                 105                 110

Arg Asp Pro Lys Asn Asn Leu Glu Ala Leu Glu Asp Phe Glu Lys Ala
        115                 120                 125

Ala Gly Ala Arg Gly Leu Ser Thr Glu Ser Ile Leu Ile Pro Arg Gln
    130                 135                 140

Ser Glu Thr Ser Ser Pro Gly Ser Asp Gly Gly Gly Ser Gly Gly
145                 150                 155                 160

Gly Gly Ser Ala Ser Asp Glu Glu Ile Gln Asp Val Ser Gly Thr Trp
                165                 170                 175

Tyr Leu Lys Ala Met Thr Val Asp Phe Trp Cys Ser Gly Ile His Glu
            180                 185                 190

Glu Ser Val Thr Pro Met Thr Leu Thr Thr Leu Glu Gly Gly Asn Leu
        195                 200                 205

Glu Ala Lys Val Thr Met Asp Ile Glu Gly Phe Leu Gln Glu Phe Lys
    210                 215                 220

Ala Val Leu Glu Lys Thr Asp Glu Pro Gly Lys Tyr Thr Ala Asp Gly
225                 230                 235                 240

Gly Lys His Val Ala Tyr Ile Ile Arg Ser Arg Val Lys Asp His Tyr
                245                 250                 255

Ile Phe Tyr Ser Glu Gly Asp Cys Pro Gly Pro Val Pro Gly Val Trp
            260                 265                 270

Leu Val Gly Arg Asp Pro Lys Asn Asn Leu Glu Ala Leu Glu Asp Phe
        275                 280                 285

Glu Lys Ala Ala Gly Ala Arg Gly Leu Ser Thr Glu Ser Ile Leu Ile
    290                 295                 300

Pro Arg Gln Ser Glu Thr Ser Ser Pro Gly Ser Asp Ser Gly Gly Gly
305                 310                 315                 320

Gly Ser Leu Ala Glu Ala Lys Glu Ala Ala Asn Ala Glu Leu Asp Ser
                325                 330                 335

Tyr Gly Val Ser Asp Phe Tyr Lys Arg Leu Ile Asp Lys Ala Lys Thr
            340                 345                 350

Val Glu Gly Val Glu Ala Leu Lys Asp Ala Ile Leu Ala Ala Leu Pro
        355                 360                 365

Ser Ala Trp Ser His Pro Gln Phe Glu Lys
    370                 375

<210> SEQ ID NO 11
<211> LENGTH: 390
<212> TYPE: PRT
<213> ORGANISM: artificial
<220> FEATURE:
<223> OTHER INFORMATION: fusion protein

<400> SEQUENCE: 11

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45
```

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Ser Ala Ser Asp
225                 230                 235                 240

Glu Glu Ile Gln Asp Val Ser Gly Thr Trp Tyr Leu Lys Ala Met Thr
                245                 250                 255

Val Asp Phe Trp Cys Ser Gly Ile His Glu Glu Ser Val Thr Pro Met
            260                 265                 270

Thr Leu Thr Thr Leu Glu Gly Gly Asn Leu Glu Ala Lys Val Thr Met
    275                 280                 285

Asp Ile Glu Gly Phe Leu Gln Glu Phe Lys Ala Val Leu Glu Lys Thr
290                 295                 300

Asp Glu Pro Gly Lys Tyr Thr Ala Asp Gly Gly Lys His Val Ala Tyr
305                 310                 315                 320

Ile Ile Arg Ser Arg Val Lys Asp His Tyr Ile Phe Tyr Ser Glu Gly
                325                 330                 335

Asp Cys Pro Gly Pro Val Pro Gly Val Trp Leu Val Gly Arg Asp Pro
            340                 345                 350

Lys Asn Asn Leu Glu Ala Leu Glu Asp Phe Glu Lys Ala Ala Gly Ala
        355                 360                 365

Arg Gly Leu Ser Thr Glu Ser Ile Leu Ile Pro Arg Gln Ser Glu Thr
    370                 375                 380

Ser Ser Pro Gly Ser Asp
385                 390

<210> SEQ ID NO 12
<211> LENGTH: 553
<212> TYPE: PRT
<213> ORGANISM: artificial
<220> FEATURE:
<223> OTHER INFORMATION: fusion protein

<400> SEQUENCE: 12

```
Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Glu Gly Phe Leu Gln Glu Phe Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser Arg Val Lys Asp His Tyr Ile Phe Tyr
                85                  90                  95

Ser Glu Gly Asp Cys Pro Gly Pro Val Pro Gly Val Trp Leu Val Gly
            100                 105                 110

Arg Asp Pro Lys Asn Asn Leu Glu Ala Leu Glu Asp Phe Glu Lys Ala
        115                 120                 125

Ala Gly Ala Arg Gly Leu Ser Thr Glu Ser Ile Leu Ile Pro Arg Gln
    130                 135                 140

Ser Glu Thr Ser Ser Pro Gly Ser Asp Gly Gly Gly Ser Gly Gly
145                 150                 155                 160

Gly Gly Ser Asp Lys Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
    210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Glu Glu Met Thr Lys Asn
    290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
    370                 375                 380

Ser Leu Ser Pro Gly Lys Gly Gly Gly Ser Gly Gly Gly Gly Ser
385                 390                 395                 400

Ala Ser Asp Glu Glu Ile Gln Asp Val Ser Gly Thr Trp Tyr Leu Lys
                405                 410                 415
```

```
Ala Met Thr Val Asp Phe Trp Cys Ser Gly Ile His Glu Glu Ser Val
            420                 425                 430

Thr Pro Met Thr Leu Thr Leu Glu Gly Gly Asn Leu Glu Ala Lys
        435                 440                 445

Val Thr Met Asp Ile Glu Gly Phe Leu Gln Glu Phe Lys Ala Val Leu
    450                 455                 460

Glu Lys Thr Asp Glu Pro Gly Lys Tyr Thr Ala Asp Gly Lys His
465                 470                 475                 480

Val Ala Tyr Ile Ile Arg Ser Arg Val Lys Asp His Tyr Ile Phe Tyr
                485                 490                 495

Ser Glu Gly Asp Cys Pro Gly Pro Val Pro Gly Val Trp Leu Val Gly
            500                 505                 510

Arg Asp Pro Lys Asn Asn Leu Glu Ala Leu Glu Asp Phe Glu Lys Ala
        515                 520                 525

Ala Gly Ala Arg Gly Leu Ser Thr Glu Ser Ile Leu Ile Pro Arg Gln
    530                 535                 540

Ser Glu Thr Ser Ser Pro Gly Ser Asp
545                 550
```

<210> SEQ ID NO 13
<211> LENGTH: 553
<212> TYPE: PRT
<213> ORGANISM: artificial
<220> FEATURE:
<223> OTHER INFORMATION: fusion protein

<400> SEQUENCE: 13

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

```
Pro Gly Lys Gly Gly Gly Ser Gly Gly Gly Ser Ala Ser Asp
225                 230                 235                 240

Glu Glu Ile Gln Asp Val Ser Gly Thr Trp Tyr Leu Lys Ala Met Thr
            245                 250                 255

Val Asp Phe Trp Cys Ser Gly Ile His Glu Glu Ser Val Thr Pro Met
                260                 265                 270

Thr Leu Thr Thr Leu Glu Gly Gly Asn Leu Glu Ala Lys Val Thr Met
        275                 280                 285

Asp Ile Glu Gly Phe Leu Gln Glu Phe Lys Ala Val Leu Glu Lys Thr
        290                 295                 300

Asp Glu Pro Gly Lys Tyr Thr Ala Asp Gly Gly Lys His Val Ala Tyr
305                 310                 315                 320

Ile Ile Arg Ser Arg Val Lys Asp His Tyr Ile Phe Tyr Ser Glu Gly
                325                 330                 335

Asp Cys Pro Gly Pro Val Pro Gly Val Trp Leu Val Gly Arg Asp Pro
                340                 345                 350

Lys Asn Asn Leu Glu Ala Leu Glu Asp Phe Glu Lys Ala Ala Gly Ala
                355                 360                 365

Arg Gly Leu Ser Thr Glu Ser Ile Leu Ile Pro Arg Gln Ser Glu Thr
            370                 375                 380

Ser Ser Pro Gly Ser Asp Gly Gly Gly Ser Gly Gly Gly Gly Ser
385                 390                 395                 400

Ala Ser Asp Glu Glu Ile Gln Asp Val Ser Gly Thr Trp Tyr Leu Lys
                405                 410                 415

Ala Met Thr Val Asp Phe Trp Cys Ser Gly Ile His Glu Glu Ser Val
            420                 425                 430

Thr Pro Met Thr Leu Thr Thr Leu Glu Gly Gly Asn Leu Glu Ala Lys
        435                 440                 445

Val Thr Met Asp Ile Glu Gly Phe Leu Gln Glu Phe Lys Ala Val Leu
        450                 455                 460

Glu Lys Thr Asp Glu Pro Gly Lys Tyr Thr Ala Asp Gly Gly Lys His
465                 470                 475                 480

Val Ala Tyr Ile Ile Arg Ser Arg Val Lys Asp His Tyr Ile Phe Tyr
                485                 490                 495

Ser Glu Gly Asp Cys Pro Gly Pro Val Pro Gly Val Trp Leu Val Gly
                500                 505                 510

Arg Asp Pro Lys Asn Asn Leu Glu Ala Leu Glu Asp Phe Glu Lys Ala
            515                 520                 525

Ala Gly Ala Arg Gly Leu Ser Thr Glu Ser Ile Leu Ile Pro Arg Gln
        530                 535                 540

Ser Glu Thr Ser Ser Pro Gly Ser Asp
545                 550

<210> SEQ ID NO 14
<211> LENGTH: 55
<212> TYPE: PRT
<213> ORGANISM: artificial
<220> FEATURE:
<223> OTHER INFORMATION: albumin binding domain

<400> SEQUENCE: 14

Ser Ala Gly Ala Val Asp Ala Asn Ser Leu Ala Glu Ala Lys Val Leu
1               5                   10                  15

Ala Asn Arg Glu Leu Asp Lys Tyr Gly Val Ser Asp Tyr Tyr Lys Asn
            20                  25                  30
```

Leu Ile Asn Asn Ala Lys Thr Val Glu Gly Val Lys Ala Leu Ile Asp
            35                  40                  45

Glu Ile Leu Ala Ala Leu Pro
 50                  55

<210> SEQ ID NO 15
<211> LENGTH: 52
<212> TYPE: PRT
<213> ORGANISM: artificial
<220> FEATURE:
<223> OTHER INFORMATION: albumin binding domain

<400> SEQUENCE: 15

Ser Gly Gly Gly Gly Ser Leu Ala Glu Ala Lys Glu Ala Ala Asn Ala
 1               5                  10                  15

Glu Leu Asp Ser Tyr Gly Val Ser Asp Phe Tyr Lys Arg Leu Ile Asp
             20                  25                  30

Lys Ala Lys Thr Val Glu Gly Val Glu Ala Leu Lys Asp Ala Ile Leu
         35                  40                  45

Ala Ala Leu Pro
     50

<210> SEQ ID NO 16
<211> LENGTH: 227
<212> TYPE: PRT
<213> ORGANISM: artificial
<220> FEATURE:
<223> OTHER INFORMATION: Fc portion

<400> SEQUENCE: 16

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 17
<211> LENGTH: 10
<212> TYPE: PRT
<213> ORGANISM: artificial
<220> FEATURE:
<223> OTHER INFORMATION: protein tag

<400> SEQUENCE: 17

Ser Ala Trp Ser His Pro Gln Phe Glu Lys
1               5                   10

<210> SEQ ID NO 18
<211> LENGTH: 12
<212> TYPE: PRT
<213> ORGANISM: artificial
<220> FEATURE:
<223> OTHER INFORMATION: synthetic linker

<400> SEQUENCE: 18

Ser Asp Gly Gly Gly Gly Ser Gly Gly Gly Gly Ser
1               5                   10

<210> SEQ ID NO 19
<211> LENGTH: 10
<212> TYPE: PRT
<213> ORGANISM: artificial
<220> FEATURE:
<223> OTHER INFORMATION: synthetic linker

<400> SEQUENCE: 19

Gly Gly Gly Gly Ser Gly Gly Gly Gly Ser
1               5                   10

<210> SEQ ID NO 20
<211> LENGTH: 2
<212> TYPE: PRT
<213> ORGANISM: artificial
<220> FEATURE:
<223> OTHER INFORMATION: synthetic linker

<400> SEQUENCE: 20

Ser Asp
1

<210> SEQ ID NO 21
<211> LENGTH: 453
<212> TYPE: DNA
<213> ORGANISM: artificial
<220> FEATURE:
<223> OTHER INFORMATION: lipocalin mutein

<400> SEQUENCE: 21
gcctcagacg aggagattca ggatgtgtca gggacgtggt atctgaaggc catgacggtg      60 gattttttggt gttctgggat tcatgaggag tctgttacgc caatgactct gactaccctt     120
gaaggcggca atctggaggc taaggtcacc atggatattg agggatttct tcaagagttt     180
aaggcagtgt tagagaagac agatgaaccg ggtaaatata cggccgatgg cggtaaacat     240
gttgcctata tcattcgcag ccgtgtgaaa gatcattaca tctttttatag cgagggagat     300 tgtcctggtc cggttccagg ggtgtggctc gtgggcagag accccaagaa caacctggaa     360

```
gccttggagg actttgagaa agccgcagga gcccgcggac tcagcacgga gagcatcctc    420
atccccaggc agagcgaaac cagctctcca ggg                                 453

<210> SEQ ID NO 22
<211> LENGTH: 534
<212> TYPE: DNA
<213> ORGANISM: artificial
<220> FEATURE:
<223> OTHER INFORMATION: lipocalin mutein

<400> SEQUENCE: 22
caggactcca cctcagacct gatcccagcc ccacctctga gcaaggtccc tctgcagcag     60
aacttccagg acaaccaatt ccatgggaaa tggtatgtcg tgggcgaggc cggaaatctt    120
ttgctgcgtg aggataagga tccgaggaaa atgacggcga ccatttacga gttgaaagaa    180
gataaatcat atgacgtcac ccgggtggag tttggggcta agacatacaa gtaccagatt    240
ggaccctttg tgccggggag ccagccgggc gagtttactt taggcggtat tgaaagtatg    300
ccgggcatga tcatttttt ggtccgtgtc gtgagcacca actacaacca gcatgccata    360
gtgttcttca gtatgtgta tcagaaccgc gagtattttg agatcacact gtacgggcgc    420
acgaaagaac tgacaagcga gctgaaggaa aattttatcc gcttttccaa atctctgggc    480
ctccctgaaa accacatcgt cttccctgtc caatcgacca ggctatcga cggc           534

<210> SEQ ID NO 23
<211> LENGTH: 1053
<212> TYPE: DNA
<213> ORGANISM: artificial
<220> FEATURE:
<223> OTHER INFORMATION: fusion protein

<400> SEQUENCE: 23
gcctcagacg aggagattca ggatgtgtca gggacgtggt atctgaaggc catgacggtg     60 gattttggt gttctgggat tcatgaggag tctgttacgc caatgactct gactacccctt    120 gaaggcggca atctggaggc taaggtcacc atggatattg agggatttct tcaagagttt    180
aaggcagtgt tagagaagac agatgaaccg ggtaaatata cggccgatgg cggtaaacat    240
gttgcctata tcattcgcag ccgtgtgaaa gatcattaca tcttttatag cgagggagat    300
tgtcctggtc cggttccagg ggtgtggctc gtgggcagag accccaagaa caacctggaa    360
gccttggagg actttgagaa agccgcagga gcccgcggac tcagcacgga gagcatcctc    420
atccccaggc agagcgaaac cagctctcca gggagcgacg gtggtggtgg ttctggtggt    480
ggtggatcgc aggactccac ctcagacctg atcccagccc cacctctgag caaggtccct    540
ctgcagcaga acttccagga caaccaattc catgggaaat ggtatgtcgt gggcgaggcc    600
ggaaatcttt tgctgcgtga ggataaggat ccgaggaaaa tgacggcgac catttacgag    660
ttgaaagaag ataaatcata tgacgtcacc cgggtggagt ttggggctaa gacatacaag    720
taccagattg gaccctttgt gccggggagc cagccgggcg agtttacttt aggcggtatt    780
gaaagtatgc cgggcatgac atcatttttg gtccgtgtcg tgagcaccaa ctacaaccag    840
catgccatag tgttcttcaa gtatgtgtat cagaaccgcg agtattttga gatcacactg    900
tacgggcgca cgaaagaact gacaagcgag ctgaaggaaa attttatccg cttttccaaa    960
tctctgggcc tccctgaaaa ccacatcgtc ttccctgtcc aatcgaccag gctatcgac    1020 ggcagcgctt ggtctcaccc gcagttcgaa aaa                                1053
```

<210> SEQ ID NO 24
<211> LENGTH: 1047
<212> TYPE: DNA
<213> ORGANISM: artificial
<220> FEATURE:
<223> OTHER INFORMATION: fusion protein

<400> SEQUENCE: 24

```
caggactcca cctcagacct gatcccagcc ccacctctga gcaaggtccc tctgcagcag      60
aacttccagg acaaccaatt ccatgggaaa tggtatgtcg tgggcgaggc cggaaatctt     120
ttgctgcgtg aggataagga tccgaggaaa atgacggcga ccatttacga gttgaaagaa     180
gataaatcat atgacgtcac ccgggtggag tttggggcta agacatacaa gtaccagatt     240
gggacctttg tgccggggag ccagccgggc gagtttactt taggcggtat tgaaagtatg     300
ccgggcatga catcattttt ggtccgtgtc gtgagcacca actacaacca gcatgccata     360
gtgttcttca gtatgtgta tcagaaccgc gagtattttg agatcacact gtacgggcgc     420
acgaaagaac tgacaagcga gctgaaggaa aattttatcc gcttttccaa atctctgggc     480
ctccctgaaa accacatcgt cttccctgtc caatcgacc aggctatcga cggcggcggt     540
ggtggttctg gtggtggtgg atcggcctca gacgaggaga ttcaggatgt gtcagggacg     600
tggtatctga aggccatgac ggtggatttt tggtgttctg ggattcatga ggagtctgtt     660
acgccaatga ctctgactac ccttgaaggc ggcaatctgg aggctaaggt caccatggat     720
attgagggat tcttcaaga gtttaaggca gtgttagaga agacagatga accgggtaaa     780
tatacgccg atggcggtaa acatgttgcc tatatcattc gcagccgtgt gaaagatcat     840
tacatctttt atagcgaggg agattgtcct ggtccggttc caggggtgtg gctcgtgggc     900
agagacccca gaacaacct ggaagccttg gaggactttg agaaagccgc aggagccccgc     960
ggactcagca cggagagcat cctcatcccc aggcagagcg aaaccagctc tccagggagc    1020
gcttggtctc acccgcagtt cgaaaaa                                       1047
```

<210> SEQ ID NO 25
<211> LENGTH: 1218
<212> TYPE: DNA
<213> ORGANISM: artificial
<220> FEATURE:
<223> OTHER INFORMATION: fusion protein

<400> SEQUENCE: 25

```
gcctcagacg aggagattca ggatgtgtca gggacgtggt atctgaaggc catgacggtg      60
gattttggt gttctgggat tcatgaggag tctgttacgc caatgactct gactacccttt    120
gaaggcggca atctggaggc taaggtcacc atggatattg agggatttct tcaagagttt     180
aaggcagtgt tagagaagac agatgaaccg ggtaaatata cggccgatgg cggtaaacat     240
gttgcctata tcattcgcag ccgtgtgaaa gatcattaca tcttttatag cgagggagat     300
tgtcctggtc cggttccagg ggtgtggctc gtgggcagag accccaagaa caacctggaa     360
gccttggagg actttgagaa agccgcagga gcccgcggac tcagcacgga gagcatcctc     420
atccccaggc agagcgaaac cagctctcca gggagcgacg tggtggtgg ttctggtggt     480
ggtggatcgc aggactccac ctcagacctg atcccagccc cacctctgag caaggtccct     540
ctgcagcaga acttccagga caaccaattc catgggaaat ggtatgtcgt gggcgaggcc     600
ggaaatcttt tgctgcgtga ggataaggat ccgaggaaaa tgacggcgac catttacgag     660
ttgaaagaag ataaatcata tgacgtcacc cgggtggagt ttggggctaa gacatacaag     720
```

```
taccagattg ggacctttgt gccggggagc cagccgggcg agtttacttt aggcggtatt      780
gaaagtatgc cgggcatgac atcattttg gtccgtgtcg tgagcaccaa ctacaaccag       840
catgccatag tgttcttcaa gtatgtgtat cagaaccgcg agtattttga gatcacactg      900
tacgggcgca cgaaagaact gacaagcgag ctgaaggaaa attttatccg cttttccaaa      960
tctctgggcc tccctgaaaa ccacatcgtc ttccctgtcc aatcgacca ggctatcgac      1020 ggcagcgctg gtgccgtcga cgctaactct ctggctgaag ctaaagttct ggctaaccgt     1080
gaactggaca atacggtgt ttccgactac tacaaaaacc tcatcaacaa cgctaaaacc      1140
gttgaaggtg ttaaagctct gatcgacgaa attctcgcag cactgccgag cgcttggtct    1200
cacccgcagt tcgaaaaa                                                    1218
```

<210> SEQ ID NO 26
<211> LENGTH: 1671
<212> TYPE: DNA
<213> ORGANISM: artificial
<220> FEATURE:
<223> OTHER INFORMATION: fusion protein

<400> SEQUENCE: 26

```
gcaagtgatg aagaaattca ggatgttagc ggcacctggt atctgaaagc aatgaccgtt       60 gattttggt gcagcggtat tcatgaagaa agcgttaccc cgatgaccct gaccaccctg       120
gaaggtggta atctggaagc aaaagttacc atggatattg gggttttct gcaagaattt       180 aaagccgtgc tggaaaaaac cgatgaaccg ggtaaatata ccgcagatgg tggtaaacat      240
gtggcctata ttatccgtag ccgtgtgaaa gatcactata tcttttatag cgaaggtgat      300
tgtccgggtc cggttccggg tgtttggctg gttggtcgtg atccgaaaaa taacctggaa      360
gcactggaag attttgaaaa agcagccggt gcacgtggtc tgagcaccga aagcattctg      420
attccgcgtc agagcgaaac cagcagtcct ggatccgacg gtggtggtgg ttctggtggt      480
ggtggatcgg cctcagacga ggagattcag gatgtgtcag gacgtggta tctgaaggcc      540 atgacggtgg atttttggtg ttctgggatt catgaggagt ctgttacgcc aatgactctg      600
actacccttg aaggcggcaa tctggaggct aaggtcacca tggatattga gggattttctt      660 caagagttta aggcagtgtt agagaagaca gatgaaccgg gtaaatatac ggccgatggc      720
ggtaaacatg ttgcctatat cattcgcagc cgtgtgaaag atcattacat ctttatagc      780 gagggagatt gtcctggtcc ggttccaggg gtgtggctcg tgggcagaga ccccaagaac     840
aacctggaag ccttggagga ctttgagaaa gccgcaggag cccgcggact cagcacggag     900
agcatcctca tccccaggca gagcgaaacc agctctccag ggagcgacgg cggaggtggc    960
tcaggaggtg gcggatccca ggactccacc tcagacctga tcccagcccc acctctgagc    1020
aaggtccctc tgcagcagaa cttccaggac aaccaattcc atgggaaatg gtatgtcgtg    1080
ggcgaggccg gaaatctttt gctgcgtgag gataaggatc cgaggaaaat gacggcgacc   1140
atttacgagt tgaaagaaga taatcatat gacgtcaccc gggtggagtt tgggctaag     1200 acatacaagt accagattgg gacctttgtg ccggggagcc agccgggcga gtttacttta   1260
ggcggtattg aaagtatgcc gggcatgaca tcattttgg tccgtgtcgt gagcaccaac    1320
tacaaccagc atgccatagt gttcttcaag tatgtgtatc agaaccgcga gtattttgag   1380
atcacactgt acgggcgcac gaaagaactg acaagcgagc tgaaggaaaa ttttatccgc   1440
ttttccaaat ctctgggcct ccctgaaaac cacatcgtct tccctgtccc aatcgaccag   1500
gctatcgacg gcagcggcgg cggcggctct ctggctgaag ctaaagaagc ggctaacgcg   1560
```

<210> SEQ ID NO 27
<211> LENGTH: 720
<212> TYPE: DNA
<213> ORGANISM: artificial
<220> FEATURE:
<223> OTHER INFORMATION: fusion protein

<400> SEQUENCE: 27

```
caggactcca cctcagacct gatcccagcc ccacctctga gcaaggtccc tctgcagcag    60
aacttccagg acaaccaatt ccatgggaaa tggtatgtcg tgggcgaggc cggaaatctt   120
ttgctgcgtg aggataagga tccgaggaaa atgacggcga ccatttacga gttgaaagaa   180
gataaatcat atgacgtcac ccgggtggag tttggggcta agcatacaa gtaccagatt   240
gggacctttg tgccggggag ccagccgggc gagtttactt taggcggtat tgaaagtatg   300
ccgggcatga catcattttt ggtccgtgtc gtgagcacca actacaacca gcatgccata   360
gtgttcttca gtatgtgta tcagaaccgc gagtattttg agatcacact gtacgggcgc   420
acgaaagaac tgacaagcga gctgaaggaa aattttatcc gcttttccaa atctctgggc   480
ctccctgaaa accacatcgt cttccctgtc caatcgacc aggctatcga cggcagcggc   540
ggcggcggct ctctggctga agctaagaa gcggctaacg cggaactgga ctcttacggt   600
gtttccgact tttacaaacg tctcatcgat aaagctaaaa ccgttgaagg tgttgaagct   660
ctgaaagacg cgattctcgc agcactgccg agcgcttggt ctcacccgca gttcgaaaaa   720
```

<210> SEQ ID NO 28
<211> LENGTH: 645
<212> TYPE: DNA
<213> ORGANISM: artificial
<220> FEATURE:
<223> OTHER INFORMATION: fusion protein

<400> SEQUENCE: 28

```
gcctcagacg aggagattca ggatgtgtca gggacgtggt atctgaaggc catgacggtg    60
gatttttggt gttctgggat tcatgaggag tctgttacgc caatgactct gactacccct   120
gaaggcggca atctggaggc taaggtcacc atggatattg agggatttct tcaagagttt   180
aaggcagtgt tagagaagac agatgaaccg ggtaaatata cggccgatgg cggtaaacat   240
gttgcctata tcattcgcag ccgtgtgaaa gatcattaca tcttttatag cgagggagat   300
tgtcctggtc cggttccagg ggtgtggctc gtgggcagag accccaagaa caacctggaa   360
gccttggagg actttgagaa agccgcagga gcccgcggac tcagcacgga gagcatcctc   420
atccccaggc agagcgaaac cagctctcca gggagcgata gcggcggcgg cggctctctg   480
gctgaagcta agaagcggc taacgcggaa ctggactctt acggtgtttc cgactttac   540
aaacgtctca tcgataaagc taaaaccgtt gaaggtgttg aagctctgaa agacgcgatt   600
ctcgcagcac tgccgagcgc ttggtctcac ccgcagttcg aaaaa                   645
```

<210> SEQ ID NO 29
<211> LENGTH: 1209
<212> TYPE: DNA
<213> ORGANISM: artificial
<220> FEATURE:
<223> OTHER INFORMATION: fusion protein

<400> SEQUENCE: 29

```
gcctcagacg aggagattca ggatgtgtca gggacgtggt atctgaaggc catgacggtg      60
gattttggt gttctgggat tcatgaggag tctgttacgc caatgactct gactacccctt    120
gaaggcggca atctggaggc taaggtcacc atggatattg agggatttct tcaagagttt    180
aaggcagtgt tagagaagac agatgaaccg ggtaaatata cggccgatgg cggtaaacat    240
gttgcctata tcattcgcag ccgtgtgaaa gatcattaca tcttttatag cgagggagat    300
tgtcctggtc cggttccagg ggtgtggctc gtgggcagag accccaagaa caacctggaa    360
gccttggagg actttgagaa agccgcagga gcccgcggac tcagcacgga gagcatcctc    420
atccccaggc agagcgaaac cagctctcca gggagcgacg gcggaggtgg ctcaggaggt    480
ggcggatccc aggactccac ctcagacctg atcccagccc cacctctgag caaggtccct    540
ctgcagcaga acttccagga caaccaattc catgggaaat ggtatgtcgt gggcgaggcc    600
ggaaatcttt tgctgcgtga ggataaggat ccgaggaaaa tgacggcgac catttacgag    660
ttgaaagaag ataaatcata tgacgtcacc cgggtggagt ttggggctaa gacatacaag    720
taccagattg ggacctttgt gccggggagc cagccgggcg agtttacttt aggcggtatt    780
gaaagtatgc cgggcatgac atcatttttg gtccgtgtcg tgagcaccaa ctacaaccag    840
catgccatag tgttcttcaa gtatgtgtat cagaaccgcg agtatttga gatcacactg    900
tacgggcgca cgaaagaact gacaagcgag ctgaaggaaa attttatccg cttttccaaa    960
tctctgggcc tccctgaaaa ccacatcgtc ttccctgtcc caatcgacca ggctatcgac   1020
ggcagcggcg gcggcggctc tctggctgaa gctaaagaag cggctaacgc ggaactggac   1080
tcttacggtg tttccgactt ttacaaacgt ctcatcgata aagctaaaac cgttgaaggt   1140
gttgaagctc tgaaagacgc gattctcgca gcactgccga gcgcttggtc tcacccgcag   1200
ttcgaaaaa                                                           1209
```

<210> SEQ ID NO 30
<211> LENGTH: 1134
<212> TYPE: DNA
<213> ORGANISM: artificial
<220> FEATURE:
<223> OTHER INFORMATION: fusion protein

<400> SEQUENCE: 30

```
gcaagtgatg aagaaattca ggatgttagc ggcacctggt atctgaaagc aatgaccgtt      60
gattttggt gcagcggtat tcatgaagaa agcgttaccc cgatgaccct gaccacccctg    120
gaaggtggta atctggaagc aaaagttacc atggatattg agggttttct gcaagaattt    180
aaagccgtgc tggaaaaaac cgatgaaccg ggtaaatata ccgcagatgg tggtaaacat    240
gtggcctata ttatccgtag ccgtgtgaaa gatcactata tcttttatag cgaaggtgat    300
tgtccgggtc cggttccggg tgtttggctg gttggtcgtg atccgaaaaa taacctggaa    360
gcactggaag attttgaaaa agcagccggt gcacgtggtc tgagcaccga aagcattctg    420
attccgcgtc agagcgaaac cagcagtcct ggatccgacg gtggtggtgg ttctggtggt    480
ggtggatcgg cctcagacga ggagattcag gatgtgtcag ggacgtggta tctgaaggcc    540
atgacggtgg attttggtg ttctgggatt catgaggagt ctgttacgcc aatgactctg    600
actacccttg aaggcggcaa tctggaggct aaggtcacca tggatattga gggatttctt    660
caagagttta aggcagtgtt agagaagaca gatgaaccgg gtaaatatac ggccgatggc    720
ggtaaacatg ttgcctatat cattcgcagc cgtgtgaaag atcattacat ctttatagc    780
```

| | |
|---|---:|
| gagggagatt gtcctggtcc ggttccaggg gtgtggctcg tgggcagaga ccccaagaac | 840 |
| aacctggaag ccttggagga ctttgagaaa gccgcaggag cccgcggact cagcacggag | 900 |
| agcatcctca tccccaggca gagcgaaacc agctctccag ggagcgatag cggcggcggc | 960 |
| ggctctctgg ctgaagctaa agaagcggct aacgcggaac tggactctta cggtgtttcc | 1020 |
| gacttttaca acgtctcat cgataaagct aaaaccgttg aaggtgttga agctctgaaa | 1080 |
| gacgcgattc tcgcagcact gccgagcgct tggtctcacc cgcagttcga aaaa | 1134 |

```
<210> SEQ ID NO 31
<211> LENGTH: 1173
<212> TYPE: DNA
<213> ORGANISM: artificial
<220> FEATURE:
<223> OTHER INFORMATION: fusion protein

<400> SEQUENCE: 31
```

| | |
|---|---:|
| gacaaaaccc acacctgccc accttgtcct gcccctgaac tgctgggagg accttctgtg | 60 |
| tttctgttcc caccaaaacc aaaagatacc ctgatgatct ctagaacccc tgaggtgaca | 120 |
| tgtgtggtgg tggatgtgtc tcatgaggac cctgaggtca aattcaactg gtacgtggat | 180 |
| ggagtggaag tccacaatgc caaaaccaag cctagagagg aacagtacaa ttcaacctac | 240 |
| agagtggtca gtgtgctgac tgtgctgcat caggattggc tgaatggcaa ggaatacaag | 300 |
| tgtaaagtct caaacaaggc cctgcctgct ccaattgaga aaacaatctc aaaggccaag | 360 |
| ggacagccta gggaaccca ggtctacacc ctgccacctt caagagagga atgaccaaa | 420 |
| aaccaggtgt ccctgacatg cctggtcaaa ggcttctacc cttctgacat tgctgtggag | 480 |
| tgggagtcaa atggacagcc tgagaacaac tacaaaacaa ccccccctgt gctggattct | 540 |
| gatggctctt tctttctgta ctccaaactg actgtggaca gtctagatg cagcagggg | 600 |
| aatgtctttt cttgctctgt catgcatgag gctctgcata accactacac tcagaaatcc | 660 |
| ctgtctctgt ctcctggcaa aggcggcgga ggatccggcg aggaggtag cgcatcagac | 720 |
| gaggaaatcc aggacgtgtc agggacctgg tacctgaaag ccatgaccgt ggatttttgg | 780 |
| tgctccggca tccatgagga gtcagtcact cccatgaccc tgacaaccct agaaggtggg | 840 |
| aatctggagg ccaaagtgac aatggatatt gagggctttc tccaggagtt caagccgtc | 900 |
| ctcgagaaga cagacgagcc tggaaagtat actgctgatg ggggaaaaca cgtagcctat | 960 |
| atcattcgat ctcgggtgaa ggatcattat atcttctatt ccgagggcga ctgccccggc | 1020 |
| cctgtgccag gtgtctggct agttgggagg gaccccaaga acaatctcga ggctctggag | 1080 |
| gacttcgaga aggcagctgg tgccagggga ttgagcactg agtctatcct tatcccacgc | 1140 |
| cagagcgaga cctcaagccc agggtccgac tga | 1173 |

```
<210> SEQ ID NO 32
<211> LENGTH: 1659
<212> TYPE: DNA
<213> ORGANISM: artificial
<220> FEATURE:
<223> OTHER INFORMATION: fusion protein

<400> SEQUENCE: 32
```

| | |
|---|---:|
| gcatcagacg aggaaatcca ggacgtgtca gggacctggt acctgaaagc catgaccgtg | 60 |
| gattttttggt gctccggcat ccatgaggag tcagtcactc ccatgaccct gacaacccta | 120 |
| gaaggtggga atctggaggc caaagtgaca atggatattg agggctttct ccaggagttc | 180 |
| aagccgtcc tcgagaagac agacgagcct ggaaagtata ctgctgatgg gggaaaacac | 240 |

```
gtagcctata tcattcgatc tcgggtgaag gatcattata tcttctattc cgagggcgac    300
tgccccggcc ctgtgccagg tgtctggcta gttgggaggg accccaagaa caatctcgag    360
gctctggagg acttcgagaa ggcagctggt gccaggggat tgagcactga gtctatcctt    420
atcccacgcc agagcgagac ctcaagccca gggtccgacg gcggtggagg atccggtgga    480
ggcggttctg acaaaaccca cacctgccca ccttgtcctg cccctgaact gctgggagga    540
ccttctgtgt ttctgttccc accaaaacca aaagataccc tgatgatctc tagaaccccr    600
gaggtgacat gtgtggtggt ggatgtgtct catgaggacc ctgaggtcaa attcaactgg    660
tacgtggatg gagtggaagt ccacaatgcc aaaaccaagc ctagagagga acagtacaat    720
tcaacctaca gagtggtcag tgtgctgact gtgctgcatc aggattggct gaatggcaag    780
gaatacaagt gtaaagtctc aaacaaggcc ctgcctgctc caattgagaa aacaatctca    840
aaggccaagg gacagcctag ggaaccccag gtctacaccc tgccaccttc aagagaggaa    900
atgaccaaaa accaggtgtc cctgacatgc ctggtcaaag gcttctaccc ttctgacatt    960
gctgtggagt gggagtcaaa tggacagcct gagaacaact acaaaacaac cccccctgtg   1020
ctggattctg atggctcttt cttttctgta ctccaaactg actgtggaca gtctagatgg   1080
cagcagggga atgtcttttc ttgctctgtc atgcatgagg ctctgcataa ccactacact   1140
cagaaatccc tgtctctgtc tcccgggaaa ggggtgggg gatccggcgg aggaggtagc   1200
gcatcagacg aggaaatcca ggacgtgtca gggacctggt acctgaaagc catgaccgtg   1260
gatttttggt gctccggcat ccatgaggag tcagtcactc ccatgaccct gacaacccta   1320
gaaggtggga atctggaggc caaagtgaca atggatattg agggctttct ccaggagttc   1380
aaagccgtcc tcgagaagac agacgagcct ggaaagtata ctgctgatgg gggaaaacac   1440
gtagcctata tcattcgatc tcgggtgaag gatcattata tcttctattc cgagggcgac   1500
tgccccggcc ctgtgccagg tgtctggcta gttgggaggg accccaagaa caatctcgag   1560
gctctggagg acttcgagaa ggcagctggt gccaggggat tgagcactga gtctatcctt   1620
atcccacgcc agagcgagac ctcaagccca gggtccgac                          1659

<210> SEQ ID NO 33
<211> LENGTH: 1659
<212> TYPE: DNA
<213> ORGANISM: artificial
<220> FEATURE:
<223> OTHER INFORMATION: fusion protein

<400> SEQUENCE: 33
gacaaaaccc acacctgccc accttgtcct gcccctgaac tgctgggagg accttctgtg     60
tttctgttcc caccaaaacc aaaagatacc ctgatgatct ctagaacccc tgaggtgaca   120
tgtgtggtgg tggatgtgtc tcatgaggac cctgaggtca aattcaactg gtacgtggat   180
ggagtggaag tccacaatgc caaaaccaag cctagagagg aacagtacaa ttcaacctac   240
agagtggtca gtgtgctgac tgtgctgcat caggattggc tgaatggcaa ggaatacaag   300
tgtaaagtct caaacaaggc cctgcctgct ccaattgaga aacaatctc aaaggccaag   360 ggacagccta gggaacccca ggtctacacc ctgccacctt caagagagga atgaccaaa   420 aaccaggtgt ccctgacatg cctggtcaaa ggcttctacc cttctgacat tgctgtggag   480
tgggagtcaa atggacagcc tgagaacaac tacaaaacaa ccccccctgt gctggattct   540
gatggctctt tcttttctgta ctccaaactg actgtggaca gtctagatg gcagcagggg   600 aatgtctttt cttgctctgt catgcatgag gctctgcata accactacac tcagaaatcc   660
```

```
ctgtctctgt ctcctggcaa aggcggcgga ggatccggcg gaggaggtag cgcatcagac    720
gaggaaatcc aggacgtgtc agggacctgg tacctgaaag ccatgaccgt ggattttgg    780 tgctccggca tccatgagga gtcagtcact cccatgaccc tgacaaccct agaaggtggg    840
aatctggagg ccaaagtgac aatggatatt gagggctttc tccaggagtt caaagccgtc    900
ctcgagaaga cagacgagcc tggaaagtat actgctgatg ggggaaaaca cgtagcctat    960
atcattcgat ctcgggtgaa ggatcattat atcttctatt ccgagggcga ctgccccggc   1020
cctgtgccag gtgtctggct agttgggagg accccaaga acaatctcga ggctctggag   1080
gacttcgaga aggcagctgg tgccagggga ttgagcactg agtctatcct tatcccacgc   1140
cagagcgaga cctcaagccc agggtccgac ggcggcggtg ggtccggcgg cggtggctcc   1200
gcgtccgatg aagaaatcca ggatgtgagc ggcacctggt atctgaaagc aatgaccgtt   1260
gacttctggt gctccggcat ccatgaagaa agcgtgaccc caatgacctt gaccacgctg   1320
gaaggcggta atttagaagc caaagtaact atggatatcg aaggcttcct gcaggaattt   1380
aaagcggtgc tgaaaaaac tgatgagcca ggtaaataca ccgccgacgg tggcaaacac   1440
gtggcctata ttatccgttc tcgtgtcaaa gaccattata tcttctactc tgaaggcgat   1500
tgccccggtc cggttccggg cgtctggctt gtcggtcgtg acccgaaaaa caacctggaa   1560
gcactcgaag acttcgaaaa agcggcaggc gcgcgtggtc tgtctaccga gagcatcctt   1620
atcccacgtc agagcgaaac ctccagccct ggttccgat                        1659
```

<210> SEQ ID NO 34
<211> LENGTH: 165
<212> TYPE: DNA
<213> ORGANISM: artificial
<220> FEATURE:
<223> OTHER INFORMATION: albumin binding domain

<400> SEQUENCE: 34

```
agcgctggtg ccgtcgacgc taactctctg gctgaagcta agttctggc taaccgtgaa     60 ctggacaaat acggtgtttc cgactactac aaaaaacctca tcaacaacgc taaaaccgtt    120
gaaggtgtta agctctgat cgacgaaatt ctcgcagcac tgccg                     165
```

<210> SEQ ID NO 35
<211> LENGTH: 156
<212> TYPE: DNA
<213> ORGANISM: artificial
<220> FEATURE:
<223> OTHER INFORMATION: albumin binding domain

<400> SEQUENCE: 35

```
agcggcggcg gcggctctct ggctgaagct aaagaagcgg ctaacgcgga actggactct     60
tacggtgttt ccgacttta caaacgtctc atcgataaag ctaaaaccgt tgaaggtgtt    120
gaagctctga agacgcgat tctcgcagca ctgccg                              156
```

<210> SEQ ID NO 36
<211> LENGTH: 681
<212> TYPE: DNA
<213> ORGANISM: artificial
<220> FEATURE:
<223> OTHER INFORMATION: Fc portion

<400> SEQUENCE: 36

```
gacaaaaccc acacctgccc cacccttgtcct gcccctgaac tgctgggagg accttctgtg     60
tttctgttcc caccaaaaacc aaaagatacc ctgatgatct ctagaacccc tgaggtgaca    120
```

```
tgtgtggtgg tggatgtgtc tcatgaggac cctgaggtca aattcaactg gtacgtggat      180
ggagtggaag tccacaatgc caaaaccaag cctagagagg aacagtacaa ttcaacctac      240
agagtggtca gtgtgctgac tgtgctgcat caggattggc tgaatggcaa ggaatacaag      300
tgtaaagtct caaacaaggc cctgcctgct ccaattgaga aacaatctc aaaggccaag       360 ggacagccta gggaacccca ggtctacacc ctgccacctt caagagagga atgaccaaa       420 aaccaggtgt ccctgacatg cctggtcaaa ggcttctacc cttctgacat tgctgtggag     480
tgggagtcaa atggacagcc tgagaacaac tacaaaacaa ccccccctgt gctggattct     540
gatggctctt tctttctgta ctccaaactg actgtggaca gtctagatg gcagcagggg     600 aatgtctttt cttgctctgt catgcatgag gctctgcata accactacac tcagaaatcc     660
ctgtctctgt ctcctggcaa g                                                681

<210> SEQ ID NO 37
<211> LENGTH: 30
<212> TYPE: DNA
<213> ORGANISM: artificial
<220> FEATURE:
<223> OTHER INFORMATION: protein tag

<400> SEQUENCE: 37
agcgcttggt ctcacccgca gttcgaaaaa                                        30

<210> SEQ ID NO 38
<211> LENGTH: 36
<212> TYPE: DNA
<213> ORGANISM: artificial
<220> FEATURE:
<223> OTHER INFORMATION: synthetic linker

<400> SEQUENCE: 38
agcgacggtg gtggtggttc tggtggtggt ggatcg                                 36

<210> SEQ ID NO 39
<211> LENGTH: 30
<212> TYPE: DNA
<213> ORGANISM: artificial
<220> FEATURE:
<223> OTHER INFORMATION: synthetic linker

<400> SEQUENCE: 39
ggtggtggtg gttctggtgg tggtggatcg                                        30

<210> SEQ ID NO 40
<211> LENGTH: 6
<212> TYPE: DNA
<213> ORGANISM: artificial
<220> FEATURE:
<223> OTHER INFORMATION: synthetic linker

<400> SEQUENCE: 40 agcgac                                                                   6

<210> SEQ ID NO 41
<211> LENGTH: 158
<212> TYPE: PRT
<213> ORGANISM: human
```

<400> SEQUENCE: 41

His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
            20                  25                  30

Leu Glu Ser Val Thr Pro Met Thr Leu Thr Thr Leu Glu Gly Gly Asn
        35                  40                  45

Leu Glu Ala Lys Val Thr Met Leu Ile Ser Gly Arg Cys Gln Glu Val
    50                  55                  60

Lys Ala Val Leu Glu Lys Thr Asp Glu Pro Gly Lys Tyr Thr Ala Asp
65                  70                  75                  80

Gly Gly Lys His Val Ala Tyr Ile Ile Arg Ser His Val Lys Asp His
                85                  90                  95

Tyr Ile Phe Tyr Cys Glu Gly Glu Leu His Gly Lys Pro Val Arg Gly
            100                 105                 110

Val Lys Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155

<210> SEQ ID NO 42
<211> LENGTH: 151
<212> TYPE: PRT
<213> ORGANISM: artificial
<220> FEATURE:
<223> OTHER INFORMATION: lipocalin mutein

<400> SEQUENCE: 42

Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Leu Glu Gly Gly Asn Leu Glu Ala Lys
        35                  40                  45

Val Thr Met Asp Ile Glu Gly Phe Leu Gln Glu Phe Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Asp Cys Pro Gly Pro Val Pro Gly Val Trp Leu Val Gly
            100                 105                 110

Arg Asp Pro Lys Asn Asn Leu Glu Ala Leu Glu Asp Phe Glu Lys Ala
        115                 120                 125

Ala Gly Ala Arg Gly Leu Ser Thr Glu Ser Ile Leu Ile Pro Arg Gln
    130                 135                 140

Ser Glu Thr Ser Ser Pro Gly
145                 150

<210> SEQ ID NO 43
<211> LENGTH: 178
<212> TYPE: PRT
<213> ORGANISM: human

```
<400> SEQUENCE: 43

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 44
<211> LENGTH: 178
<212> TYPE: PRT
<213> ORGANISM: artificial
<220> FEATURE:
<223> OTHER INFORMATION: lipocalin mutein

<400> SEQUENCE: 44

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Leu Leu Arg Glu Asp Lys Asp Pro
        35                  40                  45

Arg Lys Met Thr Ala Thr Ile Tyr Glu Leu Lys Glu Asp Lys Ser Tyr
    50                  55                  60

Asn Val Thr Arg Val Glu Phe Gly Val Lys Thr Tyr Lys Tyr Gln Ile
65                  70                  75                  80

Gly Thr Phe Val Pro Gly Ser Gln Pro Gly Glu Phe Thr Leu Gly Gly
                85                  90                  95

Ile Lys Ser Met Pro Gly Met Thr Ser Phe Leu Val Arg Val Val Ser
            100                 105                 110

Thr Asn Tyr Asn Gln His Ala Met Val Phe Phe Lys Tyr Val Tyr Gln
        115                 120                 125

Asn Arg Glu Tyr Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160
```

Leu Pro Glu Asn His Ile Val Phe Pro Val Pro Ile Asp Gln Ala Ile
            165                 170                 175

Asp Gly

<210> SEQ ID NO 45
<211> LENGTH: 178
<212> TYPE: PRT
<213> ORGANISM: artificial
<220> FEATURE:
<223> OTHER INFORMATION: lipocalin mutein

<400> SEQUENCE: 45

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Ile Leu Arg Glu Asp Lys Asp Pro
        35                  40                  45

Arg Lys Met Thr Ala Thr Ile Tyr Glu Leu Lys Glu Asp Lys Ser Tyr
50                  55                  60

Asp Val Thr Arg Val Glu Phe Gly Val Lys Thr Arg Lys Tyr Arg Ile
65                  70                  75                  80

Gly Thr Phe Val Pro Gly Ser Gln Pro Gly Glu Phe Thr Leu Gly Gly
                85                  90                  95

Ile Lys Ser Met Pro Gly Met Thr Ser Phe Leu Val Arg Val Val Ser
            100                 105                 110

Thr Asn Tyr Asn Gln His Ala Met Val Phe Phe Lys Tyr Val Tyr Gln
        115                 120                 125

Asn Arg Glu Tyr Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ala Ile
                165                 170                 175

Asp Gly

<210> SEQ ID NO 46
<211> LENGTH: 178
<212> TYPE: PRT
<213> ORGANISM: artificial
<220> FEATURE:
<223> OTHER INFORMATION: lipocalin mutein

<400> SEQUENCE: 46

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Leu Leu Arg Glu Asp Lys Asp Pro
        35                  40                  45

Arg Lys Met Thr Ala Thr Ile Tyr Glu Leu Arg Glu Asp Lys Ser Tyr
50                  55                  60

Asp Val Thr Arg Val Glu Phe Gly Val Lys Thr Tyr Lys Tyr Gln Ile
65                  70                  75                  80

Gly Thr Phe Val Pro Gly Ser Gln Pro Gly Glu Phe Thr Leu Gly Gly
                85                  90                  95

Ile Lys Ser Met Pro Gly Met Thr Ser Phe Leu Val Arg Val Val Ser
            100                 105                 110

Thr Asp Tyr Asn Gln His Ala Met Val Phe Phe Lys Tyr Val Tyr Gln
        115                 120                 125

Asn Arg Glu Tyr Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ala Ile
                165                 170                 175

Asp Gly

<210> SEQ ID NO 47
<211> LENGTH: 456
<212> TYPE: DNA
<213> ORGANISM: human

<400> SEQUENCE: 47
gcctcagacg aggagattca ggatgtgtca gggacgtggt atctgaaggc catgacggtg      60
gacagggagt tccctgagat gaatctggaa tcggtgacac ccatgaccct cacgaccctg     120 gaaggggggca acctggaagc caaggtcacc atgctgataa gtggccggtg ccaggaggtg    180
aaggccgtcc tggagaaaac tgacgagccg ggaaaataca cggccgacgg ggcaagcac     240 gtggcataca tcatcaggtc gcacgtgaag gaccactaca tcttttactg tgagggcgag    300
ctgcacggga gccggtccg aggggtgaag ctcgtgggca gagacccaaa gaacaacctg     360
gaagccttgg aggactttga gaaagccgca ggagcccgcg gactcagcac ggagagcatc    420
ctcatcccca ggcagagcga aacctgctct ccaggg                              456

<210> SEQ ID NO 48
<211> LENGTH: 453
<212> TYPE: DNA
<213> ORGANISM: artificial
<220> FEATURE:
<223> OTHER INFORMATION: lipocalin mutein

<400> SEQUENCE: 48
gcctcagacg aggagattca ggatgtgtca gggacgtggt atctgaaggc catgacggtg      60 gattttggt gttctgggat tcatgaggag tctgttacgc caatgactct gactacccttt     120 gaaggcggca atctggaggc taaggtcacc atggatattg agggatttct tcaagagttt    180
aaggcagtgt tagagaagac agatgaaccg gtaaatata cggccgatgg cggtaaacat    240
gttgcctata tcattcgcag ccatgtgaaa gatcattaca tcttttatag cgagggagat    300
tgtcctggtc cggttccagg ggtgtggctc gtgggcagag accccaagaa caacctggaa   360
gccttggagg actttgagaa agccgcagga gcccgcggac tcagcacgga gcatcctc     420 atccccaggc agagcgaaac cagctctcca ggg                                 453

<210> SEQ ID NO 49
<211> LENGTH: 534
<212> TYPE: DNA
<213> ORGANISM: human

<400> SEQUENCE: 49
caggactcca cctcagacct gatcccagcc ccacctctga gcaaggtccc tctgcagcag      60
aacttccagg acaaccaatt ccaggggaag tggtatgtgg taggcctggc agggaatgca    120

```
attctcagag aagacaaaga cccgcaaaag atgtatgcca ccatctatga gctgaaagaa    180
gacaagagct acaatgtcac ctccgtcctg tttaggaaaa agaagtgtga ctactggatc    240 aggactttg ttccaggttg ccagcccggc gagttcacgc tgggcaacat taagagttac     300
cctggattaa cgagttacct cgtccgagtg gtgagcacca actacaacca gcatgctatg    360
gtgttcttta agaaagtttc tcaaaacagg gagtacttca agatcaccct ctacgggaga    420
accaaggagc tgacttcgga actaaaggag aacttcatcc gcttctccaa atctctgggc    480
ctccctgaaa accacatcgt cttccctgtc ccaatcgacc agtgtatcga cggc          534
```

<210> SEQ ID NO 50
<211> LENGTH: 534
<212> TYPE: DNA
<213> ORGANISM: artificial
<220> FEATURE:
<223> OTHER INFORMATION: lipocalin mutein

<400> SEQUENCE: 50

```
caggactcca cctcagacct gatcccagcc ccacctctga gcaaggtccc tctgcagcag     60
aacttccagg acaaccaatt ccatgggaaa tggtatgtcg tgggcgaggc cggaaatctt    120
ttgctgcgtg aggataagga tccgaggaaa atgacggcga ccatttacga gttgaaagaa    180
gataaatcat ataacgtcac ccgggtggag tttggggtta agacatacaa gtaccagatt    240
gggacctttg tgccggggag ccagccgggc gagtttactt taggcggtat taaaagtatg    300
ccgggcatga catcattttt ggtccgcgtc gtgagcacca actacaacca gcatgccatg    360
gtgttcttca gtatgtgta tcagaaccgc gagtattttg agatcacact gtacgggcgc     420
acgaaagaac tgacaagcga gctgaaggaa aattttatcc gcttttccaa atctctgggc    480
ctccctgaaa accacatcgt cttccctgtc ccaatcgacc aggctatcga cggc          534
```

<210> SEQ ID NO 51
<211> LENGTH: 534
<212> TYPE: DNA
<213> ORGANISM: artificial
<220> FEATURE:
<223> OTHER INFORMATION: lipocalin mutein

<400> SEQUENCE: 51

```
caggactcca cctcagacct gatcccagcc ccacctctga gcaaggtccc tctgcagcag     60
aacttccagg acaaccaatt ccatgggaaa tggtacgtag taggtgaggc cggaaatctg    120
attctgcgtg aggataagga tccgagaaaa atgactgcga ccatttacga gttgaaagaa    180
gataaatcat atgacgtcac cagggtggag tttggggtga agacgcgtaa gtaccggatt    240
gggacctttg tgccggggag ccagccgggc gagtttactt taggcggtat taaaagtatg    300
ccgggcatga catcattttt ggtccgcgtc gtgagcacca actacaacca gcatgccatg    360
gtgttcttca gtacgtgta tcagaaccgc gagtattttg agatcacact gtacgggcgc     420
acgaaagaac tgacaagcga gctgaaggaa aattttatcc gcttttccaa atctctgggc    480
ctccctgaaa accacatcgt cttccctgtc ccaatcgacc aggctatcga cggc          534
```

<210> SEQ ID NO 52
<211> LENGTH: 534
<212> TYPE: DNA
<213> ORGANISM: artificial
<220> FEATURE:
<223> OTHER INFORMATION: lipocalin mutein

<400> SEQUENCE: 52

```
caggactcca cctcagacct gatcccagcc ccacctctga gcaaggtccc tctgcagcag      60
aacttccagg acaaccaatt ccatgggaaa tggtatgtcg tgggcgaggc cggaaatctt     120
ttgctgcgtg aggataagga tccgaggaaa atgacggcga ccatttacga gttgagagaa     180
gataaatcat atgacgtcac ccgggtggag tttggggtta agacatacaa gtaccagatt     240
gggacctttg tgccggggag ccagccgggc gagtttactt taggcggtat taaaagtatg     300
ccgggcatga catcattttt ggtccgcgtc gtgagcaccg actacaacca gcatgccatg     360
gtgttcttca gtatgtgta tcagaaccgc gagtattttg agatcacact gtacgggcgc     420
acgaaagaac tgacaagcga gttgaaggaa aattttatcc gcttttccaa atctctgggc     480
ctccctgaaa accacatcgt cttccctgtc ccaatcgacc aggctatcga cggc           534
```

<210> SEQ ID NO 53
<211> LENGTH: 457
<212> TYPE: PRT
<213> ORGANISM: artificial
<220> FEATURE:
<223> OTHER INFORMATION: reference antibody heavy chain

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255
```

```
Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 54
<211> LENGTH: 215
<212> TYPE: PRT
<213> ORGANISM: artificial
<220> FEATURE:
<223> OTHER INFORMATION: reference antibody light chain

<400> SEQUENCE: 54

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 55
<211> LENGTH: 446
<212> TYPE: PRT
<213> ORGANISM: artificial
<220> FEATURE:
<223> OTHER INFORMATION: reference antibody heavy chain

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile Ser Trp Val Arg Gln Ala Pro Gly Gln Gly Leu Glu Trp Met
        35                  40                  45

Gly Val Ile Asn Pro Glu Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300
```

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
                435                 440                 445

<210> SEQ ID NO 56
<211> LENGTH: 219
<212> TYPE: PRT
<213> ORGANISM: artificial
<220> FEATURE:
<223> OTHER INFORMATION: reference antibody light chain

<400> SEQUENCE: 56

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Lys His Ser
            20                  25                  30

Arg Gly Asn Thr Phe Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 57
<211> LENGTH: 449
<212> TYPE: PRT
<213> ORGANISM: artificial
<220> FEATURE:
<223> OTHER INFORMATION: reference antibody heavy chain

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Val Ser Gly Lys Thr Phe Trp Ser Tyr
            20                  25                  30

Gly Ile Asn Trp Val Arg Gln Ala Pro Gly Lys Gly Leu Glu Trp Met
        35                  40                  45

Gly Tyr Ile Tyr Ile Gly Thr Gly Tyr Thr Glu Pro Asn Pro Lys Tyr
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ile Gly Gly Tyr Tyr Gly Asn Phe Asp Gln Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 58
<211> LENGTH: 219
<212> TYPE: PRT
<213> ORGANISM: artificial
<220> FEATURE:
<223> OTHER INFORMATION: reference antibody light chain

<400> SEQUENCE: 58

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Ile Ser
            20                  25                  30

Gly Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Gln Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Tyr Phe Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 59
<211> LENGTH: 447
<212> TYPE: PRT
<213> ORGANISM: artificial
<220> FEATURE:
<223> OTHER INFORMATION: reference antibody heavy chain
```

<400> SEQUENCE: 59

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Asp Pro Ser Asn Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

-continued

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 60
<211> LENGTH: 217
<212> TYPE: PRT
<213> ORGANISM: artificial
<220> FEATURE:
<223> OTHER INFORMATION: reference antibody light chain

<400> SEQUENCE: 60

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Trp Thr Asp Gly
                85                  90                  95

Leu Ser Leu Val Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 61
<211> LENGTH: 451
<212> TYPE: PRT
<213> ORGANISM: artificial
<220> FEATURE:
<223> OTHER INFORMATION: benchmark antibody heavy chain

<400> SEQUENCE: 61

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

```
Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 62
<211> LENGTH: 214
<212> TYPE: PRT
<213> ORGANISM: artificial
<220> FEATURE:
<223> OTHER INFORMATION: benchmark antibody light chain

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 63
<211> LENGTH: 619
<212> TYPE: PRT
<213> ORGANISM: artificial
<220> FEATURE:
<223> OTHER INFORMATION: fusion polypeptide

<400> SEQUENCE: 63

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

```
Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Ser Gly Gly Gly
    450                 455                 460

Gly Ser Ala Ser Asp Glu Glu Ile Gln Asp Val Ser Gly Thr Trp Tyr
465                 470                 475                 480

Leu Lys Ala Met Thr Val Asp Phe Trp Cys Ser Gly Ile His Glu Glu
                485                 490                 495

Ser Val Thr Pro Met Thr Leu Thr Leu Glu Gly Gly Asn Leu Glu
            500                 505                 510
```

Ala Lys Val Thr Met Asp Ile Glu Gly Phe Leu Gln Glu Phe Lys Ala
            515                 520                 525

Val Leu Glu Lys Thr Asp Glu Pro Gly Lys Tyr Thr Ala Asp Gly Gly
    530                 535                 540

Lys His Val Ala Tyr Ile Ile Arg Ser Arg Val Lys Asp His Tyr Ile
545                 550                 555                 560

Phe Tyr Ser Glu Gly Asp Cys Pro Pro Val Pro Gly Val Trp Leu
                565                 570                 575

Val Gly Arg Asp Pro Lys Asn Asn Leu Glu Ala Leu Glu Asp Phe Glu
                580                 585                 590

Lys Ala Ala Gly Ala Arg Gly Leu Ser Thr Glu Ser Ile Leu Ile Pro
    595                 600                 605

Arg Gln Ser Glu Thr Ser Ser Pro Gly Ser Asp
    610                 615

<210> SEQ ID NO 64
<211> LENGTH: 644
<212> TYPE: PRT
<213> ORGANISM: artificial
<220> FEATURE:
<223> OTHER INFORMATION: fusion polypeptide

<400> SEQUENCE: 64

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

-continued

```
Ile Ser Arg Thr Pro Glu Val Thr Cys Val Val Asp Val Ser His
            260                 265                 270

Glu Asp Pro Glu Val Lys Phe Asn Trp Tyr Val Asp Gly Val Glu Val
275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Gln Asp Ser Thr Ser Asp Leu Ile Pro Ala Pro Pro Leu Ser
465                 470                 475                 480

Lys Val Pro Leu Gln Gln Asn Phe Gln Asp Asn Gln Phe His Gly Lys
                485                 490                 495

Trp Tyr Val Val Gly Glu Ala Gly Asn Leu Leu Leu Arg Glu Asp Lys
            500                 505                 510

Asp Pro Arg Lys Met Thr Ala Thr Ile Tyr Glu Leu Lys Glu Asp Lys
        515                 520                 525

Ser Tyr Asp Val Thr Arg Val Glu Phe Gly Ala Lys Thr Tyr Lys Tyr
    530                 535                 540

Gln Ile Gly Thr Phe Val Pro Gly Ser Gln Pro Gly Glu Phe Thr Leu
545                 550                 555                 560

Gly Gly Ile Glu Ser Met Pro Gly Met Thr Ser Phe Leu Val Arg Val
                565                 570                 575

Val Ser Thr Asn Tyr Asn Gln His Ala Ile Val Phe Phe Lys Tyr Val
            580                 585                 590

Tyr Gln Asn Arg Glu Tyr Phe Glu Ile Thr Leu Tyr Gly Arg Thr Lys
        595                 600                 605

Glu Leu Thr Ser Glu Leu Lys Glu Asn Phe Ile Arg Phe Ser Lys Ser
    610                 615                 620

Leu Gly Leu Pro Glu Asn His Ile Val Phe Pro Val Pro Ile Asp Gln
625                 630                 635                 640

Ala Ile Asp Gly
```

<210> SEQ ID NO 65
<211> LENGTH: 1353
<212> TYPE: DNA
<213> ORGANISM: artificial
<220> FEATURE:
<223> OTHER INFORMATION: benchmark antibody heavy chain

<400> SEQUENCE: 65

| | | | | | |
|---|---|---|---|---|---|
| gaagtgcagc | tggtcgaaag | tggtggtggt | ctggtgcagc | ccggtagaag | tctgcgtctg | 60 |
| tcttgtgccg | catctggttt | tacattcgac | gattacgcaa | tgcattgggt | gagacaggcc | 120 |
| cccggcaagg | gactggagtg | ggtctccgct | atcacctgga | cagcgggca | tattgactac | 180 |
| gcagattccg | tggaaggcag | gttcacaatc | tctcgggaca | acgccaagaa | tagtctgtat | 240 |
| ctgcagatga | attcactgag | ggccgaggat | accgccgtgt | actattgcgc | taaagtctct | 300 |
| tatctgtcta | ccgcatcatc | tctggattac | tggggtcagg | gaacactggt | cactgtctcc | 360 |
| tctgctagca | caaagggccc | tagtgtgttt | cctctggctc | cctcttccaa | atccacttct | 420 |
| ggtggcactg | ctgctctggg | atgcctggtg | aaggattact | tcctgaaacc | tgtgactgtc | 480 |
| tcatggaact | ctggtgctct | gacttctggt | gtccacactt | ccctgctgt | gctgcagtct | 540 |
| agtggactgt | actctctgtc | atctgtggtc | actgtgccct | cttcatctct | gggaacccag | 600 |
| acctacattt | gtaatgtgaa | ccacaaacca | tccaacacta | aagtggacaa | aaagtggaa | 660 |
| cccaaatcct | gtgacaaaac | ccacacctgc | ccaccttgtc | ctgcccctga | actgctggga | 720 |
| ggaccttctg | tgtttctgtt | cccaccaaaa | ccaaaagata | ccctgatgat | ctctagaacc | 780 |
| cctgaggtga | catgtgtggt | ggtggatgtg | tctcatgagg | accctgaggt | caaattcaac | 840 |
| tggtacgtgg | atggagtgga | agtccacaat | gccaaaacca | gcctagaga | ggaacagtac | 900 |
| aattcaacct | acagagtggt | cagtgtgctg | actgtgctgc | atcaggattg | gctgaatggc | 960 |
| aaggaataca | agtgtaaagt | ctcaaacaag | gccctgcctg | ctccaattga | gaaaacaatc | 1020 |
| tcaaaggcca | agggacagcc | tagggaaccc | caggtctaca | ccctgccacc | ttcaagagag | 1080 |
| gaaatgacca | aaaccaggt | gtccctgaca | tgcctggtca | aaggcttcta | cccttctgac | 1140 |
| attgctgtgg | agtgggagtc | aaatggacag | cctgagaaca | actacaaaac | aaccccccct | 1200 |
| gtgctggatt | ctgatggctc | tttctttctg | tactccaaac | tgactgtgga | caagtctaga | 1260 |
| tggcagcagg | ggaatgtctt | ttcttgctct | gtcatgcatg | aggctctgca | taaccactac | 1320 |
| actcagaaat | ccctgtctct | gtctcctggc | aaa | | | 1353 |

<210> SEQ ID NO 66
<211> LENGTH: 642
<212> TYPE: DNA
<213> ORGANISM: artificial
<220> FEATURE:
<223> OTHER INFORMATION: benchmark antibody light chain

<400> SEQUENCE: 66

| | | | | | |
|---|---|---|---|---|---|
| gacatccaga | tgacccagag | cccaagttcc | ctgagcgcaa | gcgtcggaga | tcgtgtgact | 60 |
| attacctgta | gagcaagcca | gggcatcaga | aactacctgg | catggtatca | gcagaagccc | 120 |
| ggtaaagccc | ctaagctgct | gatctacgcc | gcttccactc | tgcagtctgg | cgtgccaagc | 180 |
| aggttctctg | gcagtggatc | agggaccgac | tttaccctga | caatttccag | cctgcagccc | 240 |
| gaggatgtcg | ctacatacta | ttgccagcgg | tacaatcggg | caccttatac | attcggtcag | 300 |
| gggactaaag | tggaaatcaa | gagaactgtc | gcggcgcctt | ctgtgttcat | tttcccccca | 360 |
| tctgatgaac | agctgaaatc | tggcactgct | tctgtggtct | gtctgctgaa | caacttctac | 420 |
| cctagagagg | ccaaagtcca | gtggaaagtg | gacaatgctc | tgcagagtgg | gaattcccag | 480 |
| gaatctgtca | ctgagcagga | ctctaaggat | agcacatact | ccctgtcctc | tactctgaca | 540 |

| ctgagcaagg ctgattacga gaaacacaaa gtgtacgcct gtgaagtcac acatcagggg | 600 |
| ctgtctagtc ctgtgaccaa atccttcaat aggggagagt gc | 642 |

<210> SEQ ID NO 67
<211> LENGTH: 1857
<212> TYPE: DNA
<213> ORGANISM: artificial
<220> FEATURE:
<223> OTHER INFORMATION: fusion polypeptide

<400> SEQUENCE: 67

| gaagtgcagc tggtcgaaag tggtggtggt ctggtgcagc ccggtagaag tctgcgtctg | 60 |
| tcttgtgccg catctggttt tacattcgac gattacgcaa tgcattgggt gagacaggcc | 120 |
| cccggcaagg gactggagtg ggtctccgct atcacctgga acagcgggca tattgactac | 180 |
| gcagattccg tggaaggcag gttcacaatc tctcgggaca cgccaagaa tagtctgtat | 240 |
| ctgcagatga attcactgag ggccgaggat accgccgtgt actattgcgc taaagtctct | 300 |
| tatctgtcta ccgcatcatc tctggattac tggggtcagg gaacactggt cactgtctcc | 360 |
| tctgctagca caaagggccc tagtgtgttt cctctggctc cctcttccaa atccacttct | 420 |
| ggtggcactg ctgctctggg atgcctggtg aaggattact ttcctgaacc tgtgactgtc | 480 |
| tcatggaact ctggtgctct gacttctggt gtccacactt ccctgctgt gctgcagtct | 540 |
| agtggactgt actctctgtc atctgtggtc actgtgccct cttcatctct gggaacccag | 600 |
| acctacattt gtaatgtgaa ccacaaacca tccaacacta agtggacaa aaaagtggaa | 660 |
| cccaaatcct gtgacaaaac ccacacctgc ccaccttgtc ctgcccctga actgctggga | 720 |
| ggaccttctg tgtttctgtt cccaccaaaa ccaaaagata ccctgatgat ctctagaacc | 780 |
| cctgaggtga catgtgtggt ggtggatgtg tctcatgagg accctgaggt caaattcaac | 840 |
| tggtacgtgg atggagtgga agtccacaat gccaaaacca gcctagaga ggaacagtac | 900 |
| aattcaacct acagagtggt cagtgtgctg actgtgctgc atcaggattg gctgaatggc | 960 |
| aaggaataca agtgtaaagt ctcaaacaag gccctgcctg ctccaattga aaaacaatc | 1020 |
| tcaaaggcca agggacagcc tagggaaccc caggtctaca ccctgccacc ttcaagagag | 1080 |
| gaaatgacca aaaaccaggt gtccctgaca tgcctggtca aaggcttcta cccttctgac | 1140 |
| attgctgtgg agtgggagtc aaatggacag cctgagaaca actacaaaac aacccccct | 1200 |
| gtgctggatt ctgatggctc tttctttctg tactccaaac tgactgtgga caagtctaga | 1260 |
| tggcagcagg ggaatgtctt tcttgctct gtcatgcatg aggctctgca taaccactac | 1320 |
| actcagaaat ccctgtctct gtctcctggc aaaggcggcg gaggatccgg cggaggaggt | 1380 |
| agcggcggag gaggtagcgc atcagacgag gaaatccagg acgtgtcagg acctggtac | 1440 |
| ctgaaagcca tgaccgtgga tttttggtgc tccggcatcc atgaggagtc agtcactccc | 1500 |
| atgacccctg aacccctaga aggtgggaat ctggaggcca agtgacaat ggatattgag | 1560 |
| ggctttctcc aggagttcaa agccgtcctc gagaagacag acgagcctgg aaagtatact | 1620 |
| gctgatgggg gaaaacacgt agcctatatc attcgatctc gggtgaagga tcattatatc | 1680 |
| ttctattccg agggcgactg ccccggccct gtgccaggtg tctggctagt tgggagggac | 1740 |
| cccaagaaca atctcgaggc tctggaggac ttcgagaagg cagctggtgc caggggattg | 1800 |
| agcactgagt ctatccttat cccacgccag agcgagacct caagcccagg gtccgac | 1857 |

<210> SEQ ID NO 68
<211> LENGTH: 1932
<212> TYPE: DNA
<213> ORGANISM: artificial
<220> FEATURE:
<223> OTHER INFORMATION: fusion polypeptide

<400> SEQUENCE: 68

| | | | | | |
|---|---|---|---|---|---|
| gaagtgcagc | tggtcgaaag | tggtggtggt | ctggtgcagc | ccggtagaag | tctgcgtctg | 60 |
| tcttgtgccg | catctggttt | tacattcgac | gattacgcaa | tgcattgggt | gagacaggcc | 120 |
| cccggcaagg | gactggagtg | gtctccgct | atcacctgga | acagcgggca | tattgactac | 180 |
| gcagattccg | tggaaggcag | gttcacaatc | tctcgggaca | acgccaagaa | tagtctgtat | 240 |
| ctgcagatga | attcactgag | ggccgaggat | accgccgtgt | actattgcgc | taaagtctct | 300 |
| tatctgtcta | ccgcatcatc | tctggattac | tggggtcagg | gaacactggt | cactgtctcc | 360 |
| tctgctagca | caaagggccc | tagtgtgttt | cctctggctc | cctcttccaa | atccacttct | 420 |
| ggtggcactg | ctgctctggg | atgcctggtg | aaggattact | tccctgaacc | tgtgactgtc | 480 |
| tcatggaact | ctggtgctct | gacttctggt | gtccacactt | tccctgctgt | gctgcagtct | 540 |
| agtggactgt | actctctgtc | atctgtggtc | actgtgccct | cttcatctct | gggaacccag | 600 |
| acctacattt | gtaatgtgaa | ccacaaacca | tccaacacta | aagtggacaa | aaagtggaa | 660 |
| cccaaatcct | gtgacaaaac | ccacacctgc | ccaccttgtc | ctgccctga | actgctggga | 720 |
| ggaccttctg | tgtttctgtt | cccaccaaaa | ccaaaagata | ccctgatgat | ctctagaacc | 780 |
| cctgaggtga | catgtgtggt | ggtggatgtg | tctcatgagg | accctgaggt | caaattcaac | 840 |
| tggtacgtgg | atggagtgga | agtccacaat | gccaaaacca | agcctagaga | ggaacagtac | 900 |
| aattcaacct | acagagtggt | cagtgtgctg | actgtgctgc | atcaggattg | gctgaatggc | 960 |
| aaggaataca | agtgtaaagt | ctcaaacaag | gccctgcctg | ctccaattga | gaaaacaatc | 1020 |
| tcaaaggcca | agggacagcc | tagggaaccc | caggtctaca | ccctgccacc | ttcaagagag | 1080 |
| gaaatgacca | aaaaccaggt | gtccctgaca | tgcctggtca | aaggcttcta | cccttctgac | 1140 |
| attgctgtgg | agtgggagtc | aaatggacag | cctgagaaca | actacaaaac | aaccccccct | 1200 |
| gtgctggatt | ctgatggctc | tttcttcctg | tactccaaac | tgactgtgga | caagtctaga | 1260 |
| tggcagcagg | ggaatgtctt | tcttgctct | gtcatgcatg | aggctctgca | taaccactac | 1320 |
| actcagaaat | ccctgtctct | gtctcctggc | aaaggcggcg | gaggatccgg | gggtggggga | 1380 |
| agcggcggag | gaggtagcca | ggattcaacc | agcgatctga | ttccagcacc | gccactgtcg | 1440 |
| aaagtgccac | tgcaacaaaa | ctttcaagat | aaccagtttc | acggcaagtg | gtatgtggtc | 1500 |
| ggggaggccg | gtaacctgct | gctgagggaa | gacaaagatc | cacggaaaat | gaccgccacc | 1560 |
| atctacgagc | tgaaagagga | taagtcctac | gacgtgactc | gggtggagtt | cggcgcaaaa | 1620 |
| acctacaagt | accagatcgg | caccttcgtg | cccggctctc | agcctggcga | gtttaccctg | 1680 |
| ggcggcatcg | aatctatgcc | cggcatgacc | agctttctcg | tgcgggtggt | gtccaccaac | 1740 |
| tacaaccagc | acgccatcgt | gttcttcaaa | tacgtgtacc | agaaccgcga | gtacttcgag | 1800 |
| atcaccctgt | acggccggac | caaagagctg | acctccgaac | tgaaagagaa | cttcatccgg | 1860 |
| ttctccaagt | ccctgggcct | gcccgagaac | cacatcgtgt | tccccgtgcc | tatcgaccag | 1920 |
| gccatcgacg | gc | | | | | 1932 |